US008772253B2

United States Patent
Núñez González et al.

(10) Patent No.: US 8,772,253 B2
(45) Date of Patent: Jul. 8, 2014

(54) AUREOLIC ACID DERIVATIVES, THE METHOD FOR PREPARATION THEREOF AND THE USES

(75) Inventors: Luz Elena Núñez González, Oviedo (ES); Nuria Menéndez Sánchez, Oviedo (ES); Javier González Sabin, Oviedo (ES); Francisco Moris Varas, Oviedo (ES); Beatriz García Fernández, Oviedo (ES); Maria Pérez Solares, Oviedo (ES); Alfredo Fernández Braña, Oviedo (ES); Maria del Carmen Méndez Fernández, Oviedo (ES); José Antonio Salas Fernández, Oviedo (ES)

(73) Assignee: Entrechem, S.L., Oviedo (ES)

( * ) Notice: Subject to any disclaimer, the term of this patent is extended or adjusted under 35 U.S.C. 154(b) by 124 days.

(21) Appl. No.: 13/384,816

(22) PCT Filed: Jul. 14, 2010

(86) PCT No.: PCT/ES2010/070489
§ 371 (c)(1),
(2), (4) Date: Apr. 19, 2012

(87) PCT Pub. No.: WO2011/009987
PCT Pub. Date: Jan. 27, 2011

(65) Prior Publication Data
US 2012/0270823 A1    Oct. 25, 2012

(30) Foreign Application Priority Data

Jul. 23, 2009  (ES) .................................. 200930497

(51) Int. Cl.
*A61K 31/70*      (2006.01)
*C07H 15/00*      (2006.01)
*C12P 19/42*      (2006.01)
*C12P 19/56*      (2006.01)

(52) U.S. Cl.
USPC ................. 514/33; 536/4.1; 435/78; 435/886

(58) Field of Classification Search
USPC ....................... 536/4.1; 435/78, 886
See application file for complete search history.

(56) References Cited

U.S. PATENT DOCUMENTS 8,426,169 B2 *  4/2013  Rohr et al. ...................... 435/78
2005/0192432 A1  9/2005  Rohr et al.

FOREIGN PATENT DOCUMENTS

WO    2008096028 A1    8/2008

OTHER PUBLICATIONS

Perez, M. et al., "Generation of New Derivatives of the Antitumor Antibiotic Mithramycin by Altering the Glycosylation Pattern through Combinatorial Biosynthesis," ChemBioChem, 2008, pp. 2295-2304, vol. 9.
Saito, T. et al., "Combination Chemotherapy for Solid Tumors using 5-fluorouracil, Chromomycin-A3, and Prednisolone," GANN, Aug. 1977, pp. 375-387, vol. 68.
Menendez, N. et al., "Tailoring modification of deoxysugars during biogynthesis of the antitumour drug chromomycin A3 by *Streptomyces griseus* ssp. *griseus*," Molecular Microbiology, 2004, pp. 903-915, vol. 53.
Kawano, T. et al., "Isolation and Structures of Momo- and Di-Deacetyl Chromomycin Antibiotics 02-3D and 02-3G from *Streptomyces avellaneus*," The Journal of Antibiotics, Jan. 1990, pp. 110-113, vol. 43.
International Search Report, Nov. 26, 2010.

* cited by examiner

*Primary Examiner* — Elli Peselev
(74) *Attorney, Agent, or Firm* — Tristan A. Fuierer; Moore & Van Allen, PLLC

(57) ABSTRACT

Aureolic acid derivatives, process for obtaining them and uses thereof. This invention provides a bacterial strain that produces compound belonging to the family of aureolic acids useful in the treatment of cancer or nervous system diseases.

15 Claims, 21 Drawing Sheets

US 8,772,253 B2

AUREOLIC ACID DERIVATIVES, THE METHOD FOR PREPARATION THEREOF AND THE USES

CROSS-REFERENCE TO RELATED APPLICATIONS

This application is filed under the provisions of 35 U.S.C. §371 and claims the priority of International Patent Application No. PCT/ES2010/070489 filed on 14 Jul. 2010 entitled "Aureolic Acid Derivatives, the Method for Preparation Thereof and the Uses Thereof" in the name of Luz Elena NÚÑEZ GONZÁLEZ, et al., which claims priority to Spanish Patent Application No. P200930497 filed on 23 Jul. 2009, both of which are hereby incorporated by reference herein in their entirety.

FIELD OF THE INVENTION

The invention belongs to the pharmaceutical field and specifically relates to compounds with application in oncology, with a chemical structure derived from aureolic acids and are obtained by fermentation of microorganisms and/or enzymatic acylation catalyzed by lipases.

STATE OF THE ART

The aureolic acid family of compounds is a group of secondary metabolites synthesized by bacteria of the genus *Streptomyces*. This family is composed by mithramycin (MTM), the chromomycins, the olivomycins, chromocyclomycin, UCH9 and durhamycin (*Appl. Microbiol. Biotechnol.* 2006, 73, 1-14).

The members of the aureolic acid family of compounds have very interesting biological properties with potential application in the pharmaceutical industry like antibacterial activity, antiviral activity and neuroprotective activity but the main interest is due to their antitumor activity. For example, MTM has been used in the clinic in the treatment of some types of cancer such as testicular cancer, chronic myeloid leukemia and acute myeloid leukemia. It has been used for the treatment of Paget's disease and hypercalcemia caused by bone lesions associated with cancer (*Oncology* 1973, 28, 147-163; *Biochem. Biophys. Res. Comun.* 1993, 195, 1245-1253; *Treat. Endocrinol.* 2002, 1, 241-257; *Treat. Endocrinol.* 2003, 2, 273-292). MTM and chromomycin A3 (CRM) have been described as potent inhibitors of aberrant neuronal apoptosis associated with certain neurology disorders (*Ann. Neurol.* 2001, 49, 345-354), suggesting that these molecules could be useful for treating neurologic diseases such as stroke, Lou Gehrig's disease, Parkinson's disease, Huntington's disease, multiple sclerosis and viral encephalitis (*J. Neurosci.* 2004, 24, 10335-10342; *J. Biol. Chem.* 2006, 281, 16672-16680). More recently, the use of MTM in combination therapy as an angiogenic agent has been reported for the treatment of pancreas and other types of cancer (*Cancer Res.* 2007, 67, 4878-4885).

The different biological activities of aureolic acids are the consequence of their mechanisms of action at cell level. The non-covalent binding of these molecules (as dimers in presence of $Mg^{2+}$) to the DNA minor grove in regions of high GC content cause inhibition of transcription by displacing the transcription activators bound to GC rich sequences present in some promoters (*J. Clin. Invest.* 1989, 83, 2003-2007; *J. Clin. Invest.* 1991, 88, 1613-1621). This is the case of transcription factors Sp1, a family of DNA binding proteins very important for transcription of cell and viral genes that contain GC boxes in their promoter regions. Sp1 factors regulate several biologic functions including cell survival, growth and differentiation and development and tumor progression (*J. Cell. Physiol.* 2001, 188, 143-160).

The structure of the aureolic acid group of compounds consists of a chromophore part (aglycone) of polyketide origin assembled in three rings (four rings in chromocyclomycin) and a side chain highly functionalized in position 3. With the exception of olivomycin, they have an alkyl group in position 9 (methyl or isobutyl). These compounds contain 2,6-deoxysugars distributed as a tri- or tetrasaccharide (in position 2) and a mono- or disaccharide (in position 6). The compounds of the aureolic acid group can have different glycosylation pattern and different 2,6-dideoxysugars attached to the aglycone. These structural variations are responsible of the subtle differences of these compounds regarding their DNA binding properties and consequently their biologic activity profile. It is well known that the glycosylation pattern of DNA binding antitumor compounds like the aureolic acids is very important for the biologic activity. Based on these properties, obtaining MTM derivatives with altered glycosylation patterns might generate compounds with improved activity.

MTM and CRM (FIG. 1) are the most representative members of the aureolic acid family. MTM is an antitumor compound produced by microorganisms of the genus *Streptomyces*, including *Streptomyces argillaceus* ATCC 12956. CRM is produced, among others, by *Streptomyces griseus* ssp. *griseus* ATCC 13276. The biosynthesis of MTM and CRM has been thoroughly studied in the producing strains mentioned above (*Appl. Microbiol. Biotechnol.* 2006, 73, 1-14). The gene clusters responsible for the biosynthesis of both molecules have been fully sequenced. Inactivation of many biosynthetic genes has been useful to gain information on the biosynthetic mechanism of aureolic acids. For example, it has been reported that the biosynthesis of these molecules starts with the condensation of ten units of acyl-CoA to generate a tertacyclic intermediate called premithramycinone. The next step is the successive addition of five deoxysugars, generating tetracylcic intermediates with different number of sugars attached to the aglycone. In one of the final steps of the pathway, an oxygenase produces the opening of one of the rings, generating a tricyclic structure with an aliphatic side chain at position 3 of the aglycone. Finally, reduction of the keto group of the side chain is required to synthesise the final product.

For CRM, there are two additional biosynthetic steps that modify the sugars once they have been transferred to the aglycone, a methylation in position 4B (carried out by CmmMIII) and two acetylations in positions 4A and 4E (carried out by CmmA). The presence of these methyl and acetyl groups in the sugars of CRM confers specific characteristics to the DNA binding as these groups provide additional hydrogen bonds to the amino group of guanine increasing the specificity to the DNA binding (*Biochem.* 1997, 36, 2291-2299). The relevance of the presence of the acetyl groups for the activity of CRM has been shown by the inactivation of the gene cmmA in *S. griseus* allowing the production of a deacetylated derivative of CRM significantly lower antitumor activity when compared to the parent compound (*Mol. Microbiol.* 2004, 53, 903-915). It seems that production of new derivatives of aureolic acids with different acetylation patterns could generate compounds with more interesting properties.

There is a need for more antitumor agents with better activity, less unwanted secondary effects and more selectivity. The development of recombinant DNA technology has opened an interesting field of generating new bioactive compounds by manipulating the genes involved in the biosynthesis of antitumor agents mainly produced by bacteria of the actinomyete group. This technology can also be used to improve production of known natural products that are naturally produced at low level.

Genetic manipulation of microorganisms has been used to obtain new derivatives of aureolic acids (*Appl. Microbiol. Biotechnol.* 2006, 73, 1-14). Some of these derivatives have improved properties when compared to the parent compound. This is the case of the compounds obtained from *Streptomyces argillaceus* M7W1, this strain was generated from *Streptomyces argillaceus* by inactivation of the gene mtmW (U.S. Pat. No. 7,423,008 B2; *J. Am. Chem. Soc.* 2003, 125, 5745-5753). The mtmW gene encodes a ketoreductase and its inactivation produces the accumulation of 3D-demycarosyl-MTM-SK, MTM-SK, MTM-SA and MTM-SDK, these molecules have a different side chain at position 3 when compared to MTM.

Biocatalysis is a very efficient tool to modify complex natural products and generate diversity (*Curr. Opin. Chem. Biol.* 2001, 5, 106-111; *Curr. Opin. Biotechnol.* 1999, 10, 130-136). Particularly, the discovery that lipases and proteases (enzymes that hydrolyse lipids and proteins respectively) can catalyze reactions in organic solvents different from its natural aqueous environment, has produced a considerable increase of research using these type of biocatalysts. They are particulary attractive because of the chemioselective, regioselective and stereoselective nature of the catalytic processs and the ability to operate at very mild reaction conditions. There are reports of lipase assisted regioselective acylation of a great variety of polyhydroxylated natural products such as nucleosides, saponins, flavonoids, terpenes, alkaloids and glycosylated polyketides. New compounds with improved activity have been obtained from this type of acylation derived libraries.

Aureolic acids contain a high number of hydroxyl groups in the aglycone core and in the tailoring sugars that can be acylated. However, despite this obvious potential to generate more compounds, there is no precedent of this type of enzymatic modifications for this family of compounds.

DESCRIPTION OF THE INVENTION

The present invention provides a new bacterial strain called *Streptomyces argillaceus* ΔAH-W⁻ (pMP3*BII) that produces new derivatives of MTM. For constructing this strain the parent strain was a recombinant strain called *Streptomyces argillaceus* ΔAH, a previously described strain that overproduces MTM and the genes mtmA and mtmH have been inactivated (*Appl. Microbiol. Biotechnol.* 2006, 73, 1-14). Inactivation of mtmW was carried out on this strain to produce the double mutant *S. argillaceus* ΔAH-W⁻ (see example 1). The gene mtmW encodes a ketoreductase and its inactivation in the wild type strain is responsible for the accumulation of 3D-demycarosyl-MTM-SK, MTM-SK, MTM-SA and MTM-SDK (U.S. Pat. No. 7,423,008 B2; *J. Am. Chem. Soc.* 2003, 125, 5745-5753). Finally, the construction of strain *Streptomyces argillaceus* ΔAH-W⁻ (pMP3*BII) involves the introduction of a nucleic acid molecule to the mutant ΔAH-W⁻.

More specifically, the nucleic acid molecule used in the present invention is plasmid pMP3*BII (*Appl. Environ. Microbiol.* 2006, 72, 6644-6652). This plasmid contains nucleic acids that encode enzymes involved in the biosynthesis of nucleosidyl-diphosphate (NDP)-D-digitoxose, a sugar that is not naturally made by *S. argillaceus*.

Introduction of nucleic acids into *Streptomyces argillaceus* (or derivative strains) can be carried out by protoplasts transformation, conjugation or other known methods (as the ones described in Practical *Streptomyces* Genetics, The John Innes Foundation, Norwich, UK, 2000), in a way that the nucleic acids can be replicated in the organism as an extrachromosomal element or integrated in the organism chromosome. The bacterial strain of this invention can be cultured in any suitable medium under conditions that allow growth as described in *Gene* 1996, 172, 87-91; *J. Bacteriol.* 1998, 180, 4929-4937; *J. Am. Chem. Soc.* 2003, 125, 5745-5753. After several days of incubation, these cultures contain a high amount of cells (mycelium) and a mixture of compounds including aureolic acid derivatives. Then, the cultures can be treated in different way to obtain a liquid phase (supernatant) and a solid phase (mycelium). The two phases can be processed by means of solvent extraction and different types of chromatography (such as HPLC) in order to obtain the aureolic acid derivatives as pure compounds.

The present invention, also provides new compounds belonging to the family of aureolic acids, derivatives of MTM and CRM. These new derivatives have modifications of the glycosylation and/or acylation pattern when compared to the parent moelcules and can be obtained by; a) production of new compounds by a genetically modified strain; b) bioconversion carried out by enzymes present in a microorganism of substrates added to the culture medium; c) enzymatic acylation catalyzed by lipases.

In the context of the present invention it is understood by bioconversion the biologic transformation of a substrate, carried out by a microorganism, to a chemically modified entity. Particularly, in the present invention, the recombinant organism *Streptomyces griseus* ssp. *griseus* C10GIV (*Appl. Environ. Microbiol.* 2006, 72, 167-177) is used to obtain aureolic acid derivatives with modifications in the acylation pattern. This strain can acetylate MTM derivatives added to the culture medium because it contains the enzyme CmmA, an acyltransferase responsible for the modification of the sugars of CRM at positions 4A and 4E (*Mol. Microbiol.* 2004, 53, 903-915).

In the context of the present invention it is understood by enzymatic acylation the regioselective transformation of a substrate into an acylated derivative by the reaction of an acylating agent catalysed by a lipase. Useful lipases for acylation processes can be then ones described in *Tetrahedron* 2004, 60, 501-519; *Chem. Soc. Rev.* 2004, 33, 201-209; or *Adv. Synth. Catal.* 2006, 348, 797-812. Particularly for this invention, lipase B from *Candida antarctica* (CAL-B) and lipase A from *Candida antarctica* (CAL-A) were used to obtain derivatives of aureolic acids acylated in both, the sugars and the aglycone. These lipases are immobilised in different supports such as mechanically resistant hydrophobic supports or acrylic resins like a decaoctyl activated epoxyacrylic resin. Useful acylating agents for the present invention are those that can be substrates of the lipase and produce acylated aureolic acids and can be esters, carbonates and anhydrides. Preferably, the acylating agent and the solvent are the same, with the exception of reactions in which the aureolic acid is not soluble in the acylating agent or the agent is a solid, in this case solubilization can be facilitated by the addition of tetrahydrofuran. Generally, the reaction temperature should not alter the enzyme structure and denaturation should not take place. The reaction can be carried out at temperatures between 5° C. and 60° C., preferably between 10° C. and 60° C. or at the particularly preferred temperature range of 20° C. and 50° C.

The present invention, also provides the compounds with the general formula (I):

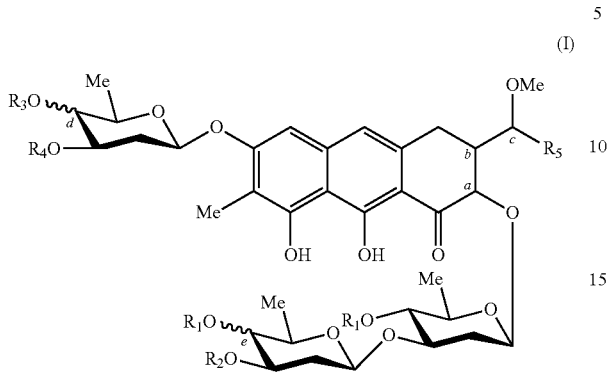

where, $R_1$ is hydrogen or a protecting group, $R_2$ is hydrogen or a protecting group, or a monosaccharide of formula (II),

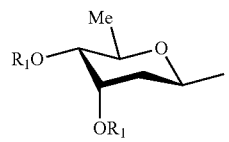

or a monosaccharide of formula (III),

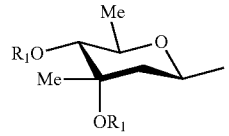

or a monosaccharide of formula (IV),

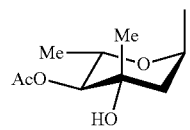

$R_3$ is hydrogen or an acetyl group, $R_4$ is a monosaccharide of formula (V),

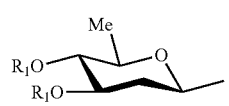

or a monosaccharide of formula (VI)

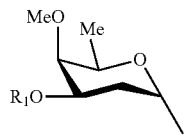

$R_5$ can be selected from the following substituents;

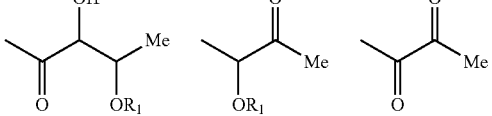

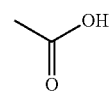

considering that if $R_2$ is the monosaccharide of formula (III) or the monosaccharide of formula (IV), at least one of the R1 groups must be a protecting group and considering that if $R_2$ is hydrogen and $R_5$ is

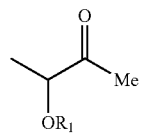

then at least one of the R1 groups must be a protecting group.

A protecting group comprises, but is not limited to, an alkyl group, a cycloalkyl group, a heterocyclic cycloalkyl group, a hydroxyalkyl group, a halogenated alkyl group, an alkoxyalkyl group, an alkenyl group, an alkinyl group, an aryl group, a heterocyclic aryl group, an alkylaryl group, an ester group, a carbonate group, a carboxylic acid group, an aldehyde group, a ketone group, a urethane group, a silyl group, a sulfoxo group, or a combination of these groups.

The stereochemistry of carbons a, b and c and the chiral centers present in R5 can be R, S or a mixture of them.

For the effect of the present invention and its descriptions the two wavy bonds in general formula (I) on carbons d and e mean that that the corresponding susbtituents can be in axial or equatorial position.

The present invention provides, particularly and among others, the compounds with formula (VII, VIII, IX, X, XI, XII, XIV, XXIII, XXIV, XXV, XXIX, XXX, XXXI, XXXII, XXXIV, XXXVI, XXVIII, XLI, XLIV, XLV, XLVI, XLVII, XLVIII, XLIX, LI, LII, LIII, LIV, LV, LVI, LVII, LVIII, LXI, LXIX, LXXX, XCII, XCIII, XCIV, XCV)

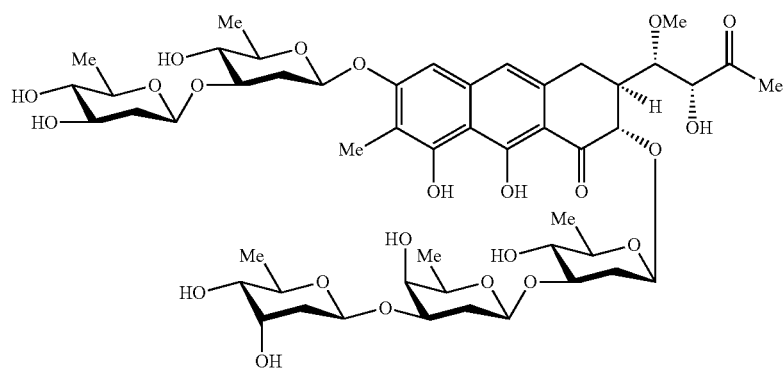
(VII)
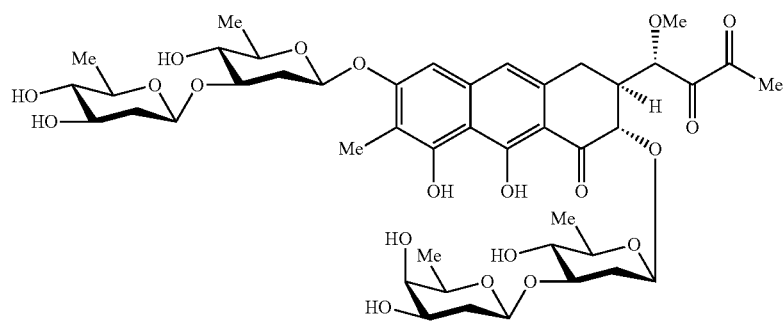
(VIII)
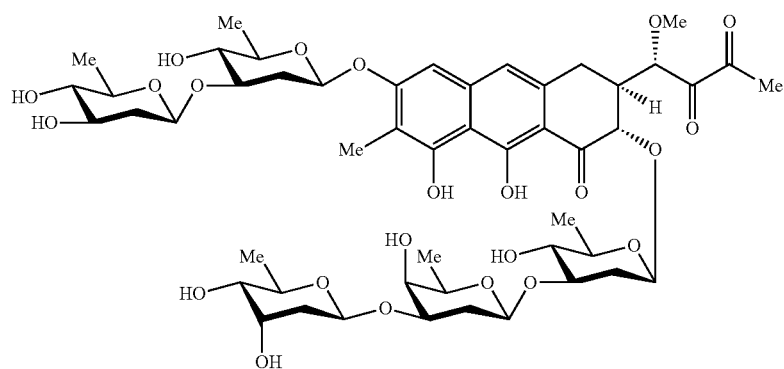
(IX)
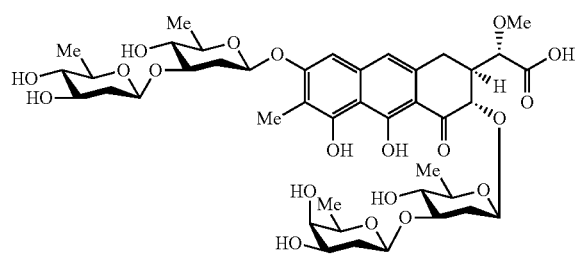
(X)
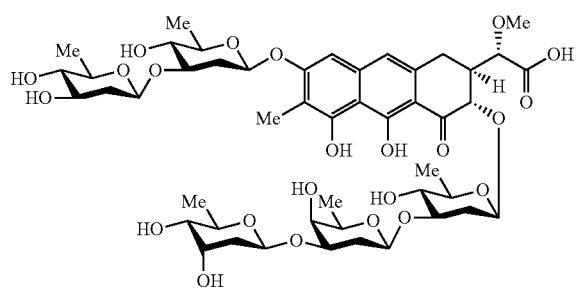
(XI)

-continued
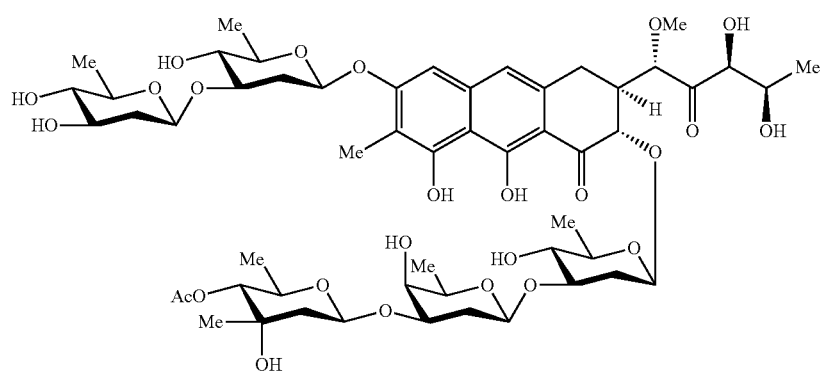
(XII)
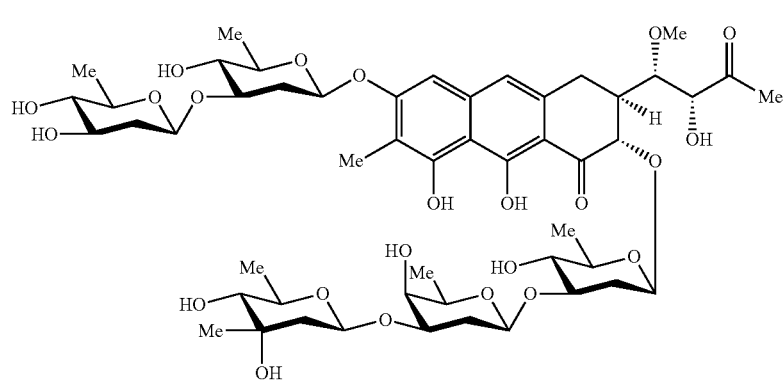
(XIV)
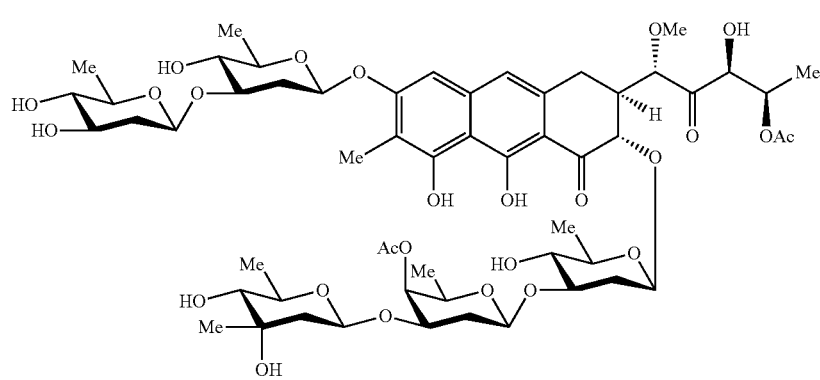
(XXIII)
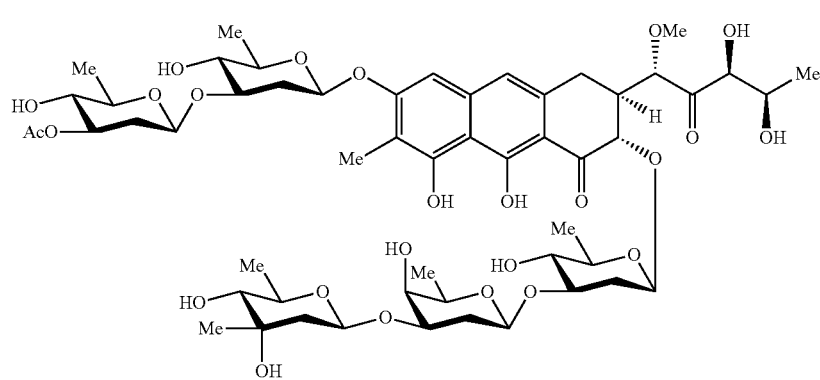
(XXIV)

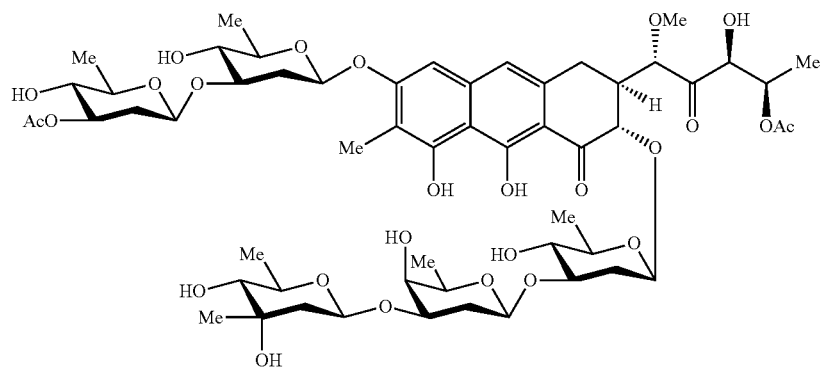
(XXV)
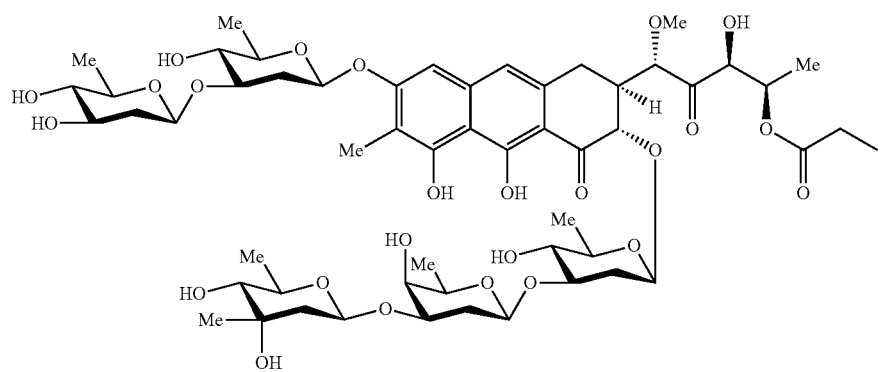
(XXIX)
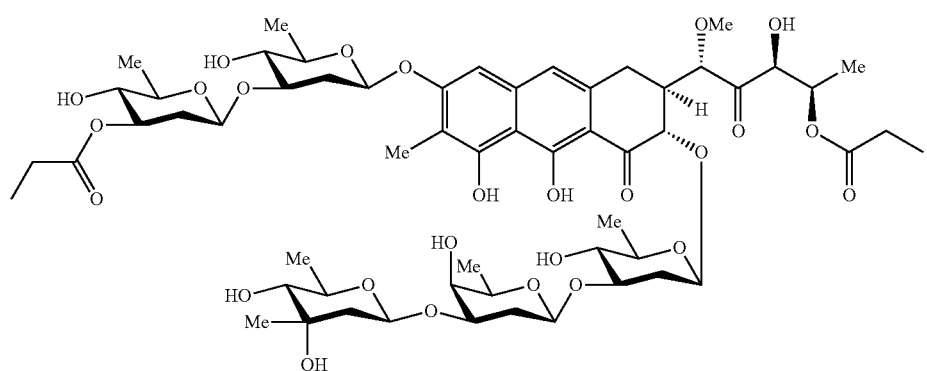
(XXX)
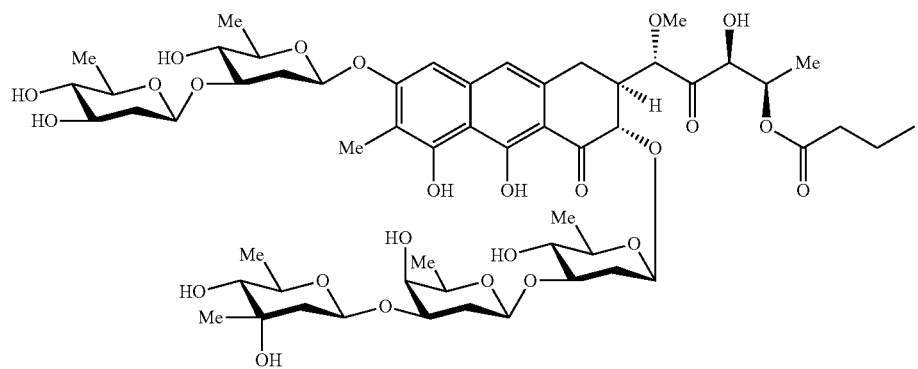
(XXXI)

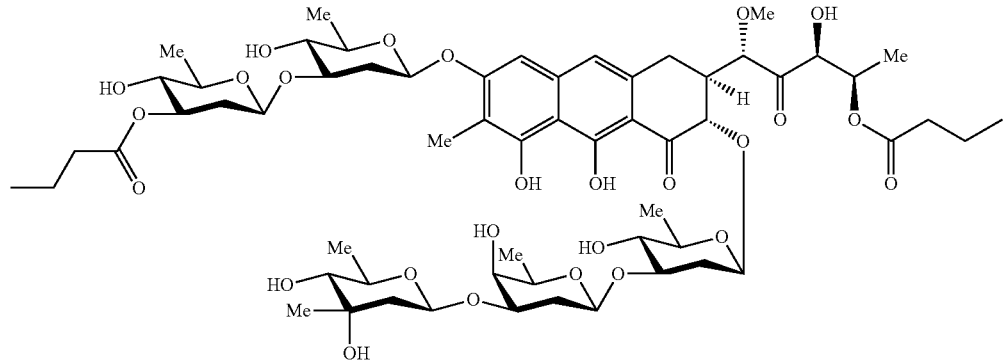
(XXXII)
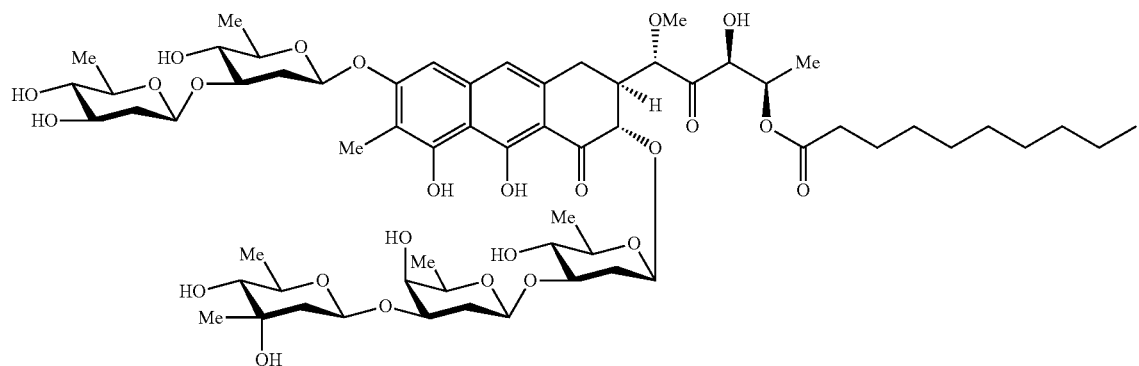
(XXXIV)
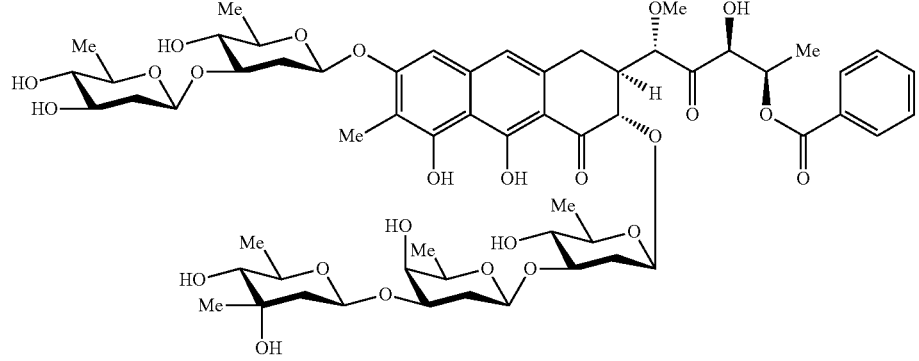
(XXXVI)
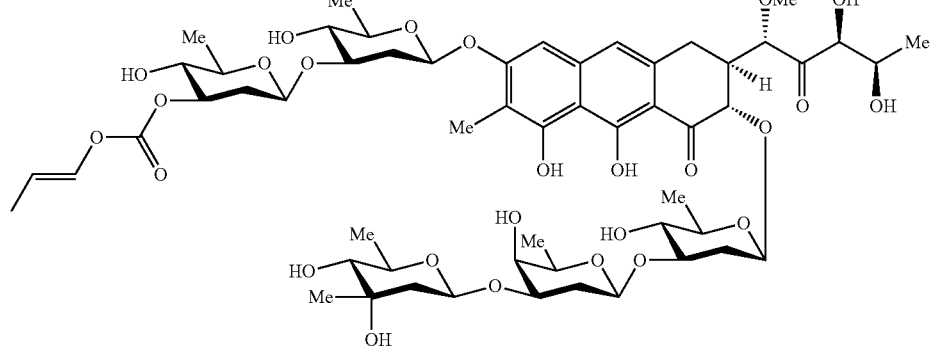
(XXXVIII)

-continued
(XLI)
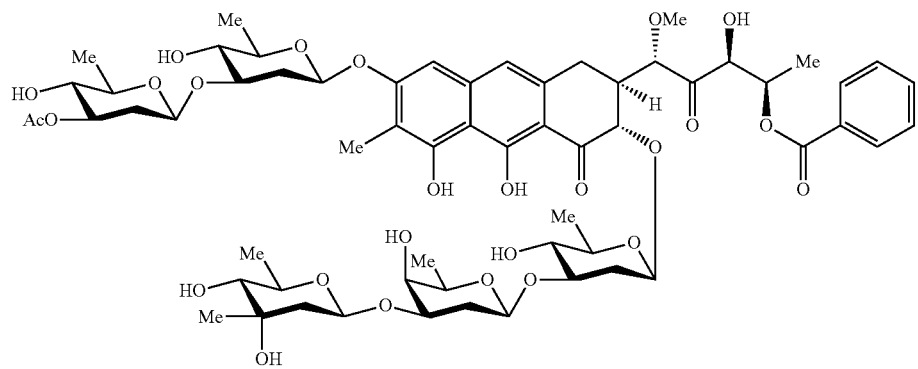
(XLIV)
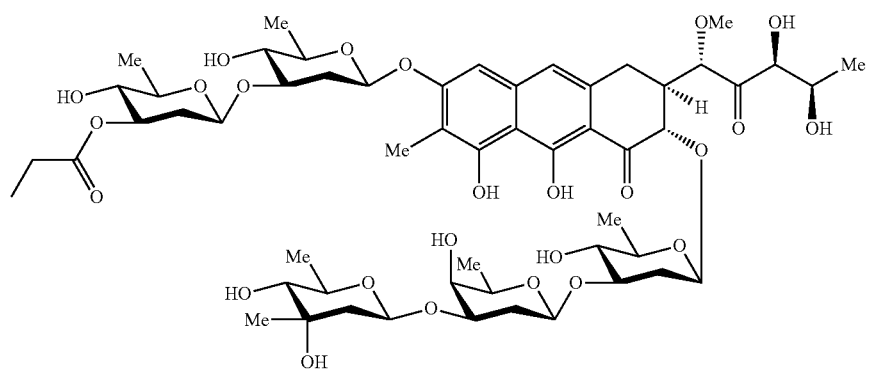
(XLV)
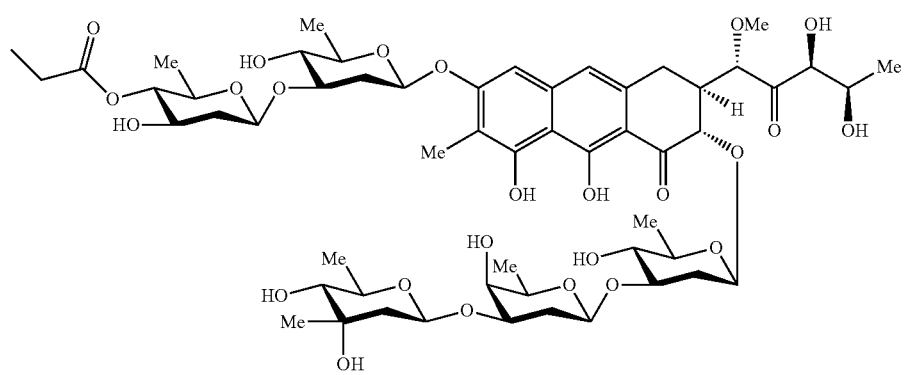
(XLVI)
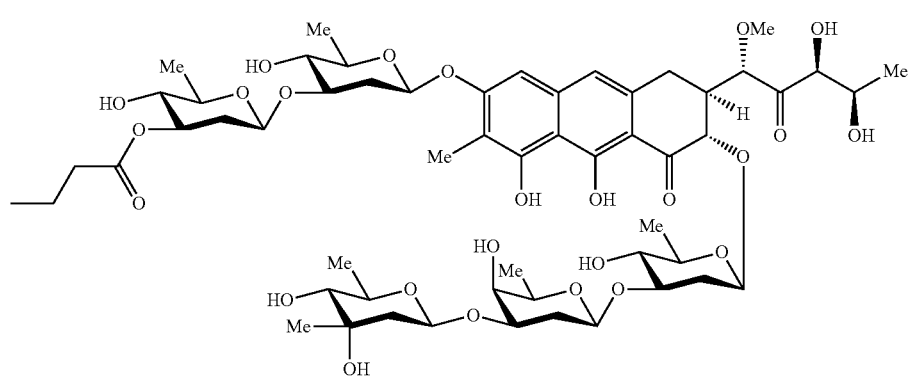

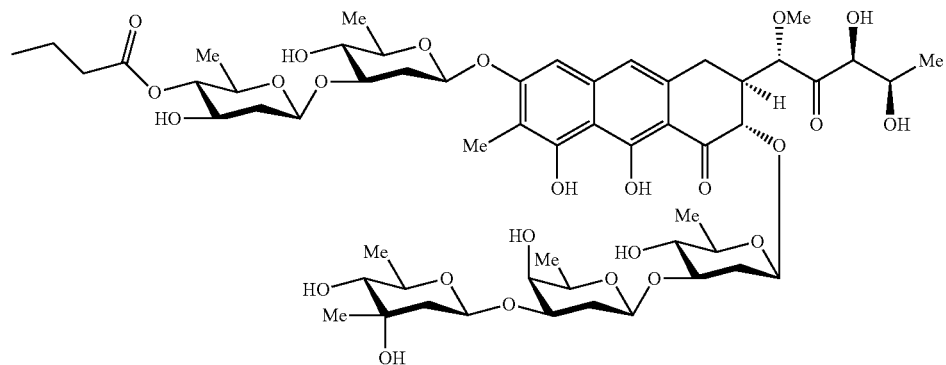
(XLVII)
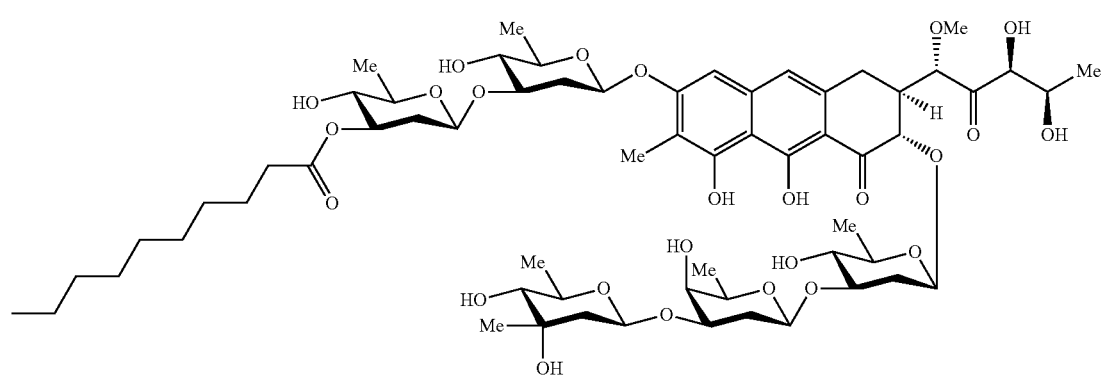
(XLVIII)
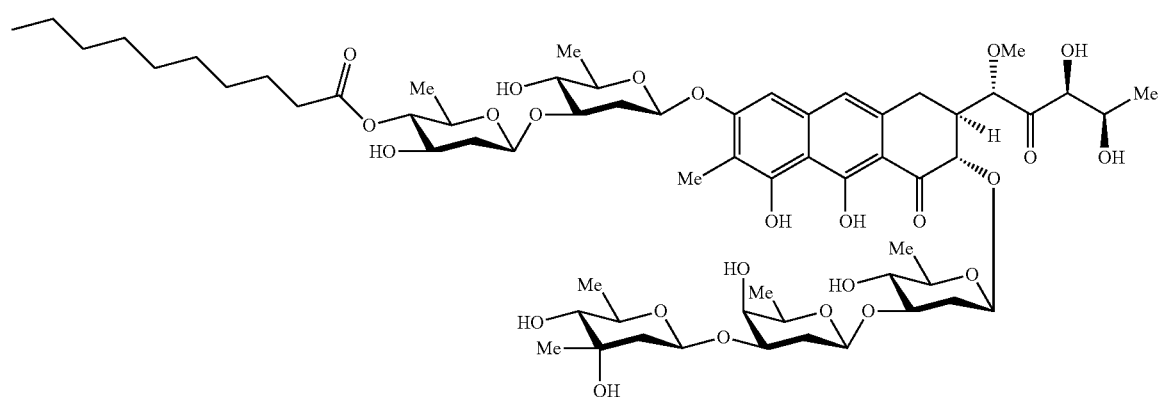
(XLIX)
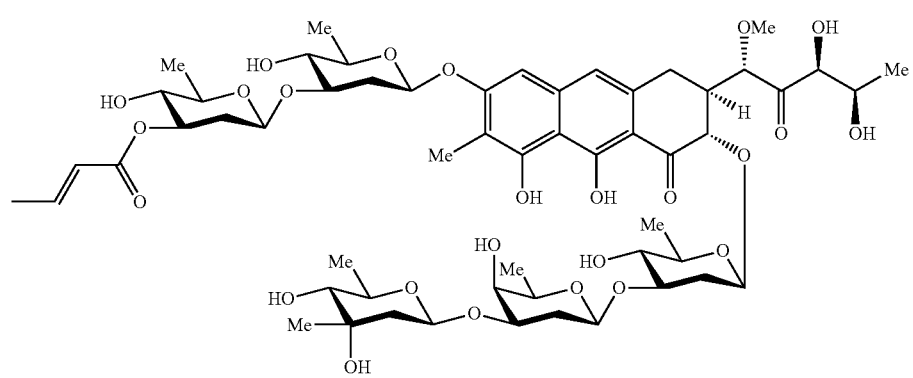
(LI)

-continued
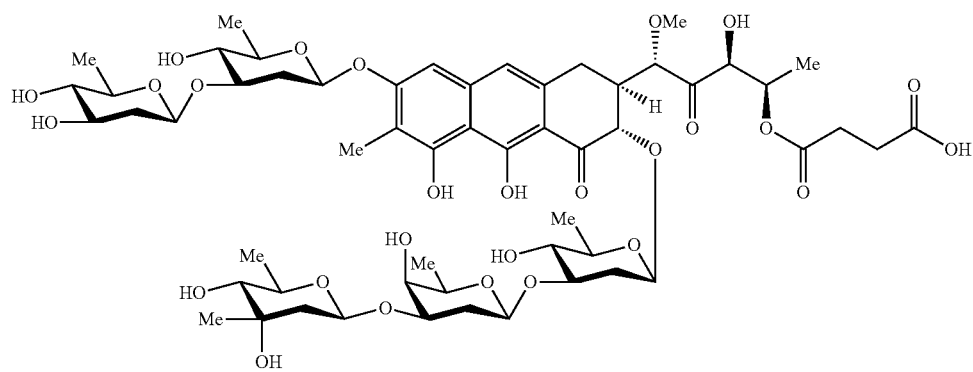
(LII)
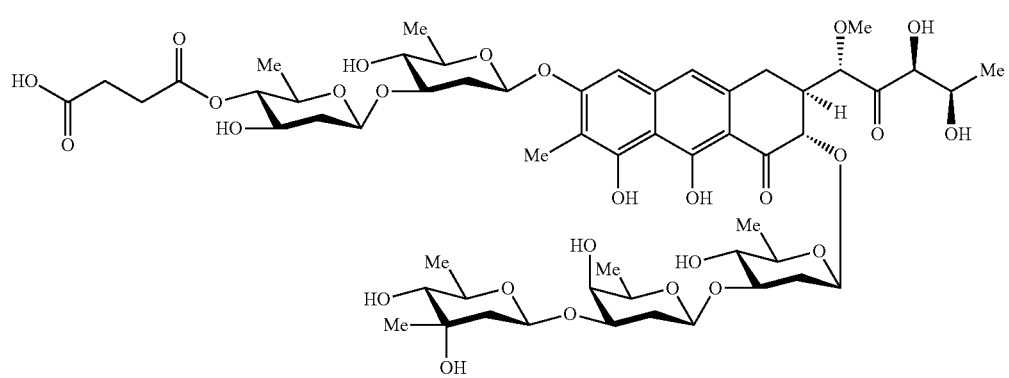
(LIII)
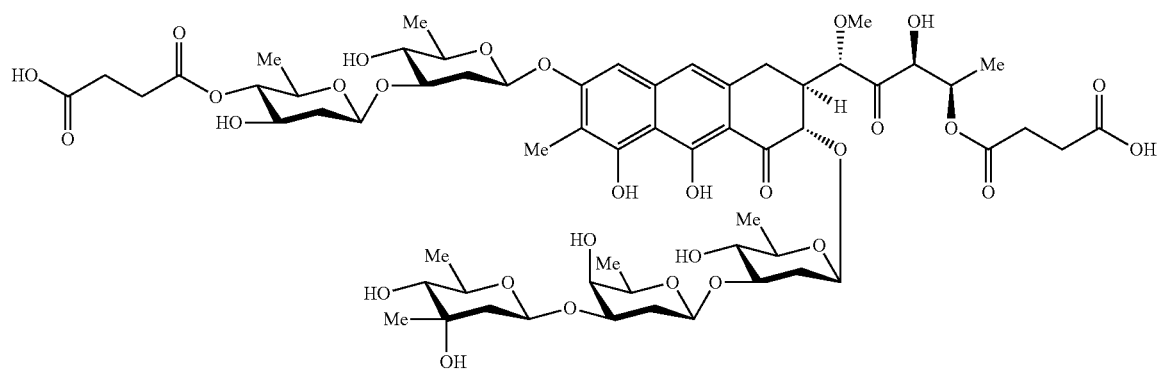
(LIV)
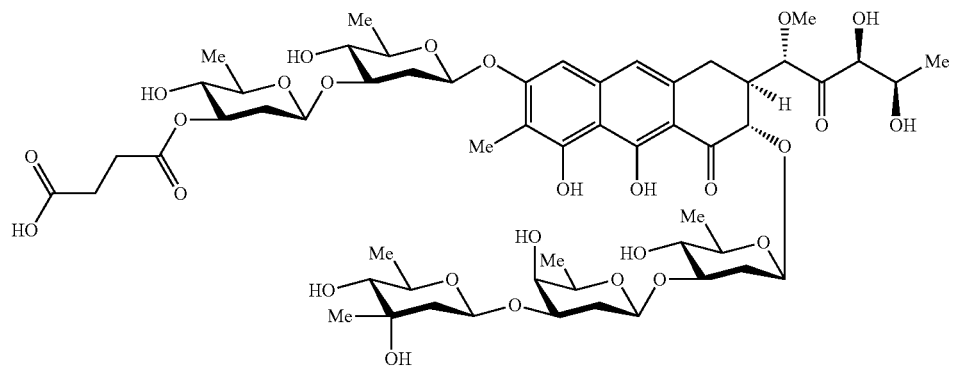
(LV)

-continued
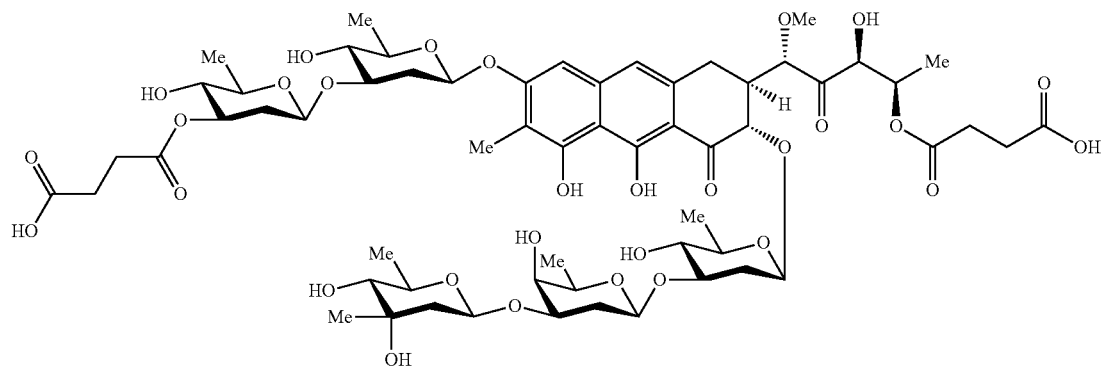
(LVI)
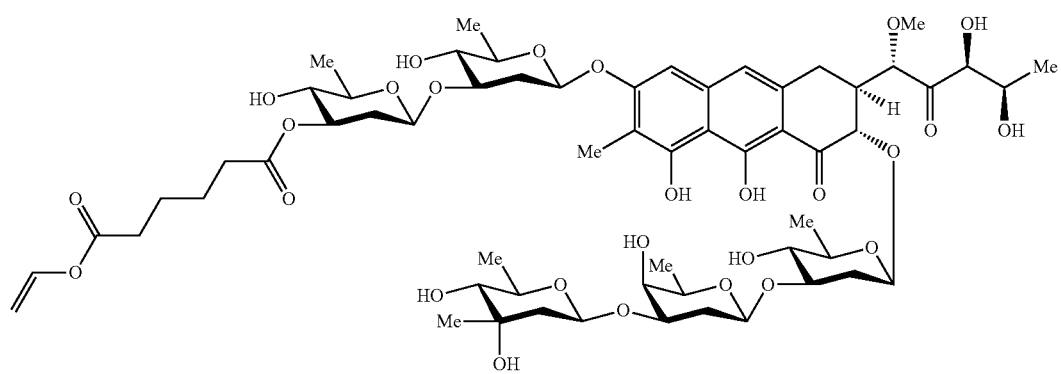
(LVII)
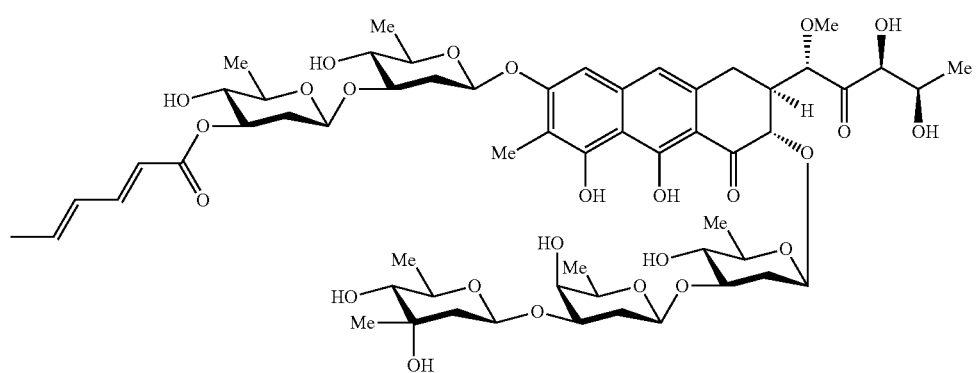
(LVIII)
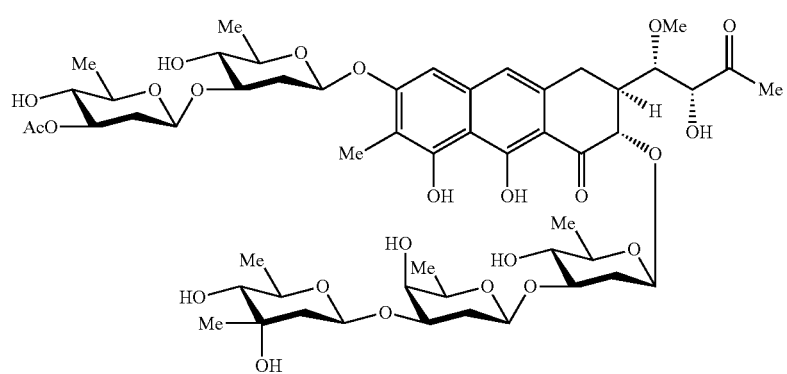
(LXI)

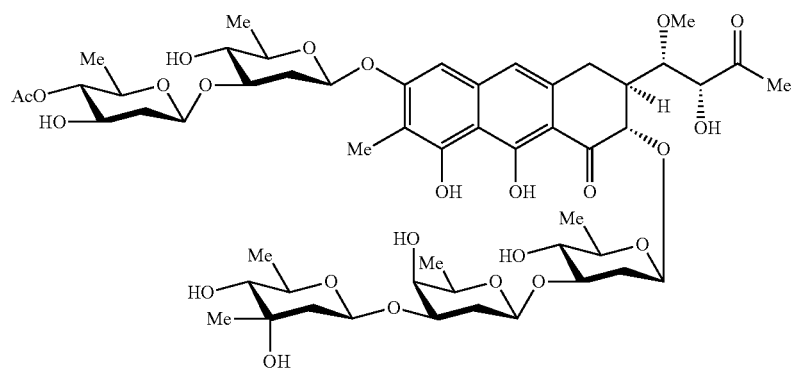
(LXIX)
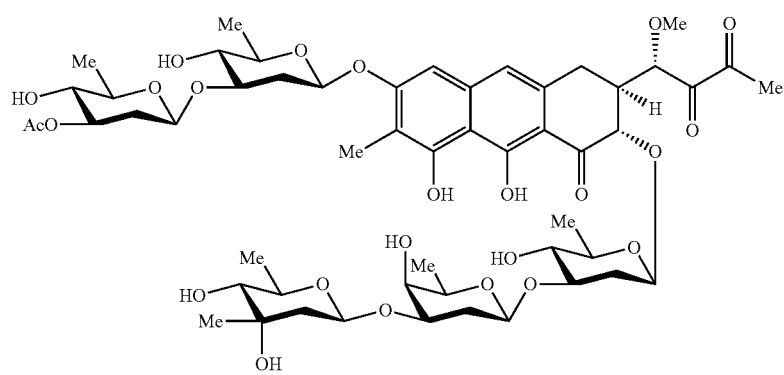
(LXXX)
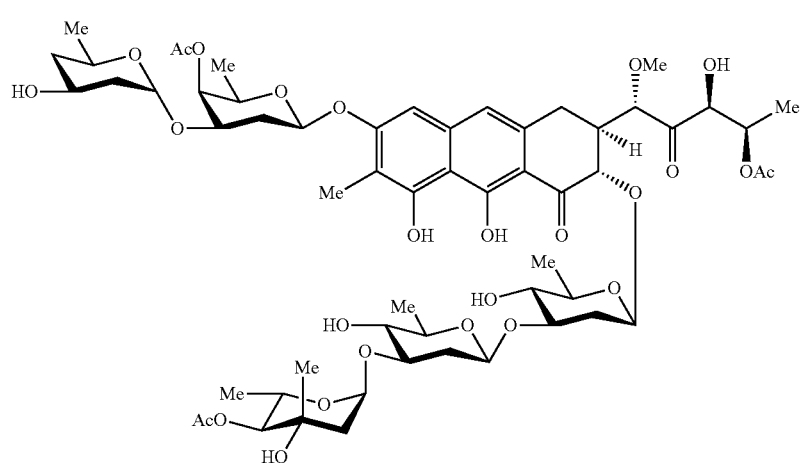
(XCII)
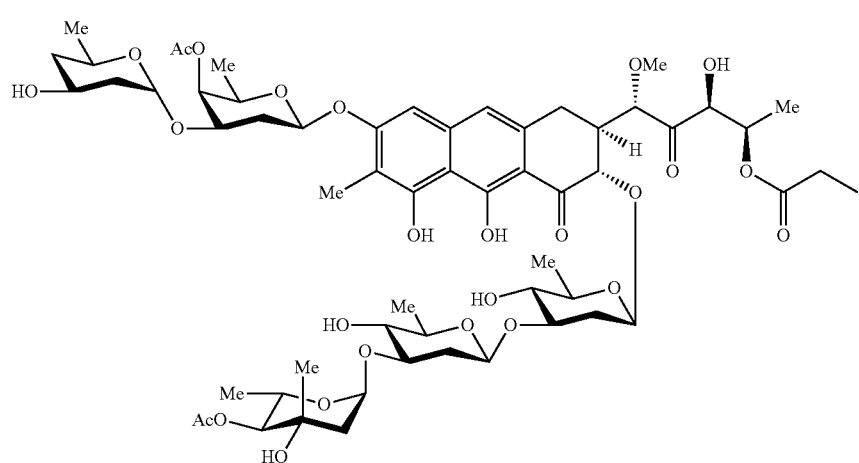
(XCIII)

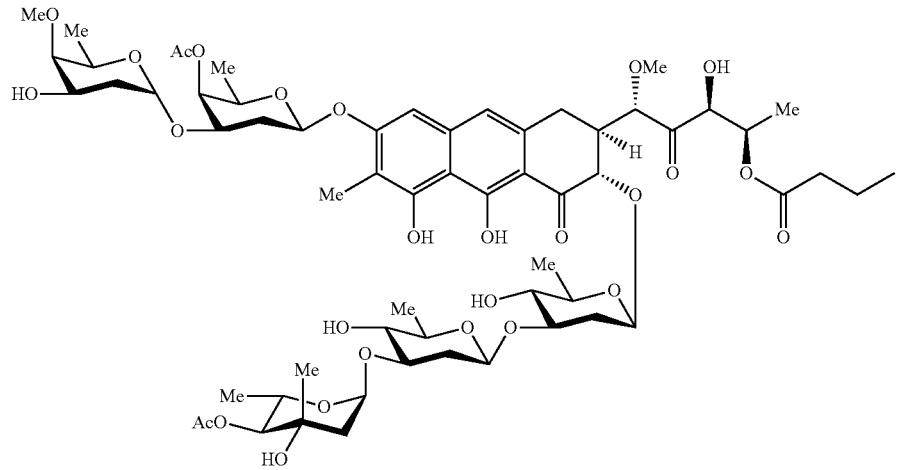

(XCIV)

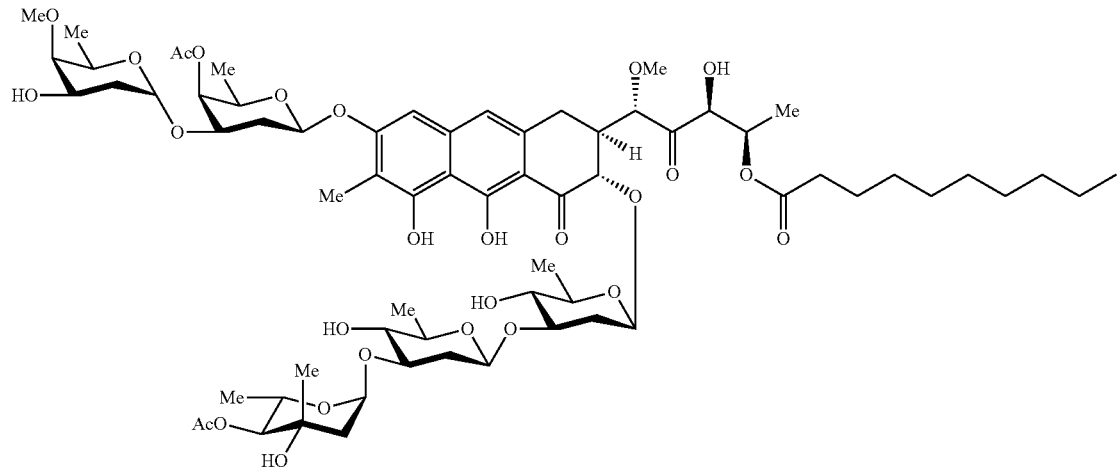

(XCV)

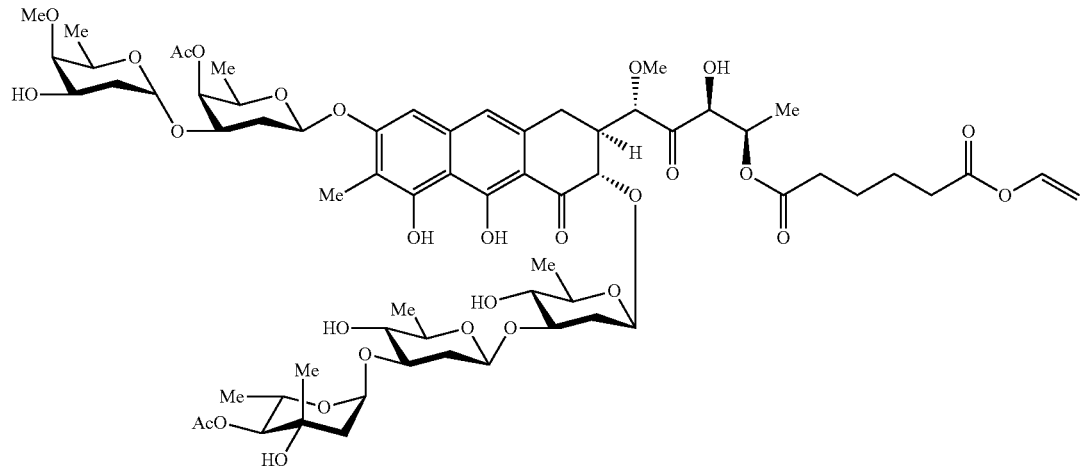

(XCVI)

The compounds of the present invention are inhibitors or tumor growth so they are useful for the treatment of cancer.

Therefore, the pharmaceutical compositions containing an effective amount of compound of formula (I) or a salt or a suitable formulation of this compound are object of the present invention.

It is also the object of the present invention the use of a compound of formula (I) or a salt or a suitable formulation of this compound to inhibit the growth of tumors.

It should be understood that the term 'to inhibit' for the purpose of this invention means to reduce the size, to slow down or to stop. So a compound of this invention can reduce the size, slow down or stop growth of a tumor cell. It should be understood that the term 'growth' for the purpose of this invention means to increase the size, proliferation or both. So a compound of this invention can inhibit the increase of size of a tumor cell and/or stop tumor cells from dividing and increasing the number of tumor cells. A 'tumor cell' is a cell that is part of a neoplasm (new form of growth) that can be cancerous (malignant) or noncancerous (benign). A cancerous tumor cell can invade normal tissues and blood or lymph vessels and produce metastasis in tissues located far from the original tumor. A noncancerous tumor cell can grow and compress normal surrounding tissues but cannot invade normal tissues or blood or lymph vessels and cannot produce metastasis in tissues located far from the original tumor.

It is also the object of the present invention, the use of a compound of formula (I) or a salt or a pharmaceutically acceptable formulation of this compound to treat cancer.

It is also the object of the present invention, the use of a compound of formula (I) or a salt or a pharmaceutically acceptable formulation to manufacture a medicine with anti-tumor activity.

It is also the object of the present invention, the use of a compound of formula (I) or a salt or a pharmaceutically acceptable formulation to manufacture a medicine to treat cancer.

It is also the object of the present invention a method for the treatment of a subject, that can be a human being, diagnosed with cancer and involves the administration of a therapeutically effective amount of a compound of formula (I) or a salt or a pharmaceutically acceptable formulation of this compound.

It should be understood that the term 'subject' can include domesticated animals (for example, cats, dogs et cetera), cattle (for example, cows, horses, pigs, sheep, goats et cetera), laboratory animals (for example, mice, rabbits, guinea pigs et cetera) and birds. Preferably, the subject is a mammal such as a primate and particularly a human.

Generally, the 'effective amount' of a compound is an amount required to obtain the desired effect. For example, the effective amount of a compound of the present invention produces the inhibition of growth of tumor forming cells preventing invasion of normal tissues and blood or lymph vessels and preventing metastasis. Examples of types of cancer that can be treated include, but are not limited to, are lung, colon, ovary, prostate, testicular, melanoma, kidney, breast, central nervous system and leukemia. The term 'acceptable pharmaceutical composition' includes a suitable biological material, meaning that the material can be administered to the subject without causing substantial harmful effects.

The dose or amount of compounds of the invention must be enough to produce the desired effect and should not cause adverse secondary effects such as anaphylactic shock. Generally, the dose will change according to age, condition, gender and stage of the disease in the subject and can be determined by the experts. The dose can be calculated depending on the clinical condition of the subject involved. The dose, regime and administration route can be adjusted. The current dose and dose regime, used for MTM can be used as a guide for dosing the new aureolic acid derivatives (*Cancer Treat. Rep.* 1979, 63, 1835-1838; *Ann. Intern. Med.* 1975, 83, 659-660).

It is also the object of the present invention the use of a compound of formula (I) or a salt or a pharmaceutically acceptable formulation of this compound in the manufacturing of a medicine for the treatment of Paget's disease.

It is also the object of this invention a method for treating a subject, including a human being, diagnosed with Paget's disease consisting of treating such subject with a therapeutically effective amount of the compound of formula (I) or a salt or a pharmaceutically acceptable formulation of this compound. The subject can be a mammal, preferably a human being, and the compound can be administered, among other routes, preferably by parenteral route.

It is also the object of the present invention the use of a compound of formula (I) or a salt or a pharmaceutically acceptable formulation of this compound in the manufacturing of a medicine for the treatment of hypercalcemia.

It is also the object of this invention a method for treating a subject, including a human being, diagnosed with hypercalcemia consisting of treating such subject with a therapeutically effective amount of the compound of formula (I) or a salt or a pharmaceutically acceptable formulation of this compound. The subject can be a mammal, preferably a human being, and the compound can be administered, among other routes, preferably by parenteral route.

It is also the object of the present invention the use of a compound of formula (I) or a salt or a pharmaceutically acceptable formulation of this compound in the manufacturing of a medicine for the treatment of hypercalciuria.

It is also the object of this invention a method for treating a subject, including a human being, diagnosed with hypercalciuria consisting of treating such subject with a therapeutically effective amount of the compound of formula (I) or a salt or a pharmaceutically acceptable formulation of this compound. The subject can be a mammal, preferably a human being, and the compound can be administered, among other routes, preferably by parenteral route.

It is also the object of the present invention the use of a compound of formula (I) or a salt or a pharmaceutically acceptable formulation of this compound in the manufacturing of a medicine for the treatment of neurologic diseases.

It is also the object of this invention a method for treating a subject, including a human being, diagnosed with a neurologic disease consisting of treating such subject with a therapeutically effective amount of the compound of formula (I) or a salt or a pharmaceutically acceptable formulation of this compound. The subject can be a mammal, preferably a human being, and the compound can be administered, among other routes, preferably by parenteral route.

Examples of neurologic diseases that can be treated include, but are not limited to, neurodegenerative diseases such as Parkinson's, Alzheimer's and Huntington's disease.

The compounds of the invention can be useful in biochemical research or cell biology. For example, the compounds can be useful for blocking c-Src expression (and other Sp1 dependent enzymes) in osteoclasts or other types of cells.

Any of the compounds of the invention can be used in therapy as a part of a combination in a pharmaceutically acceptable composition. An expert in this subject can create pharmaceutically acceptable compositions that can be sterile solutions in water, saline solution or buffered solutions with physiological pH. Any of the compounds of the invention can be prepared as a pharmaceutical composition. The pharmaceutical composition can include different agents like carriers, thickening, diluting or buffering agents, preservatives, detergents and others, apart from the compound of the invention. The pharmaceutical compositions can include active ingredients as well such as antimicrobial, anti-inflammatory or anesthetic agents among others.

The compounds of the invention can be administered to the subject in different ways depending on whether a local or systemic treatment is desirable. For example, a compound of the present invention can be administered as an ophthalmic solution to target the eye surface. The compound can be administered to a subject by vaginal, rectal, intranasal or oral route or by inhalation, parenteral route as intradermal, subcutaneous, intramuscular, intraperitoneal, intrarectal, intraarterial, intralymphatic, intravenous, intrathecal and intratracheal. Parenteral administration is generally done by injection. The compounds to be used in injections can be prepared in different ways such as solutions or liquid suspensions, as a solid ready to be dissolved or suspended right before the injection, or as an emulsion. Other forms of parenteral administration use slow or sustained release dosage making possible to keep a constant dose (for example see U.S. Pat. No. 3,710,795). Preparations for parenteral administration include sterile aqueous or nonaqueous solutions, suspensions, and emulsions that can contain buffers or other additives. Examples of nonaqueous solvents are propylene glycol, polyethylene glycol, vegetable oils like olive oil and injectable organic esters like ethyl oleate. Examples of aqueous solvents are water, alcohol:water solutions, emulsions or suspensions including saline solutions and buffered solutions. Examples of parenteral vehicles are sodium chloride solution, Ringer dextrose, sodium chloride:dextrose, etcetera. Other compounds can be included such as preservatives and additives like, for example, antibacterial agents, antioxidants, chelating agents, inert gases and so on. Formulations for topic administration can include cremes, lotions, gels, drops, suppositories, sprays, liquids and powders. It might be necessary or desirable to include conventional pharmaceutical carriers, aqueous based carriers, oil based carriers, powders or thickening agents and so on. Compositions for oral route administration can include powders or granules, suspensions or water solutions, nonaqueous media, capsules, or tablets. It might be desirable to include thickening agents, flavouring agents, diluting agents, emulsifiers, dispersing agents and so on.

For the purpose of the present invention and its description the term derivative of aureolic acid should be understood as a compound covered by general formula (I).

DESCRIPTION OF A PREFERRED EMBODIMENT

The following examples, described in detail, are set forth for better understanding of the present invention and should not limit the scope of the invention.

Example 1

Obtaining the Bacterial Strain *Streptomyces argillaceus* ΔAH-W⁻ (pMP3*BII)

Molecular biology procedures of the present example are conventional in the current state of the art. Plasmid and total DNA isolation, restriction endonuclease digestions, alkaline phosphatase treatment, DNA ligations, etc., were performed according to standard methods previously described by Sambrook et al., 2001 (Molecular Cloning, a Laboratory Manual, 3$^{rd}$ ed, Cold Spring Harbor Laboratory Press, New York) and Kieser et al., 2000 (Practical *Streptomyces* genetics, The John Innes Foundation, Norwich, England). DNA fragments were isolated from agarose gels using the GFX PCR DNA and Gel Band Purification Kit (GE Healthcare). *Escherichia coli* strain DH10B (Invitrogen) was used as general cloning host.

*S. argillaceus* derivative strains described in the present invention were cultured for sporulation on solid A medium (J. Bacteriol., 1998, 180, 4929-4937) at 30° C.; for antibiotic production were grown in liquid R5A medium (J. Bacteriol., 1998, 180, 4929-4937) using an inoculum previously grown in liquid TSB medium (Merck). Introduction of DNA into *Streptomyces* strains was carried out by means of protoplast transformation (Kieser et al, 2000, Practical *Streptomyces* genetics, The John Innes Foundation, Norwich, England). For growth of strains containing antibiotic resistance markers, cultures were supplemented with appropriate antibiotics at the following concentrations: 100 μg/ml ampicillin, 25 μg/ml thiostrepton (solid medium), 5 μg/ml thiostrepton (liquid medium) and 100 μg/ml hygromycin.

Generation of the bacterial strain *Streptomyces argillaceus* ΔAH-W⁻ (pMP3*BII) was carried out in two stages:

1.1. Obtaining the mutant strain *S. argillaceus* ΔAH-W⁻
1.2. Introduction of plasmid pMP3*BII into the strain *S. argillaceus* ΔAH-W⁻

1.1. Obtaining the Mutant Strain *S. argillaceus* ΔAH-W⁻

Characterization of the MTM biosynthesis pathway involved the generation of mutant strains with different inactivated genes of the cluster. One of these strains was *S. argillaceus* ΔAH, a mutant generated by gene replacement in which the genes mtmA and mtmH were inactivated together. MtmA is a fusion protein with a first domain S-adenosylmethionine synthetase and a second domain methylenetetrahydrofolate reductase. MtmH protein is similar to S-adenosylhomocysteine hydrolases (Appl. Microbiol. Biotechnol., 2006, 73, 1-14). These enzymes are related to the biosynthesis of S-adenosylmethionine, a cofactor utilized by methyltransferases involved in the biosynthesis of MTM (J. Biol. Chem., 2000, 275, 3065-3074). However, despite the function previously assigned to these two genes, the mutant *S. argillaceus* ΔAH was not affected in the methylation profile of the accumulated products and production of MTM continued, even at higher levels than the wild type, suggesting a regulatory role of one or both genes in the biosynthesis of MTM (Appl. Microbiol. Biotechnol. 2006, 2006, 73, 1-14). Generation of mutant *S. argillaceus* ΔAH and analysis of MTM production were described in detail in the Thesis: "Biosynthesis of mithramycin by *Streptomyces argillaceus*: characterization of genes involved in methylation of the polyketide structure" (Maria José Fernández Lozano, 1999).

MTM overproducer strain *S. argillaceus* ΔAH was used to inactivate the gene mtmW, which encodes a protein involved in the ketoreduction of the side chain being the final step in MTM biosynthesis. Previous inactivation of mtmW gene in *S. argillaceus* ATCC12956 yielded the mutant strain M7W1, which accumulated new MTM derivatives bearing shorter side chains than MTM, namely 3D-demycarosyl-MTM-SK, MTM-SK, MTM-SDK and MTM-SA (U.S. Pat. No. 7,423, 008 B2; J. Am. Chem Soc 2003, 125, 5745-5753).

Inactivation of the gene mtmW was performed by replacement of the wild type copy in the chromosome of the mutant *S. argillaceus* ΔAH by an in vitro modified copy. For this purpose, a BamHI DNA fragment of 4.5 kb containing the 3' end of mtmV, genes mtmW, mtmGIV and the 5' end of mtmGIII was cloned into the vector pBSKT (J. Bacteriol. 1999, 181, 642-647) previously digested with BamHI, generating the construct pM7W0 (J. Am. Chem Soc 2003, 125, 5745-5753). Then, the hygromycin resistance gene was cloned into the unique BglII restriction site of mtmW (previously blunt-ended by treatment with Klenow fragment of DNA polymerase) obtaining the plasmid pW0Hyg1. In this plasmid, the hygromycin resistance gene is cloned in the same direction of transcription of mtmW. The hygromycin resistance gene was obtained from vector pLHyg (Chem Biol 2004, 11, 87-97) by digestion with EcoRV.

The plasmid pW0Hyg1 was introduced into *S. argillaceus* ΔAH by protoplast transformation according to Keiser et al., 2000 (Practical *Streptomyces* genetics, The John Innes Foundation, Norwich, England). A double crossover is necessary to obtain the replacement of the wild type copy of the gene by the mutated gene. Transformants in which a double crossover event has happened were selected for hygromycin resistance (100 μg/ml) and thiostrepton sensitivity (25 μg/ml). One of the transformants was selected for further characterization, generating the strain S. argillaceus ΔAH-W⁻.

HPLC-MS analysis of extracts from cultures of S. argillaceus ΔAH-W⁻ showed that the ability to produce MTM was lost, accumulating previously characterized derivatives, namely demycarosyl 3D-MTM-SK, MTM-SK, MTM-SDK and MTM-SA.

1.2. Introduction of Plasmid pMP3*BII into the Strain S. argillaceus ΔAH-W⁻

Strain S. argillaceus ΔAH-W⁻ (pMP3*BII) was generated by means of introducing plasmid pMP3*BII into S. argillaceus ΔAH-W⁻ by protoplast transformation. Plasmid pMP3*BII has been previously described, and contains several genes encoding the biosynthesis of nucleoside-diphosphate (NDP)-D-digitoxose (Appl. Environ. Microbiol. 2006, 72, 6644-6652).

Strain Streptomyces argillaceus ΔAH-W⁻ (pMP3*BII) was deposited on the 4th of Jun., 2009 in the Colección Española de Cultivos Tipo (CECT) [Spanish Type Culture Collection], Universidad de Valencia, Campus de Burjassot, 46100 Burjassot (Valencia, Spain) with accession number CECT 7556.

Example 2

Production and Isolation of 3D-demycarosyl-3D-β-D-digitoxosyl-MTM-SK (Formula VII), 3D-demycarosyl-MTM-SDK (Formula VIII), 3D-demycarosyl-3D-β-D-digitoxosyl-MTM-SDK (Formula IX), 3D-demycarosyl-MTM-SA (Formula X), 3D-demycarosyl-3D-β-D-digitoxosyl-MTM-SA (Formula XI)

For the purification of the novel derivatives of MTM-SK, MTM-SDK and MTM-SA, the strain S. argillaceus ΔAH-W⁻ (pMP3*BII) was cultured in solid R5A medium (J. Bacteriol. 1998, 180, 4929-4937) supplemented with thiostrepton (final concentration 25 μg/ml). 150 agar plates were uniformly inoculated with spores and after 10 days of incubation at 30° C., cultures were extracted 6 times with ethyl acetate and extracts were dried under vacuum. Then, the dry extract was dissolved in 50 ml of distilled water and solid-phase extracted (SepPak Vac C18, Waters) (Chem Biol 2002, 9, 519-531). A linear gradient of methanol and water (0 to 100% methanol for 60 min at 10 ml/min) was applied for elution of the retained compounds, collecting fractions every 5 minutes. HPLC analysis of fractions was carried out in an Agilent Technologies 1200 Series chromatographic system, using a reverse phase column (Zorbax Eclipse XDB-C18, RR, 1.8 μm, 4.6×50 mm, Agilent) and acetonitrile (MeCN) and 0.1% trifluoroacetic acid (TFA) in water as mobile phase. Samples were eluted with three linear gradients from 10% to 60% MeCN for 5.70 min, followed by another from 60% to 100% MeCN for 0.5 min and the third gradient from 100% to 10% MeCN for 1.90 min, at flow rate of 2 ml/min. UV absorption maximum of compounds was 278 nm. Fractions containing the desired compounds (from 70% to 100% methanol) were mixed and dried in vacuo. The dry extract, previously dissolved in 10 ml of methanol, was chromatographed in a XBridge Prep C18 column (30×150 mm, Waters) in order to collect peaks of interest using a mixture of MeCN and 0.1% TFA in water (35:65) as mobile phase, at flow of 20 ml/min. All compounds collected were repurified using the same column and mixture of solvents. The obtained fractions were collected on 0.1 M phosphate buffer pH 7 and after purification, samples were diluted four times with water and solid-phase extracted removing the acid of the mobile phase and concentrating the compounds, which were finally lyophilized. Six compounds were isolated, three are new derivatives (FIG. 2): 3D-demycarosyl-3D-β-D-digitoxosyl-MTM-SK (formula VII), 3D-demycarosyl-MTM-SDK (formula VIII), 3D-demycarosyl-3D-β-D-digitoxosyl-MTM-SDK (formula IX) and another three are compounds previously described: 3-demycarosyl-MTM-SK, MTM-SK and MTM-SDK (U.S. Pat. No. 7,423,008 B2, J. Am. Chem. Soc., 2003, 125, 5745-5753; Nucleic Acids Res., 2006, 34, 1721-1734).

Additionally, after extractions with ethyl acetate, cultures were extracted with methanol. The extract was filtered, dried in vacuo and processed as described earlier in this example. Thereby, three compounds were isolated and purified, two are new derivatives (FIG. 3): 3D-demycarosyl-MTM-SA (Formula X), 3D-demycarosyl-3D-β-D-digitoxosyl-MTM-SA (formula XI) and the third compound isolated was MTM-SA, previously described (J. Am. Chem Soc, 2003, 125, 5745-5753).

These new MTM derivatives were initially identified by HPLC analysis by comparing the absorption spectrum and retention time. MS analyses were done in a ZQ4000 mass spectrometer (Waters-Micromass) by electrospray ionization in positive mode, with a capillary voltage of 3 kV and cone voltages of 20 and 100 V. Masses of molecular ions obtained for these new derivatives were: m/z [H⁺] 1042 in the case of 3D-demycarosyl-3D-β-D-digitoxosyl-MTM-SK (formula VII), m/z [H⁺] 910 for 3D-demycarosyl-MTM-SDK (formula VIII), m/z [H⁺] 1040 in the case of 3D-demycarosyl-3D-β-D-digitoxosyl-MTM-SDK (formula IX), m/z [H⁺] 884 for 3D-demycarosyl-MTM-SA (formula X), m/z [H⁺] 1014 in the case of 3D-demycarosyl-3D-β-D-digitoxosyl-MTM-SA (formula XI).

The structures of these new derivatives were elucidated by Nuclear Magnetic Resonance (NMR). Spectra were recorded in acetone-d6 as solvent at 298K using a Bruker Avance 600 spectrometer. Solvent signals were used as internal reference. NMR experiments were processed using the program Topspin 1.3 (Bruker GmbH, Karlsruhe, Germany). All NMR assignments are based on ¹H spectra, COSY and TOCSY. In some cases, additional experiments of ¹³C, DEPT-135, and HSQC were carried out. Data for the compounds of formula (VII) (VIII) (IX), (X) and (XI) are shown in tables 1 to 5.

TABLE 1

NMR of 3D-demycarosyl-3D-β-D-digitoxosyl-MTM-SK (formula VII).
$C_{50}H_{72}O_{23}$
¹H-NMR (acetone-d₆, 600 MHz) and ¹³C-NMR (acetone-d₆, 150 MHz).
Data for compound VII

| Position | ¹H-NMR (δ in ppm, multiplicity, J in Hz) | ¹³C-NMR (δ in ppm) | Multiplicity |
|---|---|---|---|
| 1 | | 202.1 | C |
| 2 | 4.76 d (11.3) | 78.0 | CH |
| 3 | 2.50 (overlapped) | 43.4 | CH |
| 4$_{ax}$ | 3.17 dd (15.7, 3.6) | 29.7 | CH₂ |
| 4$_{eq}$ | 3.00 (overlapped) | | |
| 4a | | 135.2 | C |
| 5 | 6.92 (s) | 101.2 | CH |
| 6 | | 159.7 | C |
| 7 | | 110.1 | C |
| 7-CH₃ | 2.16 (s) | 7.6 | CH₃ |
| 8 | | 152.2 | C |
| 8a | | 107.2 | C |
| 9 | | 164.0 | C |
| 9a | | 107.9 | C |
| 10 | 6.92 (s) | 116.5 | CH |
| 10a | | 138.8 | C |
| 1' | 4.25 dd (3.4, 1.5) | 78.9 | CH |
| 1'-OCH₃ | 3.57 (s) | 59.6 | CH₃ |

TABLE 1-continued

NMR of 3D-demycarosyl-3D-β-D-digitoxosyl-MTM-SK (formula VII). $C_{50}H_{72}O_{23}$
$^1$H-NMR (acetone-$d_6$, 600 MHz) and $^{13}$C-NMR (acetone-$d_6$, 150 MHz). Data for compound VII

| Position | $^1$H-NMR (δ in ppm, multiplicity, J in Hz) | $^{13}$C-NMR (δ in ppm) | Multiplicity |
|---|---|---|---|
| 2' | 4.32 brd (3.4) | 79.1 | CH |
| 3' |  | 209.5 | C |
| 4' | 2.34 (s) | 25.8 | $CH_3$ |
| 1A | 5.42 dd (9.6, 1.9) | 96.7 | CH |
| 2A$_{ax}$ | 1.88 ddd (12.0, 12.0, 9.6) | 37.1 | $CH_2$ |
| 2A$_{eq}$ | 2.50 (overlapped) |  |  |
| 3A | 3.78 ddd (12.0, 8.9, 5.0) | 80.9 | CH |
| 4A | 3.08 t (8.9) | 75.0 | CH |
| 5A | 3.55 (overlapped) | 72.3 | CH |
| 6A | 1.34 d (6.1) | 17.6 | $CH_3$ |
| 1B | 4.77 dd (9.5, 1.7) | 99.5 | CH |
| 2B$_{ax}$ | 1.56 ddd (12.0, 12.0, 9.5) | 39.6 | $CH_2$ |
| 2B$_{eq}$ | 2.20 ddd (12.0, 4.9, 1.7) |  |  |
| 3B | 3.55 (overlapped) | 71.0 | CH |
| 4B | 2.99 t (9.2) | 77.2 | CH |
| 5B | 3.40 dq (9.2, 6.2) | 72.3 | CH |
| 6B | 1.32 d (6.2) | 17.2 | $CH_3$ |
| 1C | 5.13 dd (9.6, 1.6) | 100.4 | CH |
| 2C$_{ax}$ | 1.62 ddd (12.1, 12.0, 9.6) | 37.5 | $CH_2$ |
| 2C$_{eq}$ | 2.50 (overlapped) |  |  |
| 3C | 3.70 (overlapped) | 81.4 | CH |
| 4C | 3.03 t (8.9) | 75.3 | CH |
| 5C | 3.33 dq (8.9, 6.4) | 72.3 | CH |
| 6C | 1.33 d (6.4) | 17.2 | $CH_3$ |
| 1D | 4.70 dd (9.5, 1.5) | 99.8 | CH |
| 2D$_{ax}$ | 1.81 ddd (12.0, 12.0, 9.5) | 32.1 | $CH_2$ |
| 2D$_{eq}$ | 1.96 ddd (12.0, 5.0, 1.5) |  |  |
| 3D | 3.90 ddd (11.9, 5.0, 1.9) | 76.5 | CH |
| 4D | 3.70 (overlapped) | 68.5 | CH |
| 5D | 3.70 (overlapped) | 70.6 | CH |
| 6D | 1.31 d (6.2) | 16.1 | $CH_3$ |
| 1E | 5.03 dd (9.6, 1.9) | 96.9 | CH |
| 2E$_{ax}$ | 1.70 ddd (13.0, 9.6, 2.8) | 38.3 | $CH_2$ |
| 2E$_{eq}$ | 1.92 ddd (13.0, 2.0, 1.9) |  |  |
| 3E | 4.05 brs | 67.8 | CH |
| 4E | 3.20 dd (9.5, 2.9) | 72.8 | CH |
| 5E | 3.70 (overlapped) | 69.6 | CH |
| 6E | 1.23 d (6.2) | 16.1 | $CH_3$ |

TABLE 2

NMR of 3D-demycarosyl-MTM-SDK (formula VIII). $C_{44}H_{60}O_{20}$
$^1$H-NMR (acetone-$d_6$, 600 MHz) and $^{13}$C-NMR (acetone-$d_6$, 150 MHz). Data for compound VIII

| Position | $^1$H-NMR (δ in ppm, multiplicity, J in Hz) | $^{13}$C-NMR (δ in ppm) | Multiplicity |
|---|---|---|---|
| 1 |  | 204.1 | C |
| 2 | 4.76 d (12.1) | 76.9 | CH |
| 3 | 2.74 t (12.1) | 42.3 | C |
| 4$_{ax}$ | 2.95 (overlapped) | 27.3 | $CH_2$ |
| 4$_{eq}$ | 2.64 d (15.5) |  |  |
| 4a |  | 135.5 | C |
| 5 | 6.90 (s) | 100.9 | CH |
| 6 |  | 159.5 | C |
| 7 |  | 110.3 | C |
| 7-$CH_3$ | 2.18 (s) | 7.5 | $CH_3$ |
| 8 |  | 152.4 | C |
| 8a |  | 107.4 | C |
| 9 |  | 164.5 | C |
| 9a |  | 107.9 | C |
| 10 | 6.90 (s) | 116.3 | CH |
| 10a |  | 138.5 | C |
| 1' | 5.07 d (2.0) | 79.6 | CH |
| 1'-$OCH_3$ | 3.45 (s) | 58.4 | $CH_3$ |
| 2' |  | 198.3 | C |
| 3' |  | 198.3 | C |
| 4' | 2.34 (s) | 23.6 | $CH_3$ |

TABLE 2-continued

NMR of 3D-demycarosyl-MTM-SDK (formula VIII). $C_{44}H_{60}O_{20}$
$^1$H-NMR (acetone-$d_6$, 600 MHz) and $^{13}$C-NMR (acetone-$d_6$, 150 MHz). Data for compound VIII

| Position | $^1$H-NMR (δ in ppm, multiplicity, J in Hz) | $^{13}$C-NMR (δ in ppm) | Multiplicity |
|---|---|---|---|
| 1A | 5.39 d (9.7) | 96.8 | CH |
| 2A$_{ax}$ | 1.87 ddd (12.0, 12.0, 9.7) | 37.1 | $CH_2$ |
| 2A$_{eq}$ | 2.48 ddd (12.0, 12.0, 4.9) |  |  |
| 3A | 3.78 ddd (12.0, 9.0, 4.9) | 81.3 | CH |
| 4A | 3.08 t (9.0) | 74.9 | CH |
| 5A | 3.58 (overlapped) | 72.2 | CH |
| 6A | 1.34 d (6.1) | 17.5 | $CH_3$ |
| 1B | 4.76 dd (9.7, 1.7) | 99.5 | CH |
| 2B$_{ax}$ | 1.55 ddd (12.0, 12.0, 9.7) | 39.5 | $CH_2$ |
| 2B$_{eq}$ | 2.21 ddd (12.0, 5.0, 1.7) |  |  |
| 3B | 3.55 ddd (12.0, 8.9, 5.0) | 70.9 | CH |
| 4B | 3.00 t (8.9) | 77.1 | CH |
| 5B | 3.39 dq (8.9, 5.9) | 72.2 | CH |
| 6B | 1.31 d (5.9) | 17.2 | $CH_3$ |
| 1C | 5.10 dd (9.7, 1.6) | 100.6 | CH |
| 2C$_{ax}$ | 1.63 ddd (12.0, 12.0, 9.7) | 37.5 | $CH_2$ |
| 2C$_{eq}$ | 2.53 ddd (12.0, 5.2, 1.6) |  |  |
| 3C | 3.68 (overlapped) | 81.6 | CH |
| 4C | 3.00 t (8.9) | 75.3 | CH |
| 5C | 3.31 dq (8.9, 5.6) | 72.2 | CH |
| 6C | 1.33 d (5.6) | 17.5 | $CH_3$ |
| 1D | 4.69 d (10.0) | 100.0 | CH |
| 2D$_{ax}$ | 1.77 ddd (12.0, 12.0, 10.0) | 34.8 | $CH_2$ |
| 2D$_{eq}$ | 1.92 ddd (12.0, 4.9, 1.9) |  |  |
| 3D | 3.80 ddd (12.0, 4.9, 2.9) | 68.4 | CH |
| 4D | 3.53 (overlapped) | 69.7 | CH |
| 5D | 3.70 brq (6.0) | 70.9 | CH |
| 6D | 1.31 d (6.0) | 16.1 | $CH_3$ |

TABLE 3

NMR of 3D-demycarosyl-3D-β-D-digitoxosyl-MTM-SDK (formula IX). $C_{50}H_{72}O_{23}$
$^1$H-NMR (acetone-$d_6$, 600 MHz) and $^{13}$C-NMR (acetone-$d_6$, 150 MHz). Data for compound IX

| Position | $^1$H-NMR (δ in ppm, multiplicity, J in Hz) | $^{13}$C-NMR (δ in ppm) | Multiplicity |
|---|---|---|---|
| 1 |  | 203.8 | C |
| 2 | 4.78 d (13.1) | 76.8 | CH |
| 3 | 2.74 t (13.1) | 42.4 | C |
| 4$_{ax}$ | 3.05 (overlapped) | 27.3 | $CH_2$ |
| 4$_{eq}$ | 2.65 brd (16.3) |  |  |
| 4a |  | 135.8 | C |
| 5 | 6.92 (s) | 101.2 | CH |
| 6 |  | 159.6 | C |
| 7 |  | 110.2 | C |
| 7-$CH_3$ | 2.15 (s) | 7.5 | $CH_3$ |
| 8 |  | 154.0 | C |
| 8a |  | 107.2 | C |
| 9 |  | 164.0 | C |
| 9a |  | 108.2 | C |
| 10 | 6.92 (s) | 116.4 | CH |
| 10a |  | 138.6 | C |
| 1' | 5.06 d (1.4) | 79.7 | CH |
| 1'-$OCH_3$ | 3.45 (s) | 58.4 | $CH_3$ |
| 2' |  | 198.2 | C |
| 3' |  | 198.3 | C |
| 4' | 2.37 (s) | 23.7 | $CH_3$ |
| 1A | 5.38 d (9.2) | 96.8 | CH |
| 2A$_{ax}$ | 1.89 ddd (12.0, 12.0, 9.2) | 37.1 | $CH_2$ |
| 2A$_{eq}$ | 2.55 dd (12.0, 5.0) |  |  |
| 3A | 3.75 (overlapped) | 80.9 | CH |
| 4A | 3.08 t (9.0) | 75.0 | CH |
| 5A | 3.54 dq (9.0, 6.1) | 72.3 | CH |
| 6A | 1.34 d (6.1) | 17.8 | $CH_3$ |
| 1B | 4.75 dd (9.7, 1.4) | 99.5 | CH |
| 2B$_{ax}$ | 1.55 ddd (12.0, 12.0, 9.7) | 39.6 | $CH_2$ |
| 2B$_{eq}$ | 2.21 ddd (12.0, 4.9, 1.4) |  |  |

TABLE 3-continued

NMR of 3D-demycarosyl-3D-β-D-digitoxosyl-MTM-SDK (formula IX). $C_{50}H_{72}O_{23}$
$^1$H-NMR (acetone-$d_6$, 600 MHz) and $^{13}$C-NMR (acetone-$d_6$, 150 MHz). Data for compound IX

| Position | $^1$H-NMR (δ in ppm, multiplicity, J in Hz) | $^{13}$C-NMR (δ in ppm) | Multiplicity |
|---|---|---|---|
| 3B | 3.58 ddd (12.0, 8.9, 4.9) | 71.0 | CH |
| 4B | 3.00 t (8.9) | 77.2 | CH |
| 5B | 3.40 dq (8.9, 6.2) | 72.3 | CH |
| 6B | 1.31 d (6.2) | 17.2 | $CH_3$ |
| 1C | 5.10 d (9.4) | 100.6 | CH |
| $2C_{ax}$ | 1.62 brq (12.0) | 37.5 | $CH_2$ |
| $2C_{eq}$ | 2.55 dd (12.0, 4.8) | | |
| 3C | 3.70 (overlapped) | 81.5 | CH |
| 4C | 3.00 t (8.9) | 75.3 | CH |
| 5C | 3.32 dq (8.9, 6.2) | 72.3 | CH |
| 6C | 1.32 d (6.2) | 17.5 | $CH_3$ |
| 1D | 4.68 brs | 99.9 | CH |
| $2D_{ax}$ | 1.81 brq (12.0) | 32.1 | $CH_2$ |
| $2D_{eq}$ | 1.95 m | | |
| 3D | 3.90 (overlapped) | 76.5 | CH |
| 4D | 3.76 brs | 68.5 | CH |
| 5D | 3.72 brq (6.2) | 70.6 | CH |
| 6D | 1.31 d (6.2) | 16.1 | $CH_3$ |
| 1E | 5.04 dd (9.6, 1.6) | 96.9 | CH |
| $2E_{ax}$ | 1.70 ddd (12.8, 9.6, 2.8) | 38.3 | $CH_2$ |
| $2E_{eq}$ | 2.01 ddd (12.8, 2.0, 1.6) | | |
| 3E | 4.05 brd (2.8) | 67.8 | CH |
| 4E | 3.20 dd (9.2, 2.3) | 72.8 | CH |
| 5E | 3.75 (overlapped) | 69.6 | CH |
| 6E | 1.24 d (6.1) | 14.7 | $CH_3$ |

TABLE 4

NMR of 3D-demycarosyl-MTM-SA (formula X). $C_{42}H_{58}O_{20}$
$^1$H-NMR (pyridine-$d_5$, 600 MHz). Data for compound X

| Position | $^1$H-NMR (δ in ppm, multiplicity, J in Hz) |
|---|---|
| 1 | |
| 2 | 4.80 (partially overlapped) |
| 3 | 3.12 brt (11.0) |
| $4_{ax}$ | 3.50 (overlapped) |
| $4_{eq}$ | 3.19 brd (15.3) |
| 4a | |
| 5 | 6.95 (s) |
| 6 | |
| 7 | |
| 7-$CH_3$ | 2.50 (s) |
| 8 | |
| 8a | |
| 9 | |
| 9a | |
| 10 | 6.44 (s) |
| 10a | |
| 1' | 4.89 (s) |
| 1'-$OCH_3$ | 3.80 (s) |
| 2' | |
| 1A | 5.54 d (9.5) |
| $2A_{ax}$ | 2.20 brq partially overlapped (11.4) |
| $2A_{eq}$ | 2.61 (overlapped) |
| 3A | 4.15 (overlapped) |
| 4A | 3.55 (overlapped) |
| 5A | 3.90 (overlapped) |
| 6A | 1.66 d (5.9) |
| 1B | 4.99 d (9.5) |
| $2B_{ax}$ | 2.15 (overlapped) |
| $2B_{eq}$ | 2.61 (overlapped) |
| 3B | 4.15 (overlapped) |
| 4B | 3.55 (overlapped) |
| 5B | 3.75 (overlapped) |
| 6B | 1.60 (overlapped) |
| 1C | 5.44 d (9.7) |
| $2C_{ax}$ | 1.91 brq (10.8) |
| $2C_{eq}$ | 2.74 brd (9.7) |

TABLE 4-continued

NMR of 3D-demycarosyl-MTM-SA (formula X). $C_{42}H_{58}O_{20}$
$^1$H-NMR (pyridine-$d_5$, 600 MHz). Data for compound X

| Position | $^1$H-NMR (δ in ppm, multiplicity, J in Hz) |
|---|---|
| 3C | 3.75 (overlapped) |
| 4C | 3.47 t partially overlapped (9.0) |
| 5C | 3.63 dq (9.0 and 6.0) |
| 6C | 1.51 d (6.2) |
| 1D | 4.79 d (11.0) |
| $2D_{ax}$ | 2.15 (overlapped) |
| $2D_{eq}$ | 2.38 brq (10.6) |
| 3D | 4.05 m (signal not resolved) |
| 4D | 3.90 brs (partially overlapped) |
| 5D | 3.55 (overlapped) |
| 6D | 1.60 (overlapped) |

TABLE 5

NMR of 3D-demycarosyl-3D-β-D-digitoxosyl-MTM-SA (formula XI). $C_{48}H_{68}O_{23}$
$^1$H-NMR (pyridine-$d_5$, 600 MHz). Data for compound XI

| Position | $^1$H-NMR (δ in ppm, multiplicity, J in Hz) |
|---|---|
| 1 | |
| 2 | 4.80 (overlapped) |
| 3 | 3.15 brt (13.7) |
| $4_{ax}$ | 3.50 (overlapped) |
| $4_{eq}$ | 3.20 brd (14.8) |
| 4a | |
| 5 | 6.94 (s) |
| 6 | |
| 7 | |
| 7-$CH_3$ | 2.50 (s) |
| 8 | |
| 8a | |
| 9 | |
| 9a | |
| 10 | 6.42 (s) |
| 10a | |
| 1' | 4.91 (s) |
| 1'-$OCH_3$ | 3.81 (s) |
| 2' | |
| 1A | 5.53 brd (7.8) |
| $2A_{ax}$ | 2.16 brq (10.4) |
| $2A_{eq}$ | 2.61 (overlapped) |
| 3A | 4.12 (overlapped) |
| 4A | 3.55 (overlapped) |
| 5A | 3.87 dq (9.0, 6.2) |
| 6A | 1.65 d (5.6) |
| 1B | 4.99 d (9.5) |
| $2B_{ax}$ | 2.14 brq (11.4) |
| $2B_{eq}$ | 2.61 (overlapped) |
| 3B | 4.12 (overlapped) |
| 4B | 3.55 (overlapped) |
| 5B | 3.75 (overlapped) |
| 6B | 1.60 (overlapped) |
| 1C | 5.44 d (9.2) |
| $2C_{ax}$ | 1.93 brq (11.0) |
| $2C_{eq}$ | 2.76 brd (10.1) |
| 3C | 3.75 (overlapped) |
| 4C | 3.55 (overlapped) |
| 5C | 3.55 (overlapped) |
| 6C | 1.48 d (6.1) |
| 1D | 4.79 d (11.3) |
| $2D_{ax}$ | 2.20 (overlapped) |
| $2D_{eq}$ | 2.32 brq (11.4) |
| 3D | 4.10 (overlapped) |
| 4D | 4.06 brs (partially overlapped) |
| 5D | 3.55 (overlapped) |
| 6D | 1.60 (overlapped) |
| 1E | 5.57 d (9.4) |
| $2E_{ax}$ | 2.01 brt (11.5) |
| $2E_{eq}$ | 2.39 brd (11.8) |
| 3E | 4.45 brs |
| 4E | 3.20 brd partially overlapped (10.1) |

TABLE 5-continued

NMR of 3D-demycarosyl-3D-β-D-digitoxosyl-MTM-SA (formula XI).
$C_{48}H_{68}O_{23}$
$^1$H-NMR (pyridine-$d_5$, 600 MHz). Data for compound XI

| Position | $^1$H-NMR (δ in ppm, multiplicity, J in Hz) |
|---|---|
| 5E | 4.39 dq (9.0, 6.5) |
| 6E | 1.60 (overlapped) |

Example 3

Bioconversion of MTM Using *Streptomyces griseus* ssp. *griseus* C10GIV

To isolate new acetylated derivatives of MTM a bioconversion experiment was carried out using *S. griseus* ssp. *griseus* C10GIV incubated in the presence of MTM (50 µg/ml used as substrate) and CRM (2 µg/ml used as inducer of acetyltransferase CmmA) (*Appl. Environ. Microbiol.* 2006. 72, 167-177; *Mol. Microbiol.* 2004, 53, 903-915). The recombinant strain was cultured in R5A medium using a two-step method as described previously (*J. Bacteriol.* 1998, 180, 4929-4937). Production was carried out using five 2 liters Erlenmeyer flasks containing 400 ml of medium per flask. The cultures were incubated for five days at 250 rpm and 30° C. The cultures were spun down at 4000 rpm for 20 min, the cell pellet was discarded and the supernatant was filtered through a Celite filter plate. A second filtration step was carried out using a 1 µm MiniProfile cartridge (Pall). The filtrate was extracted on solid phase (SepPack Vac C18, Waters) (*Chem. Biol.* 2002, 9, 519-531) and the retained compounds were eluted with a linear gradient of methanol and water (0-100% methanol in 60 min at 10 ml/min) and fractions were collected every 5 minutes. Fractions were analyzed by HPLC using the equipment and conditions described in example 2. Fractions containing compounds of interest (fractions 70%-90% methanol) were pooled and dried down on a rotavapor. The dried extract was dissolved in 5 ml methanol and passed through an XBridge Prep C18 column (30×150 mm, Waters) using acetonitrile and 0.1% trifluoroacetic acid in water (45:55) as mobile phase, the flow rate was 20 ml/min. The compounds of interest were collected on 0.1M phosphate buffer pH 7.0 and diluted four times with water before desalting and concentration using solid phase extraction. The resulting compounds were lyophilized. Using this method, two new compounds were isolated.

These new derivatives were initially identified by HPLC analysis comparing the absorption spectra and retention times (FIG. 4). To determine the mass of these compounds, MS analysis was carried out using a ZQ4000 mass spectrometer with electrospray ionization in positive mode at 3 kV capillary voltage and cone voltage of 20 and 100V. The masses for the obtained molecular ions of the new derivatives were m/z [H$^+$] 1128 for compound of formula XII corresponding to a monoacetylated MTM and m/z [H$^+$] 1170 for compound of formula XIII corresponding to a diacetylated MTM.

Structure elucidation of the new derivatives was carried out by NMR. Table 6 shows the data obtained for compound of formula (XII).

TABLE 6

NMR of 4E-acetyl-MTM (formula XII) $C_{54}H_{78}O_{25}$
$^1$H-NMR (acetone-$d_6$, 600 MHz) and $^{13}$C-NMR (acetone-$d_6$, 150 MHz).
Data for compound XII

| Position | $^1$H-NMR (δ in ppm, multiplicity, J in Hz) | $^{13}$C-NMR (δ in ppm) | Multiplicity |
|---|---|---|---|
| 1 | | 205.0 | C |
| 2 | 4.83 d (11.6) | 76.5 | CH |
| 3 | 2.85 (overlapped) | 42.5 | CH |
| 4$_{ax}$ | 3.00 (overlapped) | 29.6 | CH$_2$ |
| 4$_{eq}$ | 2.70 dd (16.1, 3.3) | | |
| 4a | | 136.4 | C |
| 5 | 6.93 (s) | 101.4 | CH |
| 6 | | 159.6 | C |
| 7 | | 110.4 | C |
| 7-CH$_3$ | 2.17 (s) | 7.5 | CH$_3$ |
| 8 | | 152.0 | C |
| 8a | | 107.0 | C |
| 9 | | 164.2 | C |
| 9a | | 107.5 | C |
| 10 | 6.90 (s) | 116.7 | CH |
| 10a | | 138.8 | C |
| 1' | 4.86 brd (3.0) | 81.6 | CH |
| 1'-OCH$_3$ | 3.46 (s) | 58.3 | CH$_3$ |
| 2' | | 210.9 | C |
| 3' | 4.30 (overlapped) | 78.8 | CH |
| 4' | 4.30 (overlapped) | 68.0 | CH |
| 5' | 1.30 (overlapped) | 19.2 | CH$_3$ |
| 1A | 5.42 dd (9.2, 1.8) | 96.7 | CH |
| 2A$_{ax}$ | 1.87 brq partially overlapped (10.0) | 37.1 | CH$_2$ |
| 2A$_{eq}$ | 2.47 ddd (12.0, 5.0, 1.8) | | |
| 3A | 3.80 (overlapped) | 80.9 | CH |
| 4A | 3.08 t (8.7) | 75.0 | CH |
| 5A | 3.55 dq (9.1, 6.1) | 72.2 | CH |
| 6A | 1.30 (overlapped) | 17.2 | CH$_3$ |
| 1B | 4.76 dd (9.8, 1.9) | 99.5 | CH |
| 2B$_{ax}$ | 1.55 (overlapped) | 39.6 | CH$_2$ |
| 2B$_{eq}$ | 2.20 ddd (11.8, 5.0, 1.9) | | |
| 3B | 3.60 (complex signal) | 71.0 | CH |
| 4B | 3.00 (complex signal) | 77.2 | CH |
| 5B | 3.39 dq (9.2, 6.2) | 72.2 | CH |
| 6B | 1.30 (overlapped) | 17.5 | CH$_3$ |
| 1C | 5.14 dd (9.6, 1.5) | 100.5 | CH |
| 2C$_{ax}$ | 1.60 (overlapped) | 37.6 | CH$_2$ |
| 2C$_{eq}$ | 2.55 ddd (12.0, 5.0, 1.5) | | |
| 3C | 3.70 (overlapped) | 81.5 | CH |
| 4C | 3.00 (overlapped) | 75.3 | CH |
| 5C | 3.33 dq (8.8, 5.8) | 72.2 | CH |
| 6C | 1.30 (overlapped) | 17.6 | CH$_3$ |
| 1D | 4.73 dd (9.8, 2.0) | 99.9 | CH |
| 2D$_{ax}$ | 1.82 ddd (12.0, 12.0, 9.8) | 32.0 | CH$_2$ |
| 2D$_{eq}$ | 1.95 (complex signal) | | |
| 3D | 3.94 brs (partially overlapped) | 76.5 | CH |
| 4D | 3.75 complex signal (overlapped) | 68.5 | CH |
| 5D | 3.73 brq partially overlapped (6.4) | 70.6 | CH |
| 6D | 1.30 (overlapped) | 16.1 | CH$_3$ |
| 1E | 5.06 dd (9.7, 2.0) | 97.6 | CH |
| 2E$_{ax}$ | 1.60 (overlapped) | 44.2 | CH$_2$ |
| 2E$_{eq}$ | 1.91 dd (13.0, 2.0) | | |
| 3E | | 69.9 | C |
| 3E-CH$_3$ | 1.14 (s) | 26.4 | CH$_3$ |
| 4E | 4.50 d (9.7) | 77.4 | CH |
| 4E-CH$_3$ | 2.10 s (overlapped) | 19.8 | CH$_3$ |
| 4E-CO | | 170.0 | C |
| 5E | 3.96 dq (9.2, 6.2) | 68.2 | CH |
| 6E | 1.12 d (6.2) | 17.2 | CH$_3$ |

Example 4

Bioconversion of MTM-SK Using *Streptomyces griseus* ssp. *griseus* C10GIV

To isolate new acetylated derivatives of MTM-SK a bioconversion experiment was carried out using *S. griseus* ssp. *griseus* C10GIV incubated in the presence of MTM-SK (50

μg/ml used as substrate) and CRM (2 μg/ml used as inducer of acetyltransferase CmmA) (*Appl. Environ. Microbiol.* 2006. 72, 167-177; *Mol. Microbiol.* 2004, 53, 903-915). The recombinant strain was cultured in R5A medium using a two-step method as described previously (*J. Bacteriol.* 1998, 180, 4929-4937). Production was carried out using five 2 liters Erlenmeyer flasks containing 400 ml of medium per flask. The cultures were incubated for five days at 250 rpm and 30° C. The cultures were spun down at 4000 rpm for 20 min, the cell pellet was discarded and the supernatant was filtered through a Celite filter plate. A second filtration step was carried out using a 1 μm MiniProfile cartridge (Pall). The filtrate was extracted on solid phase (SepPack Vac C18, Waters) (*Chem. Biol.* 2002, 9, 519-531) and the retained compounds were eluted with a linear gradient of methanol and water (0-100% methanol in 60 min at 10 ml/min) and fractions were collected every 5 minutes. Fractions were analyzed by HPLC using the equipment and conditions described in example 2. Fractions containing compounds of interest (fractions 70%-90% methanol) were pooled and dried down on a rotavapor. The dried extract was dissolved in 5 ml methanol and passed through an XBridge Prep C18 column (30× 150 mm, Waters) using acetonitrile and 0.1% trifluoroacetic acid in water (45:55) as mobile phase, the flow rate was 20 ml/min. The compounds of interest were collected on 0.1M phosphate buffer pH 7.0 and diluted four times with water before desalting and concentration using solid phase extraction. The resulting compounds were lyophilized. Using this method, two new compounds were isolated.

These new derivatives were initially identified by HPLC analysis comparing the absorption spectra and retention times (FIG. 5). To determine the mass of these compounds, MS analysis was carried out using a ZQ4000 mass spectrometer with electrospray ionization in positive mode at 3 kV capillary voltage and cone voltage of 20 and 100V. The masses for the obtained molecular ions of the new derivatives were m/z [H⁺] 1098 for compound of formula XIV corresponding to a monoacetylated MTM-SK and m/z [H⁺] 1140 for compound of formula XV corresponding to a diacetylated MTM-SK.

Structure elucidation of the new derivatives was carried out by NMR. Table 7 shows the data obtained for compound of formula (XIV).

TABLE 7

NMR of 4D-acetyl-MTM-SK (formula XIV) $C_{53}H_{76}O_{24}$
$^1$H-NMR (acetone-$d_6$, 600 MHz) and $^{13}$C-NMR (acetone-$d_6$, 150 MHz).
Data for compound XIV

| Position | $^1$H-NMR (δ in ppm, multiplicity, J in Hz) | $^{13}$C-NMR (δ in ppm) | Multiplicity |
|---|---|---|---|
| 1 | | 203.1 | C |
| 2 | 4.75 (overlapped) | 76.5 | CH |
| 3 | 2.50 (overlapped) | 43.4 | CH |
| 4$_{ax}$ | 3.17 brd (15.0) | 29.6 | CH$_2$ |
| 4$_{eq}$ | 3.00 (overlapped) | | |
| 4a | | 136.6 | C |
| 5 | 6.92 (s) | 101.3 | CH |
| 6 | | 159.5 | C |
| 7 | | 110.6 | C |
| 7-CH$_3$ | 2.15 (s) | 7.5 | CH$_3$ |
| 8 | | 154.2 | C |
| 8a | | 107.8 | C |
| 9 | | 165.3 | C |
| 9a | | 108.3 | C |
| 10 | 6.92 (s) | 116.6 | CH |
| 10a | | 138.7 | C |
| 1' | 4.26 (overlapped) | 78.9 | CH |
| 1'-OCH$_3$ | 3.57 (s) | 59.6 | CH$_3$ |
| 2' | 4.31 d (3.7) | 79.1 | C |

TABLE 7-continued

NMR of 4D-acetyl-MTM-SK (formula XIV) $C_{53}H_{76}O_{24}$
$^1$H-NMR (acetone-$d_6$, 600 MHz) and $^{13}$C-NMR (acetone-$d_6$, 150 MHz).
Data for compound XIV

| Position | $^1$H-NMR (δ in ppm, multiplicity, J in Hz) | $^{13}$C-NMR (δ in ppm) | Multiplicity |
|---|---|---|---|
| 3' | | 209.5 | C |
| 4' | 2.34 (s) | 25.8 | CH |
| 1A | 5.42 d (9.0) | 96.3 | CH |
| 2A$_{ax}$ | 1.90 brq (10.4) | 37.1 | CH$_2$ |
| 2A$_{eq}$ | 2.50 (overlapped) | | |
| 3A | 3.80 ddd (12.1, 8.8, 5.2) | 80.9 | CH |
| 4A | 3.09 t (8.8) | 75.0 | CH |
| 5A | 3.60 (overlapped) | 72.3 (overlapped) | CH |
| 6A | 1.34 d (overlapped) | 17.8 | CH$_3$ |
| 1B | 4.76 dd (9.7, 1.5) | 99.5 | CH |
| 2B$_{ax}$ | 1.57 ddd (12.0, 12.0, 9.7) | 39.6 | CH$_2$ |
| 2B$_{eq}$ | 2.20 ddd (12.0, 4.9, 1.5) | | |
| 3B | 3.55 (overlapped) | 71.0 | CH |
| 4B | 3.01 t (8.9) | 77.2 | CH |
| 5B | 3.40 dq (9.0, 6.2) | 72.3 (overlapped) | CH |
| 6B | 1.31 d (6.1) | 17.5 | CH$_3$ |
| 1C | 5.15 overlapped (with 4D) | 100.4 | CH |
| 2C$_{ax}$ | 1.65 (overlapped) | 37.5 | CH$_2$ |
| 2C$_{eq}$ | 2.53 dd (12.0, 4.9) | | |
| 3C | 3.36 (signal not resolved) | 81.5 | CH |
| 4C | 3.05 t (8.9) | 75.3 | CH |
| 5C | 3.75 (signal not resolved) | 72.3 (overlapped) | CH |
| 6C | 1.34 (overlapped) | 17.6 | CH$_3$ |
| 1D | 4.80 brd (9.2) | 99.7 | CH |
| 2D$_{ax}$ | 1.74 brq (10.6) | 32.7 | CH$_2$ |
| 2D$_{eq}$ | 2.15 (overlapped) | | |
| 3D | 4.15 (overlapped) | 72.3 | CH |
| 4D | 5.10 (overlapped) | 70.6 | CH |
| 4D-CH$_3$ | 2.10 (s) | 20.0 | CH$_3$ |
| 4D-CO | | 169.7 | C |
| 5D | 3.90 (overlapped) | 69.9 | CH |
| 6D | 1.15 d (6.2) | 16.1 | CH$_3$ |
| 1E | 4.93 dd (9.5, 1.7) | 96.6 | CH |
| 2E$_{ax}$ | 1.46 dd (13.3, 9.6) | 43.8 | CH$_2$ |
| 2E$_{eq}$ | 1.84 dd (13.3, 1.8) | | |
| 3E | | 70.3 | C |
| 3E-CH$_3$ | 1.22 (s) | 26.7 | CH$_3$ |
| 4E | 2.92 dd (9.2, 7.7) coupled with 4E-OH | 70.4 | CH |
| 4E-OH | 3.89 d (7.7) | | |
| 5E | 3.60 (overlapped) | 72.3 | CH |
| 6E | 1.22 d (6.2) | 17.2 | CH$_3$ |

Example 5

Bioconversion of
3D-demycarosyl-3D-β-D-digitoxosyl-MTM Using
*Streptomyces griseus* ssp. *griseus* C10GIV To isolate new acetylated derivatives of 3D-demycarosyl-3D-β-D-digitoxosyl-MTM (*J. Nat. Prod.* 2008, 71, 199-207; WO 2008/096028 A1) a bioconversion experiment was carried out using *S. griseus* ssp. *griseus* C10GIV incubated in the presence of 3D-demycarosyl-3D-β-D-digitoxosyl-MTM (15 μg/ml used as substrate) and CRM (2 μg/ml used as inducer of acetyltransferase CmmA) (*Appl. Environ. Microbiol.* 2006. 72, 167-177; *Mol. Microbiol.* 2004, 53, 903-915). The recombinant strain was cultured in R5A medium using a two-step method as described previously (*J. Bacteriol.* 1998, 180, 4929-4937). Production was carried out using five 2 liters Erlenmeyer flasks containing 400 ml of medium per flask. The cultures were incubated for five days at 250 rpm and 30° C. The cultures were spun down at 4000 rpm for 20 min, the cell pellet was discarded and the supernatant was filtered through a Celite filter plate. A second filtration step was carried out using a 1 μm MiniProfile cartridge (Pall). The filtrate was extracted on solid phase (SepPack Vac C18, Waters) (*Chem. Biol.* 2002, 9, 519-531) and the retained compounds were eluted with a linear gradient of methanol and water (0-100% methanol in 60 min at 10 ml/min) and fractions were collected every 5 minutes. Fractions were analyzed by HPLC-MS (ZQ4000 Waters-Micromass) using acetonitrile and 0.1% trifluoroacetic acid in water and a Symmetry C18, 2.1×150 mm reverse phase column (Waters). Samples were eluted with 10% acetonitrile for the first 4 minutes followed by a linear gradient 10-88% acetonitrile for 26 minutes at a flow rate of 0.25 ml/min.

Detection and spectrum analysis was carried out with a photodiode detector and Empower software (Waters). MS analysis was carried out by electrospary ionization in positive mode with a capillary voltage of 3 kV and cone voltages of 20 and 100 V. Fractions containing compounds of interest were pooled (FIG. 6) and dried down. The sample was resuspended in 2 ml of DMSO/Methanol (1:1) and loaded into a SunFire C18 (20×250 mm) column (Waters). The mobile phase was a mixture of acetonitrile and 0.1% TFA in water (45:55) and a flow rate of 7 ml/min. The compounds of interest were re-purified using the same semipreparative column with different solvent ratios for the mobile phase. Compounds of interest were collected on 0.1M phosphate buffer pH 7.0 and diluted four times with water before desalting and concentration using solid phase extraction. The resulting compounds were lyophilized.

Using this method, five new compounds were isolated. The masses for the obtained molecular ions of the new derivatives were m/z [H$^+$] 1114 for compounds of formula XVI, XVII and XVIII corresponding to monoacetylated 3D-demycarosyl-3D-β-D-digitoxosyl-MTM in three different positions, m/z [H$^+$] 1156 for compound of formula XIX corresponding to a diacetylated 3D-demycarosyl-3D-β-D-digitoxosyl-MTM, m/z [H$^+$] 1198 for compound of formula XX corresponding to a triacetylated 3D-demycarosyl-3D-β-D-digitoxosyl-MTM Example 6

Bioconversion of
3D-demycarosyl-3D-β-D-digitoxosyl-MTM-SK
Using *Streptomyces griseus* ssp. *griseus* C10GIV To isolate new acetylated derivatives of MTM-SK a bioconversion experiment was carried out using *S. griseus* ssp. *griseus* C10GIV incubated in the presence of 3D-demycarosyl-3D-β-D-digitoxosyl-MTM-SK (25 μg/ml used as substrate) and CRM (inducer of acetyltransferase CmmA) (*Appl. Environ. Microbiol.* 2006. 72, 167-177; *Mol. Microbiol.* 2004, 53, 903-915). The recombinant strain was cultured in R5A medium using a two-step method as described previously (*J. Bacteriol.* 1998, 180, 4929-4937). Production was carried out using two 2 liters Erlenmeyer flasks containing 400 ml of medium per flask. The cultures were incubated for five days at 250 rpm and 30° C. The cultures were spun down at 4000 rpm for 20 min, the cell pellet was discarded and the supernatant was filtered through a Celite filter plate. A second filtration step was carried out using a 1 μm MiniProfile cartridge (Pall). The filtrate was extracted on solid phase (SepPack Vac C18, Waters) (*Chem. Biol.* 2002, 9, 519-531) and the retained compounds were eluted with a linear gradient of methanol and water (0-100% methanol in 60 min at 10 ml/min) and fractions were collected every 5 minutes. Fractions were analyzed by HPLC using the equipment and conditions described in example 2. Fractions containing compounds of interest (fractions 70%-90% methanol) were pooled and dried down on a rotavapor. The dried extract was dissolved in 5 ml methanol and passed through an XBridge Prep C18 column (30×150 mm, Waters) using acetonitrile and 0.1% trifluoroacetic acid in water (45:55) as mobile phase, the flow rate was 20 ml/min. The compounds of interest were collected on 0.1M phosphate buffer pH 7.0 and diluted four times with water before desalting and concentration using solid phase extraction. The resulting compounds were lyophilized. Using this method, two new compounds were isolated.

These new derivatives were initially identified by HPLC analysis comparing the absorption spectra and retention times (FIG. 7). To determine the mass of these compounds, MS analysis was carried out using a ZQ4000 mass spectrometer with electrospray ionization in positive mode at 3 kV capillary voltage and cone voltage of 20 and 100V. The masses for the obtained molecular ions of the new derivatives were m/z [H$^+$] 1084 for compound of formula XXI corresponding to a monoacetylated 3D-demycarosyl-3D-β-D-digitoxosyl-MTM-SK and m/z [H$^+$] 1126 for compound of formula XXII corresponding to a diacetylated 3D-demycarosyl-3D-β-D-digitoxosyl-MTM-SK.

Example 7

Enzymatic Acylation of MTM Catalyzed by CAL-B
Using Different Acylating Agents

The enzymatic acylations of MTM catalyzed by CAL-B were carried out by incubating a suspension of 150 mg of lipase in a solution of 15 mg of MTM at 45° C. and 250 rpm in 3 ml of the appropriate acylating agent. Eventually, 0.5 ml of THF were added in those cases where MTM showed low solubility in the acylating agent. The conversion of the biotransformation was monitored by HPLC using the same chromatography equipment and identical analytical method to that previously described in the example 2. When the conversion reached a value close to 90%, the enzyme was filtered to vacuum filter plate and abundantly washed with methanol and THF. The filtrate was concentrated under vacuum and the resulting residue, previously dissolved in 5 ml of methanol, was chromatographed on a column XBridge Prep C18 (30×150 mm, Waters), mobile phase mixtures of acetonitrile and 0.1% trifluoroacetic acid in water at a flow rate of 20 ml/min. The peaks of interest were collected on 0.1 M phosphate buffer pH 7, diluted four times with water in order to be desalted and concentrated using solid phase extraction. Finally, the compounds obtained were lyophilized for preservation.

The new acylated derivatives were initially identified by HPLC analysis by comparing the absorption spectrum and retention time (FIG. 8). Next, they were characterized by MS and NMR analysis according to the previous examples.

In the particular case of using vinyl acetate as acylating agent the reaction time was of one day and a conversion of 95% was reached. Three new compounds were identified by HPLC which were purified using a mixture of acetonitrile and 0.1% trifluoroacetic acid in water (45:55) as mobile phase at flow of 20 ml/min. Once isolated the compounds were identified as 4'-acetylmithramycin, 3B-acetylmithramycin and 4',3B-diacetylmithramycin (formula XXIII, XXIV and XXV, respectively).

The final structure elucidation of the new derivatives was performed by NMR. Tables 8 to 10 show the data obtained for the compounds of formula (XXIII) (XXIV) and (XXV).

TABLE 8

NMR of 4'-acetyl-MTM (formula XXIII)
$^1$H-NMR (acetone-$d_6$, 600 MHz) and $^{13}$C-NMR (acetone-$d_6$, 150 MHz).
Data for compound XXIII

| Position | $^1$H-NMR ($\delta$ in ppm, multiplicity, J in Hz) | $^{13}$C-RMN ($\delta$ in ppm) | multiplicity |
|---|---|---|---|
| 1 | | 203.1 | C |
| 2 | 4.75 (overlapped) | 76.6 | CH |
| 3 | 2.80 (overlapped) | 42.0 | CH |
| 4$_{ax}$ | 3.15 (overlapped) | 29.6 | CH$_2$ |
| 4$_{eq}$ | 3.00 (overlapped) | | |
| 4a | | 135.2 | C |
| 5 | 6.91 (s) | 101.3 | CH |
| 6 | | 159.5 | C |
| 7 | | 110.4 | C |
| 7-CH$_3$ | 2.15 (s) | 7.5 | CH$_3$ |
| 8 | | 152.2 | C |
| 8a | | 107.0 | C |
| 9 | | 164.0 | C |
| 9a | | 107.8 | C |
| 10 | 6.91 (s) | 116.4 | CH |
| 10a | | 138.7 | C |
| 1' | 4.86 (brs) | 81.4 | CH |
| 1'-OCH$_3$ | 3.41 (s) | 58.0 | CH$_3$ |
| 2' | | 209.4 | C |
| 3' | 4.47 dd (6.7, 2.9) coupled with OH | 76.3 | CH |
| 4' | 5.29 dq (5.9, 2.9) | 71.0 | CH |
| 4'-CO | | 169.3 | C |
| 4'-CH$_3$ | 2.05 (s) | 19.8 | CH$_3$ |
| 5' | 1.32 (overlapped) | 15.1 | CH$_3$ |
| 1A | 5.41 brd (9.6) | 96.7 | CH |
| 2A$_{ax}$ | 1.85 (overlapped) | 37.1 | CH$_2$ |
| 2A$_{eq}$ | 2.50 (11.7, 5.1, 1.9) | | |
| 3A | 3.78 ddd (11.7, 8.8, 5.1) | 80.9 | CH |
| 4A | 3.07 t (9.0) | 74.9 | CH |
| 5A | 3.53 dq (9.0, 6.1) | 72.3 | CH |
| 6A | 1.32 (overlapped) | 17.9 | CH$_3$ |
| 1B | 4.76 brd (9.7) | 99.5 | CH |
| 2B$_{ax}$ | 1.55 (overlapped) | 39.6 | CH$_2$ |
| 2B$_{eq}$ | 2.18 ddd (11.5, 5.0, 1.5) | | |
| 3B | 3.55 (overlapped) | 71.0 | CH |
| 4B | 3.00 (overlapped) | 77.2 | CH |
| 5B | 3.35 dq partially overlapped (8.9, 6.2) | 72.3 | CH |
| 6B | 1.32 (overlapped) | 17.5 | CH$_3$ |
| 1C | 5.11 brd (9.7) | 100.6 | CH |
| 2C$_{ax}$ | 1.70 (signal not resolved) | 37.4 | CH$_2$ |
| 2C$_{eq}$ | 2.50 ddd (12.0, 4.9, 2.0) | | |
| 3C | 3.50 (overlapped) | 81.6 | CH |
| 4C | 3.00 (overlapped) | 75.2 | CH |
| 5C | 3.30 (signal not resolved) | 72.3 | CH |
| 6C | 1.32 (overlapped) | 17.6 | CH$_3$ |
| 1D | 4.74 brd (9.5) | 99.9 | CH |
| 2D$_{ax}$ | 1.80 (signal not resolved) | 32.1 | CH$_2$ |
| 2D$_{eq}$ | 1.95 (overlapped) | | |
| 3D | 3.85 (signal not resolved) | 76.4 | CH |
| 4D | 3.75 (overlapped) | 68.4 | CH |
| 5D | 3.67 dq (9.0, 6.1) | 70.7 | CH |
| 6D | 1.32 (overlapped) | 16.1 | CH$_3$ |
| 1E | 4.99 brd (9.7) | 97.5 | CH |
| 2E$_{ax}$ | 1.55 (overlapped) | 44.0 | CH$_2$ |
| 2E$_{eq}$ | 1.90 (overlapped) | | |
| 3E | | 70.3 | C |
| 3E-CH$_3$ | 1.24 (s) | 26.6 | CH$_3$ |
| 4E | 3.00 (overlapped) | 76.4 | CH |
| 5E | 3.66 dq (9.0, 6.0) | 70.6 | CH |
| 6E | 1.24 d (6.0) | 17.2 | CH$_3$ |

ESI-MS (XXIII): 463.00, 593.22, 723.33, 867.36, 1127.50

TABLE 9

NRM of 3B-acetyl-MTM (formula XXIV)
$^1$H-NMR (acetone-$d_6$, 600 MHz) and $^{13}$C-NMR (acetone-$d_6$, 150 MHz).
Data for compound XXIV

| Position | $^1$H-NMR ($\delta$ in ppm, multiplicity, J in Hz) | $^{13}$C-NMR ($\delta$ in ppm) | Multiplicity |
|---|---|---|---|
| 1 | | 203.6 | C |
| 2 | 4.85 (overlapped) | 76.5 | CH |
| 3 | 2.80 (overlapped) | 42.5 | CH |
| 4$_{ax}$ | 3.00 (overlapped) | 29.6 | CH$_2$ |
| 4$_{eq}$ | 2.69 (16.6, 3.5) | | |
| 4a | | 136.2 | C |
| 5 | 6.93 (s) | 101.4 | CH |
| 6 | | 159.6 | C |
| 7 | | 110.4 | C |
| 7-CH$_3$ | 2.15 (s) | 7.5 | CH$_3$ |
| 8 | | 152.1 | C |
| 8a | | 107.0 | C |
| 9 | | 164.1 | C |
| 9a | | 107.7 | C |
| 10 | 6.90 (s) | 116.8 | CH |
| 10a | | 138.8 | C |
| 1' | 4.86 dd (3.8, 1.6) | 81.6 | CH |
| 1'-OCH$_3$ | 3.50 (s) | 58.3 | CH$_3$ |
| 2' | | 210.8 | C |
| 3' | 4.29 (overlapped) | 78.8 | CH |
| 4' | 4.29 (overlapped) | 67.9 | CH |
| 5' | 1.32 (overlapped) | 19.2 | CH$_3$ |
| 1A | 5.42 dd (9.7, 1.9) | 96.7 | CH |
| 2A$_{ax}$ | 1.87 ddd (11.8, 11.7, 9.7) | 37.0 | CH$_2$ |
| 2A$_{eq}$ | 2.52 ddd (11.7, 5.2, 1.9) | | |
| 3A | 3.82 ddd (11.8, 8.7, 5.2) | 80.8 | CH |
| 4A | 3.09 t partially overlapped (8.7) | 75.0 | CH |
| 5A | 3.57 dq (9.1, 6.1) | 72.2 | CH |
| 6A | 1.32 (overlapped) | 17.9 | CH$_3$ |
| 1B | 4.85 (overlapped) | 98.7 | CH |
| 2B$_{ax}$ | 1.55 (overlapped) | 36.7 | CH$_2$ |
| 2B$_{eq}$ | 2.29 ddd (11.5, 5.2, 1.8) | | |
| 3B | 4.85 (overlapped) | 73.2 | CH |
| 3B-CH$_3$ | 2.03 (s) | 20.1 | CH$_3$ |
| SB-CO | | 169.9 | C |
| 4B | 3.20 (signal not resolved) | 73.7 | CH |
| 5B | 3.52 dq (9.4, 6.2) | 72.2 | CH |
| 6B | 1.32 (overlapped) | 17.5 | CH$_3$ |
| 1C | 5.14 dd (9.7, 1.6) | 100.5 | CH |
| 2C$_{ax}$ | 1.63 ddd (12.0, 12.0, 9.7) | 37.6 | CH$_2$ |
| 2C$_{eq}$ | 2.50 ddd (12.0, 4.9, 1.6) | | |
| 3C | 3.70 (overlapped) | 81.5 | CH |
| 4C | 3.00 (overlapped) | 75.3 | CH |
| 5C | 3.34 dq (9.1, 6.1) | 72.2 | CH |
| 6C | 1.32 (overlapped) | 17.6 | CH$_3$ |
| 1D | 4.72 dd (9.8, 1.9) | 99.9 | CH |
| 2D$_{ax}$ | 1.82 ddd (12.0, 12.0, 9.8) | 32.1 | CH$_2$ |
| 2D$_{eq}$ | 1.95 (signal not resolved) | | |
| 3D | 3.90 ddd (12.0, 5.0, 3.0) | 76.5 | CH |
| 4D | 3.75 brs | 68.5 | CH |
| 5D | 3.67 brq partially overlapped (6.3) | 70.6 | CH |
| 6D | 1.32 (overlapped) | 16.1 | CH$_3$ |
| 1E | 4.99 dd (9.6, 2.0) | 97.5 | CH |
| 2E$_{ax}$ | 1.55 (overlapped) | 44.0 | CH$_2$ |
| 2E$_{eq}$ | 1.90 dd (13.6, 2.0) | | |
| 3E | | 70.3 | C |
| 3E-CH$_3$ | 1.24 (s) | 26.6 | CH$_3$ |
| 4E | 3.00 (overlapped) | 76.4 | CH |
| 5E | 3.66 dq (9.2, 6.1) | 70.6 | CH |
| 6E | 1.25 d (6.1) | 17.2 | CH$_3$ |

ESI-MS (XXIV): 421.20, 551.14, 723.36, 825.29, 1127.43

TABLE 10

NMR of 4',3B-diacetyl-MTM (formula XXV)
$^1$H-NMR (acetone-$d_6$, 600 MHz) and $^{13}$C-NMR (acetone-$d_6$, 150 MHz).
Data for compound XXV

| Position | $^1$H-NMR ($\delta$ in ppm, multiplicity, J in Hz) | $^{13}$C-RMN ($\delta$ in ppm) | Multiplicity |
|---|---|---|---|
| 1 | | overlapped (205) | C |
| 2 | 4.85 (overlapped) | 76.5 | CH |
| 3 | 2.80 (overlapped) | 42.1 | CH |
| 4$_{ax}$ | 3.10 (overlapped) | 29.4 | CH$_2$ |
| 4$_{eq}$ | 3.00 (overlapped) | | |
| 4a | | 136.1 | C |
| 5 | 6.91 (s) | 101.2 | CH |
| 6 | | 159.2 | C |
| 7 | | 110.4 | C |
| 7-CH$_3$ | 2.14 (s) | 7.4 | CH$_3$ |
| 8 | | 152.3 | C |
| 8a | | 107.1 | C |
| 9 | | 164.1 | C |
| 9a | | 107.4 | C |
| 10 | 6.91 (s) | 116.7 | CH |
| 10a | | 138.5 | C |
| 1' | 4.85 (overlapped) | 81.6 | CH |
| 1'-OCH$_3$ | 3.42 (s) | 58.1 | CH$_3$ |
| 2' | | 209.3 | C |
| 3' | 4.50 d (2.9) | 76.5 | CH |
| 4' | 5.30 dq (6.0, 2.9) | 70.5 | CH |
| 4'-CO | | 169.2 | C |
| 4'-CH$_3$ | 2.05 (s) | 20.1 | CH$_3$ |
| 5' | 1.32 (overlapped) | 15.1 | CH$_3$ |
| 1A | 5.40 m (signal not resolved) | 96.7 | CH |
| 2A$_{ax}$ | 1.95 (overlapped) | 37.4 | CH$_2$ |
| 2A$_{eq}$ | 2.49 m (signal not resolved) | | |
| 3A | 3.80 (signal not resolved) | 80.8 | CH |
| 4A | 3.08 t partially overlapped (8.8) | 75.0 | CH |
| 5A | 3.53 (overlapped) | 72.2 | CH |
| 6A | 1.32 (overlapped) | 17.9 | CH$_3$ |
| 1B | 4.85 (overlapped) | 98.7 | CH |
| 2B$_{ax}$ | 1.60 (overlapped) | 37.0 | CH$_2$ |
| 2B$_{eq}$ | 2.30 ddd (11.8, 5.0, 2.0) | | |
| 3B | 4.85 (overlapped) | 73.2 | CH |
| 3B-CH$_3$ | 1.98 (s) | 20.2 | CH$_3$ |
| 3B-CO | | 169.8 | C |
| 4B | 3.25 m (signal not resolved) | 73.7 | CH |
| 5B | 3.53 (overlapped) | 72.2 | CH |
| 6B | 1.32 (overlapped) | 17.5 | CH$_3$ |
| 1C | 5.11 brd (9.3) | 100.6 | CH |
| 2C$_{ax}$ | 1.63 ddd (12.0, 12.0, 9.3) | 37.6 | CH$_2$ |
| 2C$_{eq}$ | 2.55 m (signal not resolved) | | |
| 3C | 3.70 (overlapped) | 81.5 | CH |
| 4C | 3.05 (overlapped) | 75.3 | CH |
| 5C | 3.30 dq (9.1, 6.1) | 72.2 | CH |
| 6C | 1.32 (overlapped) | 17.6 | CH$_3$ |
| 1D | 4.74 m (signal not resolved) | 99.9 | CH |
| 2D$_{ax}$ | 1.80 ddd (12.0, 12.0, 9.7) | 32.1 | CH$_2$ |
| 2D$_{eq}$ | 2.00 (overlapped) | | |
| 3D | 3.85 m (signal not resolved) | 76.5 | CH |
| 4D | 3.74 brs | 68.4 | CH |
| 5D | 3.70 (overlapped) | 70.6 | CH |
| 6D | 1.32 (overlapped) | 16.1 | CH$_3$ |
| 1E | 5.00 brd (9.2) | 97.6 | CH |
| 2E$_{ax}$ | 1.55 (overlapped) | 44.0 | CH$_2$ |
| 2E$_{eq}$ | 1.90 (overlapped) | | |
| 3E | | 70.3 | C |
| 3E-CH$_3$ | 1.25 (s) | 26.6 | CH$_3$ |
| 4E | 2.97 d (9.1) | 76.4 | CH |
| 5E | 3.68 dq (9.1, 6.1) | 70.5 | CH |
| 6E | 1.24 d (6.1) | 17.2 | CH$_3$ |

ESI-MS (XXV): 463.07, 593.22, 765.43, 867.29, 1169.48

In the particular case of using 2,2,2-trifluoroethyl acetate as acylating agent the reaction time was of 4 days and a conversion of 70% was reached. Three acylated derivatives were identified by HPLC (FIG. 9) and purified using a mixture of acetonitrile and 0.1% trifluoroacetic acid in water (45:55) as mobile phase at a flow of 20 ml/min. The three isolated compounds were found to be identical to those obtained with ethyl acetate (XXIII, XXIV and XXV) but this time the yield was significantly lower.

In the particular case of using vinyl chloroacetate as acylating agent the reaction time was of seven days and a conversion of 60% was reached. Three new compounds were identified by HPLC (FIG. 10) with retention times of 4.21, 4.49 and 4.82 minutes (formulas XXVI, XXVII and XVIII, respectively).

In the particular case of using vinyl propanoate as acylating agent the reaction time was of two days and a conversion of 95% was reached. Two new compounds were identified by HPLC (FIG. 11) and purified using a mixture of acetonitrile and 0.1% trifluoroacetic acid in water (50:50) as mobile phase at a flow of 20 ml/min. Once isolated the compounds were identified as 4'-propanoylmithramycin and 4',3B-dipropanoylmithramycin (formulas XXIX and XXX, respectively).

ESI-MS (XXIX): 477.13, 607.24, 737.22, 881.31, 1141.76
ESI-MS (XXX): 477.06, 607.11, 793.29, 881.31, 1197.51

In the particular case of using vinyl butanoate as acylating agent the reaction time was of four days and a conversion of 95% was reached. Two new compounds were identified by HPLC (FIG. 12) and purified using a mixture of acetonitrile and 0.1% trifluoroacetic acid in water (60:40) as mobile phase at a flow of 20 ml/min. Once isolated the compounds were identified as 4'-butanoylmithramycin and 4',3B-butanoylmithramycin (formulas XXXI and XXXII, respectively).

ESI-MS (XXXI): 491.31, 621.08, 751.17, 895.39, 1155.78, 1172.99
ESI-MS (XXXII): 491.24, 621.22, 820.30, 895.41, 1225.60

In the particular case of using acetonoxime levulinate as acylating agent the reaction time was of seven days and a conversion of 20% was reached. A new compound was identified by HPLC (FIG. 13) with a retention time of 4.00 minutes (formula XXXIII).

In the particular case of using vinyl decanoate as acylating agent the reaction time was seven days and a conversion of 90% was reached. A single acylated derivative was identified by HPLC (FIG. 14) and purified using a mixture of acetonitrile and 0.1% trifluoroacetic acid in water (55:45) as mobile phase at a flow of 20 ml/min. Once isolated the new compound was identified as 4'-decanoylmithramycin (formula XXXIV).

The final structure elucidation of the new derivatives was performed by NMR. Table 11 shows the data obtained for the compound of formula (XXXIV).

TABLE 11

NMR of 4'-decanoyl-MTM (formula XXXIV)
$^1$H-NMR (acetone-$d_6$, 600 MHz). Data for compound XXXIV

| Position | $^1$H-NMR ($\delta$ in ppm, multiplicity, J in Hz) |
|---|---|
| 1 | |
| 2 | 4.75 (overlapped) |
| 3 | 2.82 t (12.0) |
| 4$_{ax}$ | 3.20 (overlapped) |
| 4$_{eq}$ | 3.00 (overlapped) |
| 4a | |
| 5 | 6.88 (s) |
| 6 | |
| 7 | |
| 7-CH$_3$ | 2.15 (s) |
| 8 | |
| 8a | |
| 9 | |
| 9a | |

TABLE 11-continued

NMR of 4'-decanoyl-MTM (formula XXXIV)
$^1$H-NMR (acetone-$d_6$, 600 MHz). Data for compound XXXIV

| Position | $^1$H-NMR ($\delta$ in ppm, multiplicity, J in Hz) |
|---|---|
| 10 | 6.91 (s) |
| 10a | |
| 1' | 4.91 (brs) |
| 1'-OCH$_3$ | 3.40 (s) |
| 2' | |
| 3' | 4.44 d (2.5) |
| 4' | 5.30 dq (5.8, 2.5) |
| 4'-CO | |
| 5' | 1.32 (overlapped) |
| 6'-CO | |
| 7' | 2.10 (overlapped) |
| 8' | 1.46 m (signal not resolved) |
| 9' | 1.30 (overlapped) |
| 10' | 1.30 (overlapped) |
| 11' | 1.30 (overlapped) |
| 12' | 1.30 (overlapped) |
| 13' | 1.30 (overlapped) |
| 14' | 1.30 (overlapped) |
| 15' | 0.89 t (7.1) |
| 1A | 5.40 brd (9.2) |
| 2A$_{ax}$ | 1.90 (overlapped) |
| 2A$_{eq}$ | 2.46 (12.0, 5.1, 1.9) |
| 3A | 3.78 (overlapped) |
| 4A | 3.15 t (9.0) |
| 5A | 3.53 dq (9.0, 6.1) |
| 6A | 1.30 (overlapped) |
| 1B | 4.75 (overlapped) |
| 2B$_{ax}$ | 1.55 (overlapped) |
| 2B$_{eq}$ | 2.20 ddd (11.8, 5.0, 1.5) |
| 3B | 3.55 (12.0, 8.9, 5.0) |
| 4B | 3.00 (overlapped) |
| 5B | 3.50 (overlapped) |
| 6B | 1.30 (overlapped) |
| 1C | 5.10 brd(9.0) |
| 2C$_{ax}$ | 1.70 brq (11.0) |
| 2C$_{eq}$ | 2.53 ddd (12.0, 5.9, 2.0) |
| 3C | 3.55 (overlapped) |
| 4C | 3.00 (overlapped) |
| 5C | 3.25 dq (9.1, 6.0) |
| 6C | 1.30 (overlapped) |
| 1D | 4.75 (overlapped) |
| 2D$_{ax}$ | 1.80 brq (11.0) |
| 2D$_{eq}$ | 1.90 (overlapped) |
| 3D | 3.87 (signal not resolved) |
| 4D | 3.75 brs (partially overlapped) |
| 5D | 3.75 (overlapped) |
| 6D | 1.30 (overlapped) |
| 1E | 5.00 brd (9.4) |
| 2E$_{ax}$ | 1.55 (overlapped) |
| 2E$_{eq}$ | 1.90 (overlapped) |
| 3E | |
| 3E-CH$_3$ | 1.25 (s) |
| 4E | 3.00 (overlapped) |
| 5E | 3.70 (overlapped) |
| 6E | 1.30 (overlapped) |

ESI-MS (XXXIV): 575.22, 705.30, 835.37, 979.37, 1240.76

In the particular case of using vinyl dodecanoate as acylating agent the reaction time was of seven days and a conversion of 70% was reached. A new compound was identified by HPLC (FIG. 15) with a retention time of 6.32 minutes (formula XXXV).

In the particular case of using vinyl benzoate as acylating agent the reaction time was of nine days and a conversion of 90% was reached. A single acylated derivative was identified by HPLC (FIG. 16) and purified using a mixture of acetonitrile and 0.1% trifluoroacetic acid in water (50:50) as mobile phase at a flow of 20 ml/min. Once isolated the new compound was identified as 4'-benzoylmithramycin (formula XXXVI).

The final structure elucidation of the new derivatives was performed by NMR. Table 12 shows the data obtained for the compound of formula (XXXVI).

TABLE 12

NMR of 4'-benzoyl-MTM (formula XXXVI)
$^1$H-NMR (acetone-$d_6$, 600 MHz). Data for compound XXXVI

| Position | $^1$H-NMR ($\delta$ in ppm, multiplicity, J in Hz) |
|---|---|
| 1 | |
| 2 | 4.70 (overlapped) |
| 3 | 2.80 (overlapped) |
| 4$_{ax}$ | 3.10 (overlapped) |
| 4$_{eq}$ | 3.00 (overlapped) |
| 4a | |
| 5 | 6.33 (brs) |
| 6 | |
| 7 | |
| 7-CH$_3$ | 2.15 (s) |
| 8 | |
| 8a | |
| 9 | |
| 9a | |
| 10 | 6.63 (brs) |
| 10a | |
| 1' | 4.85 (brs) |
| 1'-OCH$_3$ | 3.32 (s) |
| 2' | |
| 3' | 4.61 dd (6.5, 2.0) coupled with OH |
| 4' | 5.66 dq (6.4, 2.0) |
| orto (2H) | 7.95 d (7.4) |
| para (1H) | 7.42 t (7.4) |
| meta (2H) | 7.32 t (7.4) |
| 5' | 1.48 d (6.4) |
| 1A | 5.39 brd (9.4) |
| 2A$_{ax}$ | 1.92 (overlapped) |
| 2A$_{eq}$ | 2.48 (12.0, 5.0, 1.9) |
| 3A | 3.80 signal not resolved (overlapped) |
| 4A | 3.09 t (8.8) |
| 5A | 3.54 dq (8.8, 6.1) |
| 6A | 1.32 (overlapped) |
| 1B | 4.77 dd (9.0, 1.8) |
| 2B$_{ax}$ | 1.57 (overlapped) |
| 2B$_{eq}$ | 2.20 ddd (11.5, 5.0, 1.8) |
| 3B | 3.60 (overlapped) |
| 4B | 3.00 (overlapped) |
| 5B | 3.41 dq (9.1, 6.1) |
| 6B | 1.32 (overlapped) |
| 1C | 5.08 brd (9.2) |
| 2C$_{ax}$ | 1.19 brq (10.1) |
| 2C$_{eq}$ | 2.51 ddd (12.0, 4.9, 2.0) |
| 3C | 3.60 (overlapped) |
| 4C | 3.00 (overlapped) |
| 5C | 3.30 (overlapped) |
| 6C | 1.32 (overlapped) |
| 1D | 4.67 (overlapped) |
| 2D$_{ax}$ | 1.80 (signal not resolved) |
| 2D$_{eq}$ | 1.92 (overlapped) |
| 3D | 3.85 signal not resolved (partially overlapped) |
| 4D | 3.74 (brs) |
| 5D | 3.70 (overlapped) |
| 6D | 1.32 (overlapped) |
| 1E | 5.00 brd (8.5) |
| 2E$_{ax}$ | 1.57 (overlapped) |
| 2E$_{eq}$ | 1.92 (overlapped) |
| 3E | |
| 3E-CH$_3$ | 1.24 (s) |
| 4E | 3.00 (overlapped) |
| 5E | 3.70 (overlapped) |
| 6E | 1.22 d (6.0) |

In the particular case of using vinyl crotonate as acylating agent the reaction time was of 7 days and a conversion of 25% was reached. A new compound was identified by HPLC (FIG. 17) with a retention time of 4.18 minutes (formula XXVII).

In the particular case of using diallyl carbonate as acylating agent the reaction time was of seven days and a conversion of 50% was reached. A single acylated derivative was identified by HPLC (FIG. 18) and purified using as a mixture of acetonitrile and 0.1% trifluoroacetic acid in water (50:50) as mobile phase at a flow of 20 ml/min. The isolated new compound was identified as 3B-(prop-2-en-1-yloxycarbonyl)-mithramycin (formula XXXVIII) instead of the expected 3B-allyloxycarbonylmithramycin. The formation of this product may be the result of an isomerization catalyzed by trifluoroacetic acid content in the mobile phase preparative chromatography.

The final structure elucidation of the new derivatives was performed by NMR. Table 13 shows the data obtained for the compound of formula (XXXVIII).

TABLE 13

NMR of 3B-(prop-2-en-1-yloxycarbonyl)-MTM (formula XXXVIII)
$^1$H-NMR (acetone-d$_6$, 600 MHz). Data for compound XXXVIII

| Position | $^1$H-NMR (δ in ppm, multiplicity, J in Hz) |
|---|---|
| 1 | |
| 2 | 4.70 (signal not resolved) |
| 3 | 2.85 (overlapped) |
| 4$_{ax}$ | 3.02 brd (15.0) |
| 4$_{eq}$ | 2.75 brd (15.0) |
| 4a | |
| 5 | 6.90 (s) |
| 6 | |
| 7 | |
| 7-CH$_3$ | 2.10 (s) |
| 8 | |
| 8a | |
| 9 | |
| 9a | |
| 10 | 6.90 (s) |
| 10a | |
| 1' | 4.85 (overlapped) |
| 1'-OCH$_3$ | 3.46 (s) |
| 2' | |
| 3' | 4.30 (overlapped) |
| 4' | 4.30 (overlapped) |
| 5' | 1.32 (overlapped) |
| 1A | 5.40 brd (signal not resolved) |
| 2A$_{ax}$ | 1.90 (overlapped) |
| 2A$_{eq}$ | 2.50 brd (signal not resolved) |
| 3A | 3.85 (overlapped) |
| 4A | 3.08 t (8.7) |
| 5A | 3.55 (overlapped) |
| 6A | 1.32 (overlapped) |
| 1B | 4.85 (overlapped) |
| 2B$_{ax}$ | 1.60 (overlapped) |
| 2B$_{eq}$ | 2.31 ddd (11.5, 5.0, 2.0) |
| 3B | 4.85 (overlapped) |
| 3B-1 | 5.88 dd (15.2, 1.0) |
| 3B-2 | 6.99 dq (15.2, 6.5) |
| 3B-3 | 2.00 (overlapped) |
| 3B-CO | |
| 4B | 3.30 (overlapped) |
| 5B | 3.55 (overlapped) |
| 6B | 1.32 (overlapped) |
| 1C | 5.14 brd (9.1) |
| 2C$_{ax}$ | 1.60 (overlapped) |
| 2C$_{eq}$ | 2.55 ddd (12.0, 5.0, 1.8) |
| 3C | 3.70 (overlapped) |
| 4C | 3.00 (overlapped) |
| 5C | 3.30 (overlapped) |
| 6C | 1.32 (overlapped) |
| 1D | 4.70 brd (9.2) |
| 2D$_{ax}$ | 1.75 ddd (12.0, 12.0, 10.0) |
| 2D$_{eq}$ | 1.85 (signal not resolved) |
| 3D | 3.90 (overlapped with OH) |
| 4D | 3.75 brs |
| 5D | 3.70 (overlapped) |
| 6D | 1.32 (overlapped) |
| 1E | 4.98 dd (9.6, 2.0) |
| 2E$_{ax}$ | 1.60 (overlapped) |
| 2E$_{eq}$ | 1.90 (overlapped) |
| 3E | |
| 3E-CH$_3$ | 1.24 (s) |

TABLE 13-continued

NMR of 3B-(prop-2-en-1-yloxycarbonyl)-MTM (formula XXXVIII)
$^1$H-NMR (acetone-d$_6$, 600 MHz). Data for compound XXXVIII

| Position | $^1$H-NMR (δ in ppm, multiplicity, J in Hz) |
|---|---|
| 4E | 3.00 (overlapped) |
| 5E | 3.67 dq (9.0, 6.1) |
| 6E | 1.25 d (6.4) |

In the particular case of using the mixed carbonate of allyl and oxime as acylating agent the reaction time was of seven days and a conversion of 10% was reached. A single acylated derivative was identified by (FIG. 19) and purified using a mixture of acetonitrile and 0.1% trifluoroacetic acid in water (50:50) as mobile phase at a flow of 20 ml/min. The isolated compound was found to be identical to that obtained with diallyl carbonate acylating as agent (XXXVIII).

In the particular case of using vinylene carbonate as acylating agent the reaction time was of 3 days and a conversion higher than 95% was reached. Two new compounds were identified by HPLC (FIG. 20) with retention times of 3.11 and 4.13 minutes (formulas XXXIX and XL).

Example 8

Enzymatic Acylation of 4'-Benzoyl-MTM Catalyzed by CAL-B Using Vinyl Acetate as Acylating Agent The enzymatic acetylation of 4'-benzoyl-MTM was carried out analogously as discussed in the example X1 employing for this particular case the lipase B from Candida antarctica (CAL-B) as biocatalyst and vinyl acetate as acylating agent. The reaction time was of four days and a conversion higher than 95% was reached. A single acylated derivative was detected by HPLC (FIG. 21) and identified by mass spectrometry as 3B-acetyl-4'-benzoylmithramycin (formula XLI).

Example 9

Enzymatic Acylation of MTM Catalyzed by CAL-A Using Different Acylating Agents

The enzymatic acylations of MTM catalyzed by CAL-A were carried out analogously as discussed in the example 7 but using in this case the lipase A from Candida antarctica (CAL-A) as biocatalyst. Similarly, the protocol of purification, isolation and characterization of the new acylated derivatives is identical to that described above in the example 7.

In the particular case of using vinyl acetate as acylating agent the reaction time was of one day and a conversion of 95% was reached. Two acylated derivatives were identified by HPLC (FIG. 22) which were purified using a mixture of acetonitrile and 0.1% trifluoroacetic acid in water (50:50) as mobile phase at a flow of 20 ml/min. The isolated compounds were identified as 4'-acetylmithramycin and 3B-acetylmithramycin according to the previous example (formulas XXIII and XXIV).

In the particular case of using vinyl chloroacetate as acylating agent the reaction time was of four days and a conversion of 10% was reached. Two acylated derivatives were identified by HPLC (FIG. 23) with retention times of 4.54 and 4.88 minutes (formulas XLII and XLIII, respectively).

In the particular case of using vinyl propanoate as acylating agent the reaction time was of two days and a conversion of 95% was reached. Two new compounds were identified by HPLC (FIG. 24) which were purified using a mixture of acetonitrile and 0.1% trifluoroacetic acid in water (50:50) as mobile phase at a flow of 20 ml/min. The isolated compounds were identified as 3B-propanoylmithramycin and 4B-propanoylmithramycin (formulas XLIV and XLV, respectively).

ESI-MS (XLIV): 421.21, 551.31, 737.31, 825.29, 1141.51
ESI-MS (XLV): 421.15, 551.20, 737.32, 825.30, 1141.51

In the particular case of using vinyl butanoate as acylating agent the reaction time was of three days and a conversion of 95% was reached. Two new compounds were identified by HPLC (FIG. 25) which were purified using a mixture of acetonitrile and 0.1% trifluoroacetic acid in water (60:40) as mobile phase at a flow of 20 ml/min. The isolated compounds were identified as 3B-butanoylmithramycin and 4B-butanoylmithramycin (formulas XLVI and XLVII, respectively).

ESI-MS (XLVI): 421.07, 551.17, 750.90, 825.36, 1155.30
ESI-MS (XLVII): 421.34, 551.11, 751.57, 825.43, 1155.77

In the particular case of using vinyl decanoate as acylating agent the reaction time was of four days and a conversion of 90% was reached. Two new compounds were identified by HPLC (FIG. 26) which were purified using a mixture of acetonitrile and 0.1% trifluoroacetic acid in water (55:45) as mobile phase at a flow of 20 ml/min. The isolated compounds were identified as 3B-decanoylmithramycin and 4B-decanoylmithramycin (formulas XLVIII and XLIX, respectively).

ESI-MS (XLVIII): 421.14, 551.24, 825.36, 835.39, 1239.52
ESI-MS (XLIX): 421.14, 551.31, 825.36, 835.46, 1239.74

In the particular case of using vinyl benzoate as acylating agent the reaction time was of five days and a conversion of 20% was reached. A new compound was identified by HPLC (FIG. 27) with a retention time of 5.65 minutes (formula L).

In the particular case of using vinyl crotonate as acylating agent the reaction time was of five days and a conversion of 90% was reached. A unique acylated derivative was identified by HPLC (FIG. 28) which was purified using a mixture of acetonitrile and 0.1% trifluoroacetic acid in water (50:50) as mobile phase at a flow of 20 ml/min. The isolated compound was identified as 3B-crotonylmithramycin (formula LI).

ESI-MS (LI): 421.14, 551.17, 749.29, 825.36, 1153.46

In the particular case of using diallyl carbonate as acylating agent the reaction time was of seven days and a conversion of 95% was reached. A unique acylated derivative was identified by HPLC (FIG. 28) which was identical to that obtained in the previous example employing CAL-B as biocatalyst (XXXVIII).

In the particular case of using succinic anhydride as acylating agent the reaction time was of three days and a conversion of 85% was reached. Five new derivatives were identified by HPLC (FIG. 30) which were purified using a mixture of acetonitrile and 0.1% trifluoroacetic acid in water (45:55) as mobile phase at a flow of 20 ml/min. The isolated compounds were identified as 4'-(3-carboxypropanoyl)mithramycin, 4B-(3-carboxypropanoyl)mithramycin, 4',4B-di-(3-carboxypropanoyl)mithramycin, 3B-(3-carboxypropanoyl)mithramycin and 4',3B-di-(3-carboxypropanoyl)mithramycin (formulas LII, III, LIV, LV y LVI, respectively).

ESI-MS (LII): 521.11, 651.09, 925.16, 1185.23
ESI-MS (LIII): 421.31, 551.29, 781.26, 825.30, 1185.42
ESI-MS (LIV): 521.24, 651.32, 881.26, 925.46, 1285.54
ESI-MS (LV): 421.18, 551.23, 781.13, 825.43, 1185.60
ESI-MS (LVI): 521.27, 651.24, 881.40, 925.49, 1285.71

In the particular case of using vinyl adipate as acylating agent the reaction time was of six days and a conversion of 90% was reached. A unique acylated derivative was identified by HPLC (FIG. 31) which was purified using a mixture of acetonitrile and 0.1% trifluoroacetic acid in water (55:45) as mobile phase at a flow of 20 ml/min. The isolated compound was identified as 3B-(5-vinyloxycarbonyl)-pentanoylmithramycin (formula LVII).

ESI-MS (LVII): 421.25, 551.36, 825.41, 835.12, 1239.92

In the particular case of using vinyl sorbate as acylating agent the reaction time was of four days and a conversion of 90% was reached. A unique acylated derivative was identified by HPLC (FIG. 32) which was purified using a mixture of acetonitrile and 0.1% trifluoroacetic acid in water (55:45) as mobile phase at a flow of 20 ml/min. The isolated compound was identified as 3B-(2,4-hexadienoyl)-mithramycin (formula LVIII).

ESI-MS (LVIII): 421.32, 551.31, 775.63, 825.63, 1180.13

In the particular case of using vinylene carbonate as acylating agent the reaction time was of three days and a conversion of 90% was reached. Two new compounds were identified by HPLC (FIG. 33) with retention times of 3.13 and 4.36 minutes (formulas LIX and LX, respectively).

Example 10

Enzymatic Acylation of MTM-SK Catalyzed by CAL-B Using Different Acylating Agents The enzymatic acylations of MTM-SK catalyzed by CAL-B were carried out analogously as discussed in the example 7 but using in this case MTM-SK as starting material. Similarly, the protocol of purification, isolation and characterization of the new acylated derivatives is identical to that described above in the example 7.

In the particular case of using vinyl acetate as acylating agent the reaction time was of three days and a conversion of 90% was reached. A unique acylated derivative was identified by HPLC (FIG. 34) which was purified using a mixture of acetonitrile and 0.1% trifluoroacetic acid in water (50:50) as mobile phase at a flow of 20 ml/min. The new isolated compound was identified as 3B-acetylmithramycin SK (formula LXI).

Structure elucidation of the new derivatives was carried out by NMR. Table 14 shows the data obtained for compound of formula (LXI).

TABLE 14

NMR of 3B-acetyl-MTM-SK (formula LXI)
$^1$H-NMR (acetone-$d_6$, 600 MHz). Data for compound LXI

| Position | $^1$H-NMR (δ in ppm, multiplicity, J in Hz) |
|---|---|
| 1 | |
| 2 | 4.76 d (10.9) |
| 3 | 2.50 (overlapped) |
| $4_{ax}$ | 3.17 dd (16.4, 3.1) |
| $4_{eq}$ | 3.00 (overlapped) |
| 4a | |
| 5 | 6.92 (s) |
| 6 | |
| 7 | |
| 7-CH$_3$ | 2.16 (s) |
| 8 | |
| 8a | |

TABLE 14-continued

NMR of 3B-acetyl-MTM-SK (formula LXI)
$^1$H-NMR (acetone-$d_6$, 600 MHz). Data for compound LXI

| Position | $^1$H-NMR ($\delta$ in ppm, multiplicity, J in Hz) |
|---|---|
| 9 | |
| 9a | |
| 10 | 6.92 (s) |
| 10a | |
| 1' | 4.25 brd, partially overlapped (3.2) |
| 1'-OCH$_3$ | 3.56 (s) |
| 2' | 4.32 d partially overlapped (3.2) |
| 3' | |
| 4' | 2.34 (s) |
| 1A | 5.44 d (8.9) |
| 2A$_{ax}$ | 1.90 (overlapped) |
| 2A$_{eq}$ | 2.50 (overlapped) |
| 3A | 3.84 ddd (11.8, 8.9, 5.2) |
| 4A | 3.10 t (8.9) |
| 5A | 3.59 dq (8.9, 6.1) |
| 6A | 1.32 d (overlapped) |
| 1B | 4.87 dd (9.7, 1.9) |
| 2B$_{ax}$ | 1.55 (overlapped) |
| 2B$_{eq}$ | 2.29 ddd (12.1, 5.2, 1.9) |
| 3B | 4.83 ddd (11.8, 9.2, 5.2) |
| 3B-Ac | 2.05 (s) |
| 4B | 3.27 dt (9.1, 5.0) coupled with 4B-OH |
| 4B-OH | 4.58 d (5.0) |
| 5B | 3.53 dq (9.1, 6.1) |
| 6B | 1.32 d (overlapped) |
| 1C | 5.14 dd (9.5, 1.9) |
| 2C$_{ax}$ | 1.60 ddd (overlapped) |
| 2C$_{eq}$ | 2.50 (overlapped) |
| 3C | 3.70 (overlapped) |
| 4C | 3.02 t (9.1) |
| 5C | 3.33 dq (8.9, 6.3) |
| 6C | 1.32 d (overlapped) |
| 1D | 4.67 brd (partially overlapped) |
| 2D$_{ax}$ | 1.79 brq (10.2) |
| 2D$_{eq}$ | 1.90 brd (overlapped) |
| 3D | 3.90 (overlapped) |
| 4D | 3.70 (overlapped) |
| 5D | 3.74 brs |
| 6D | 1.32 d (overlapped) |
| 1E | 4.98 dd (9.5, 1.9) |
| 2E$_{ax}$ | 1.60 (overlapped) |
| 2E$_{eq}$ | 1.90 dd (13.5, 2.0) |
| 3E | |
| 3E-CH$_3$ | 1.24 (s) |
| 4E | 2.97 dd (9.2, 7.8) coupled with 4E-OH |
| 4E-OH | 3.90 d partially overlapped (7.8) |
| 5E | 3.65 dq (9.0, 6.2) |
| 6E | 1.24 d (6.2) |

In the particular case of using vinyl chloroacetate as acylating agent the reaction time was of five days and a conversion of 40% was reached. Two acylated derivatives were identified by HPLC (FIG. 35) with retention times of 4.72 and 5.05 minutes (formulas LXII and LXIII, respectively).

In the particular case of using vinyl propanoate as acylating agent the reaction time was of seven days and a conversion of 80% was reached. Two acylated derivatives were identified by HPLC (FIG. 36) with retention times of 5.12 and 6.07 minutes (formulas XLIV and LXV, respectively).

In the particular case of using vinyl butanoate as acylating agent the reaction time was of five days and a conversion of 50% was reached. Two acylated derivatives were identified by HPLC (FIG. 37) with retention times of 4.96 and 5.55 minutes (formulas LXVI and LXVII, respectively).

In the particular case of using diallyl carbonate as acylating agent the reaction time was of five days and a conversion of 60% was reached. A new compound was identified by HPLC (FIG. 38) with retention time of 5.30 minutes (formula LXVIII).

Example 11

Enzymatic Acylation of MTM-SK Catalyzed by CAL-A Using Different Acylating Agents The enzymatic acylations of MTM-SK catalyzed by CAL-A were carried out analogously as discussed in the example 7 but using in this case mithramycin SK as starting material and CAL-A as biocatalyst. Similarly, the protocol of purification, isolation and characterization of the new acylated derivatives is identical to that described above in the example 7.

In the particular case of using vinyl acetate as acylating agent the reaction time was of two days and a conversion of 90% was reached. Two new acylated derivatives were identified by HPLC (FIG. 39) which was purified using a mixture of acetonitrile and 0.1% trifluoroacetic acid in water (50:50) as mobile phase at a flow of 20 ml/min. The isolated compounds were identified as 3B-acetylmithramycin SK (formula LXI, identified in the previous example) and 4B-acetylmithramycin SK (formula LXIX).
ESI-MS (LXIX): 391.10, 521.22, 693.22, 795.33, 1098.50

In the particular case of using vinyl chloroacetate as acylating agent the reaction time was of two days and a conversion of 6% was reached. Two acylated derivatives were identified by HPLC (FIG. 40) with retention times of 4.75 and 5.08 minutes (formulas LXX and LXXI, respectively).

In the particular case of using vinyl decanoate as acylating agent the reaction time was of five days and a conversion of 70% was reached. Two new compounds were identified by HPLC (FIG. 41) with retention times of 6.64 and 6.86 minutes (formulas LXXII and LXXIII, respectively).

In the particular case of using vinyl benzoate as acylating agent the reaction time was of five days and a conversion of 15% was reached. A new compound was identified by HPLC (FIG. 42) with a retention times of 5.96 minutes (formula LXXIV).

In the particular case of using vinyl crotonate as acylating agent the reaction time was of five days and a conversion of 75% was reached. A new compound was identified by HPLC (FIG. 43) with a retention time of 5.46 minute (formulas LXXV).

In the particular case of using diallyl carbonate as acylating agent the reaction time was of five days and a conversion of 75% was reached. A new compound was identified by HPLC (FIG. 44) with retention time of 5.41 minutes (formula LXVI).

In the particular case of using succinic anhydride as acylating agent the reaction time was of two days and a conversion of 90% was reached. Three new compounds were identified by HPLC (FIG. 41) with retention times of 4.17, 4.34 and 4.51 minutes (formulas LXXVII, LXXVIII and LXXIX, respectively).

Example 12

Enzymatic Acylation of MTM-SDK Catalyzed by CAL-B Using Different Acylating Agents The enzymatic acylations of MTM-SDK catalyzed by CAL-B were carried out analogously as discussed in the example 7 but using in this case mithramycin SDK as starting material. Similarly, the protocol of purification, isolation and characterization of the new acylated derivatives is identical to that described above in the example 7.

In the particular case of using vinyl acetate as acylating agent the reaction time was of three days and a conversion of 90% was reached. A unique acylated derivative was identified by HPLC (FIG. 46) which was purified using a mixture of acetonitrile and 0.1% trifluoroacetic acid in water (60:40) as mobile phase at a flow of 20 ml/min. The new isolated compound was identified as 3B-acetylmithramycin SDK (formula LXXX).

Structure elucidation of the new derivatives was carried out by NMR. Table 15 shows the data obtained for compound of formula (LXXX).

TABLE 15

NMR of 3B-acetyl-MTM-SDK (formula LXXX)
$^1$H-NMR (acetone-$d_6$, 600 MHz). Data for compound LXXX

| Position | $^1$H-NMR ($\delta$ in ppm, multiplicity, J in Hz) |
|---|---|
| 1 | |
| 2 | 4.78 brd (11.5) |
| 3 | 2.75 (signal not resolved) |
| $4_{ax}$ | 3.03 brd (14.8) |
| $4_{eq}$ | 2.64 brd (14.8) |
| 4a | |
| 5 | 6.87 (s) |
| 6 | |
| 7 | |
| 7-CH$_3$ | 2.10 (s) |
| 8 | |
| 8a | |
| 9 | |
| 9a | |
| 10 | 6.87 (s) |
| 10a | |
| 1' | 5.06 brs |
| 1'-OCH$_3$ | 3.45 (s) |
| 2' | |
| 3' | |
| 4' | 2.37 (s) |
| 1A | 5.40 d (9.1) |
| 2A$_{ax}$ | 1.90 (overlapped) |
| 2A$_{eq}$ | 2.50 dd (12.0, 5.0) |
| 3A | 3.83 ddd (11.9, 8.9, 5.0) |
| 4A | 3.09 t (8.8) |
| 5A | 3.55 dq partially overlapped (8.9, 6.2) |
| 6A | 1.32 d (overlapped) |
| 1B | 4.85 (overlapped) |
| 2B$_{ax}$ | 1.60 (overlapped) |
| 2B$_{eq}$ | 2.28 ddd (12.0, 5.0, 1.8) |
| 3B | 4.82 ddd (11.8, 9.2, 5.2) |
| 3B-Ac | 2.10 (s) |
| 4B | 3.26 dt (9.1, 4.0) coupled with 4B-OH |
| 4B-OH | 4.50 d (4.0) |
| 5B | 3.52 dq partially overlapped (9.0, 6.2) |
| 6B | 1.32 d (overlapped) |
| 1C | 5.10 brd (9.1) |
| 2C$_{ax}$ | 1.60 (overlapped) |
| 2C$_{eq}$ | 2.55 (12.0, 5.2, 1.9) |
| 3C | 3.70 (overlapped) |
| 4C | 3.00 (overlapped) |
| 5C | 3.30 (signal not resolved) |
| 6C | 1.32 d (overlapped) |
| 1D | 4.85 (overlapped) |
| 2D$_{ax}$ | 1.79 brq (10.0) |
| 2D$_{eq}$ | 1.90 (overlapped) |
| 3D | 3.90 (overlapped) |
| 4D | 3.70 (overlapped) |
| 5D | 3.74 brs |
| 6D | 1.32 d (overlapped) |
| 1E | 4.99 dd (9.5, 1.8) |
| 2E$_{ax}$ | 1.60 (overlapped) |
| 2E$_{eq}$ | 1.91 dd (13.4, 1.8) |
| 3E | |
| 3E-CH$_3$ | 1.24 (s) |
| 4E | 3.00 (overlapped) |

TABLE 15-continued

NMR of 3B-acetyl-MTM-SDK (formula LXXX)
$^1$H-NMR (acetone-$d_6$, 600 MHz). Data for compound LXXX

| Position | $^1$H-NMR ($\delta$ in ppm, multiplicity, J in Hz) |
|---|---|
| 4E-OH | 4.00 d (7.8) coupled with 4E |
| 5E | 3.67 dq (9.1, 6.0) |
| 6E | 1.24 d (6.0) |

In the particular case of using vinyl chloroacetate as acylating agent the reaction time was of five days and a conversion of 35% was reached. A new compound was identified by HPLC (FIG. 47) with a retention time of 5.48 minutes (formula LXXXI).

In the particular case of using vinyl propanoate as acylating agent the reaction time was of seven days and a conversion of 65% was reached. A new compound was identified by HPLC (FIG. 48) with a retention time of 5.56 minutes (formula LXXXII).

In the particular case of using vinyl butanoate as acylating agent the reaction time was of five days and a conversion of 25% was reached. Two acylated derivatives were identified by HPLC (FIG. 49) with retention times of 5.46 and 5.99 minutes (formulas LXXXIII and LXXXIV, respectively).

In the particular case of using diallyl carbonate as acylating agent the reaction time was of five days and a conversion of 25% was reached. A new compound was identified by HPLC (FIG. 50) with a retention time of 5.72 minutes (formula LXXXV).

Example 13

Enzymatic Acylation of MTM-SDK Catalyzed by CAL-A Using Different Acylating Agents The enzymatic acylations of MTM-SDK catalyzed by CAL-A were carried out analogously as discussed in the example 7 but using in this case mithramycin SDK as starting material and CAL-A as biocatalyst. Similarly, the protocol of purification, isolation and characterization of the new acylated derivatives is identical to that described above in the example 7.

In the particular case of using vinyl acetate as acylating agent the reaction time was of three days and a conversion of 90% was reached. Two new derivatives were identified by HPLC (FIG. 51) with retention times of 4.89 (formula LXXXVI) and 5.21 minutes (described in the previous example with the formula LXXX).

In the particular case of using vinyl chloroacetate as acylating agent the reaction time was of two days and a conversion of 3% was reached. A new compound was identified by HPLC (FIG. 52) with a retention time of 5.45 (formula LXXXVII).

In the particular case of using vinyl crotonate as acylating agent the reaction time was of four days and a conversion of 75% was reached. A new compound was identified by HPLC (FIG. 53) with a retention time of 5.78 (formula LXXXVIII).

In the particular case of using diallyl carbonate as acylating agent the reaction time was of four days and a conversion of 80% was reached. A new compound was identified by HPLC (FIG. 54) with a retention time of 5.73 (formula LXXXIX).

In the particular case of using succinic anhydride as acylating agent the reaction time was of two days and a conversion of 60% was reached. Two new derivatives were identified by HPLC (FIG. 55) with retention times of 4.59 (formula LXXXVI) and 4.77 minutes (formulas XC and XCI, respectively).

Example 14

Enzymatic Acylation of CRM Catalyzed by CAL-B Using Different Acylating Agents The enzymatic acylations of CRM catalyzed by CAL-B were carried out analogously as discussed in the example 7 but using in this case chromomycin $A_3$ as starting material. Similarly, the protocol of purification, isolation and characterization of the new acylated derivatives is identical to that described above in the example 7.

In the particular case of using vinyl acetate as acylating agent the reaction time was of two days and a conversion of 95% was reached. A unique acylated derivative was identified by HPLC (FIG. 56) which was purified using a mixture of acetonitrile and 0.1% trifluoroacetic acid in water (50:50) as mobile phase at a flow of 20 ml/min. The new isolated compound was identified as 4'-acetylchromomycin $A_3$ (formula XCII).

Structure elucidation of the new derivatives was carried out by NMR. Table 16 shows the data obtained for compound of formula (XCII).

TABLE 16

NMR of 4'-acetyl-CRM (formula XCII)
$^1$H-NMR (acetone-$d_6$, 600 MHz) and $^{13}$C-NMR (acetone-$d_6$, 150 MHz).
Data for compound XCII

| Position | $^1$H-NMR ($\delta$ in ppm, multiplicity, J in Hz) | $^{13}$C-NMR ($\delta$ in ppm) | Multiplicity |
|---|---|---|---|
| 1 | | 203.5 | C |
| 2 | 4.80 (overlapped) | 76.6 | CH |
| 3 | 2.80 (overlapped) | 42.0 | CH |
| $4_{ax}$ | 2.55 (overlapped) | 26.9 | $CH_2$ |
| $4_{eq}$ | 3.00 (overlapped) | | |
| 4a | | 136.8 | C |
| 5 | 6.88 (s) | 101.4 | CH |
| 6 | | 159.3 | C |
| 7 | | 110.5 | C |
| 7-$CH_3$ | 2.20 (s) | 7.5 | $CH_3$ |
| 8 | | 155.7 | C |
| 8a | | 108.1 | C |
| 9 | | 164.9 | C |
| 9a | | 107.8 | C |
| 10 | 6.92 (s) | 117.1 | CH |
| 10a | | 138.5 | C |
| 1' | 4.86 (brs) | 81.3 | CH |
| 1'-$OCH_3$ | 3.54 (s) | 61.0 | $CH_3$ |
| 2' | | 211.3 | C |
| 3' | 4.48 dd (6.5, 2.9) coupled with OH | 76.3 | CH |
| 4' | 5.30 dq (6.0, 2.9) | 70.7 | CH |
| 4'-CO | | 169.2 | C |
| 4'-$CH_3$ | 1.95 (s) | 19.9 | $CH_3$ |
| 5' | 1.33 (overlapped) | 15.2 | $CH_3$ |
| 1A | 5.47 brd (9.5) | 97.1 | CH |
| $2A_{ax}$ | 2.10 (overlapped) | 32.9 | $CH_2$ |
| $2A_{eq}$ | 2.15 (overlapped) | | |
| 3A | 4.17 ddd (11.0, 6.2, 3.0) | 69.7 | CH |
| 4A | 5.21 d (2.5) | 67.5 | CH |
| 4A-$CH_3$ | 2.15 (s) | 20.1 | $CH_3$ |
| 4A-CO | | 170.0 | C |
| 5A | 4.04 brq (6.4) | 69.4 | CH |
| 6A | 1.20 d (6.2) | 16.1 | $CH_3$ |
| 1B | 5.07 (solapado) | 95.0 | CH |
| $2B_{ax}$ | 1.59 dd (12.3, 4.7) | 32.2 | $CH_2$ |
| $2B_{eq}$ | 1.90 m (complex signal) | | |
| 3B | 3.99 ddd (10.8, 6.0, 3.0) | 66.1 | CH |
| 4B | 3.22 brs | 81.6 | CH |
| 4B-$OCH_3$ | 3.41 (s) | 58.0 | $CH_3$ |

TABLE 16-continued

NMR of 4'-acetyl-CRM (formula XCII)
$^1$H-NMR (acetone-$d_6$, 600 MHz) and $^{13}$C-NMR (acetone-$d_6$, 150 MHz).
Data for compound XCII

| Position | $^1$H-NMR ($\delta$ in ppm, multiplicity, J in Hz) | $^{13}$C-NMR ($\delta$ in ppm) | Multiplicity |
|---|---|---|---|
| 5B | 3.93 brq (6.8) | 67.0 | CH |
| 6B | 1.21 d (6.1) | 17.2 | $CH_3$ |
| 1C | 5.13 brd (9.7) | 100.6 | CH |
| $2C_{ax}$ | 1.70 brq (10.4) | 37.4 | $CH_2$ |
| $2C_{eq}$ | 2.60 (overlapped)) | | |
| 3C | 3.72 (overlapped) | 81.6 | CH |
| 4C | 3.00 (overlapped) | 75.2 | CH |
| 5C | 3.33 dq (9.0, 6.2) | 72.1 | CH |
| 6C | 1.31 d (6.2) | 17.4 | $CH_3$ |
| 1D | 4.80 (overlapped) | 99.4 | CH |
| $2D_{ax}$ | 1.49 brq (10.7) | 36.5 | $CH_2$ |
| $2D_{eq}$ | 2.40 brd (10.3) | | |
| 3D | 3.72 (overlapped) | 76.1 | CH |
| 4D | 3.13 m (signal not resolved) | 74.9 | CH |
| 5D | 3.45 dq (9.0, 6.1) | 72.4 | CH |
| 6D | 1.33 (overlapped) | 17.6 | $CH_3$ |
| 1E | 5.07 (overlapped) | 94.4 | CH |
| $2E_{ax}$ | 2.00 (overlapped) | 43.9 | $CH_2$ |
| $2E_{eq}$ | 2.10 (overlapped) | | |
| 3E | | 70.6 | C |
| 3E-$CH_3$ | 1.42 (s) | 22.7 | $CH_3$ |
| 4E | 4.68 d (9.7) | 79.3 | CH |
| 4E-$CH_3$ | 2.05 (s) | 20.3 | $CH_3$ |
| 4E-CO | | 170.3 | C |
| 5E | 4.11 dq (10.0, 6.2) | 65.7 | CH |
| 6E | 1.12 d (6.2) | 16.6 | $CH_3$ |

In the particular case of using vinyl propanoate as acylating agent the reaction time was of two days and a conversion of 90% was reached. A new compound was identified by HPLC (FIG. 57) with a retention time of 3.62 minutes (formula XCIII)

In the particular case of using vinyl butanoate as acylating agent the reaction time was of two days and a conversion of 90% was reached. A unique acylated derivative was identified by HPLC (FIG. 58) which was purified using a mixture of acetonitrile and 0.1% trifluoroacetic acid in water (60:40) as mobile phase at a flow of 20 ml/min. The new isolated compound was identified as 4'-butanoylchromomycin $A_3$ (formula XCIV).

Structure elucidation of the new derivatives was carried out by NMR. Table 17 shows the data obtained for compound of formula (XCIV).

TABLE 17

NMR of 4'-butanoyl-CRM (formula XCIV)
$^1$H-NMR (acetone-$d_6$, 600 MHz) and $^{13}$C-NMR (acetone-$d_6$, 150 MHz).
Data for compound XCIV

| Position | $^1$H-NMR ($\delta$ in ppm, multiplicity, J in Hz) | $^{13}$C-NMR ($\delta$ in ppm) | Multiplicity |
|---|---|---|---|
| 1 | | 202.0 | C |
| 2 | 4.80 (overlapped) | 76.4 | CH |
| 3 | 2.80 (overlapped) | 42.0 | CH |
| $4_{ax}$ | 2.55 (overlapped) | 26.9 | $CH_2$ |
| $4_{eq}$ | 3.00 (overlapped) | | |
| 4a | | 136.9 | C |
| 5 | 6.89 (s) | 101.5 | CH |
| 6 | | 159.1 | C |
| 7 | | 110.6 | C |
| 7-$CH_3$ | 2.17 (s) | 7.5 | $CH_3$ |
| 8 | | 155.4 | C |
| 8a | | 108.1 | C |
| 9 | | 165.0 | C |
| 9a | | 107.8 | C |

TABLE 17-continued

NMR of 4'-butanoyl-CRM (formula XCIV)
$^1$H-NMR (acetone-$d_6$, 600 MHz) and $^{13}$C-NMR (acetone-$d_6$, 150 MHz).
Data for compound XCIV

| Position | $^1$H-NMR (δ in ppm, multiplicity, J in Hz) | $^{13}$C-NMR (δ in ppm) | Multiplicity |
|---|---|---|---|
| 10 | 6.93 (s) | 117.2 | CH |
| 10a | | 141.3 | C |
| 1' | 4.84 (brs) | 81.3 | CH |
| 1'-OCH$_3$ | 3.54 (s) | 61.0 | CH$_3$ |
| 2' | | 209.4 | C |
| 3' | 4.48 dd (6.4, 2.4) coupled with OH | 76.2 | CH |
| 4' | 5.32 dq (6.0, 2.7) | 70.5 | CH |
| 5' | 1.32 (overlapped) | 15.3 | CH$_3$ |
| 6' | | 171.9 | C |
| 7' | 2.22 t (5.9) | 35.6 | CH$_2$ |
| 8' | 1.50 (overlapped) | 18.0 | CH$_2$ |
| 9' | 0.84 t (7.3) | 13.0 | CH$_3$ |
| 1A | 5.46 brd (8.9) | 97.2 | CH |
| 2A$_{ax}$ | 2.05 (overlapped) | 32.9 | CH$_2$ |
| 2A$_{eq}$ | 2.15 (overlapped) | | |
| 3A | 4.15 (overlapped)) | 69.7 | CH |
| 4A | 5.22 (brs) | 67.5 | CH |
| 4A-CH$^3$ | 2.15 (s) | 19.9 | CH$_3$ |
| 4A-CO | | 169.9 | C |
| 5A | 3.93 brq (6.5) | 69.4 | CH |
| 6A | 1.20 d (6.5) | 16.1 | CH$_3$ |
| 1B | 5.07 (overlapped) | 95.0 | CH |
| 2B$_{ax}$ | 1.58 dd (12.5, 4.4) | 33.1 | CH$_2$ |
| 2B$_{eq}$ | 1.90 m (complex signal) | | |
| 3B | 3.98 ddd (10.5, 6.0, 3.3) | 66.1 | CH |
| 4B | 3.21 brs | 81.6 | CH |
| 4B-OCH$_3$ | 3.41 (s) | 58.1 | CH$_3$ |
| 5B | 4.02 brq (6.2) | 67.0 | CH |
| 6B | 1.22 d (6.2) | 17.2 | CH$_3$ |
| 1C | 5.13 brd (9.3) | 100.5 | CH |
| 2C$_{ax}$ | 1.70 (signal not resolved) | 37.4 | CH$_2$ |
| 2C$_{eq}$ | 2.55 (overlapped) | | |
| 3C | 3.70 (overlapped) | 81.6 | CH |
| 4C | 3.00 (overlapped) | 75.3 | CH |
| 5C | 3.35 dq (9.0, 6.0) | 72.1 | CH |
| 6C | 1.32 (overlapped) | 17.4 | CH$_3$ |
| 1D | 4.80 (overlapped) | 99.4 | CH |
| 2D$_{ax}$ | 1.49 brq (10.4) | 36.5 | CH$_2$ |
| 2D$_{eq}$ | 2.40 brs (signal not resolved) | | |
| 3D | 3.70 (overlapped) | 76.0 | CH |
| 4D | 3.12 m (signal not resolved) | 74.9 | CH |
| 5D | 3.45 dq (9.0, 6.0) | 72.4 | CH |
| 6D | 1.32 (overlapped) | 17.6 | CH$_3$ |
| 1E | 5.07 (overlapped) | 94.5 | CH |
| 2E$_{ax}$ | 1.95 (overlapped) | 43.9 | CH$_2$ |
| 2E$_{eq}$ | 2.00 (overlapped) | | |
| 3E | | 69.5 | C |
| 3E-CH$_3$ | 1.43 (s) | 22.7 | CH$_3$ |
| 4E | 4.68 d (9.7) | 79.3 | CH |
| 4E-CH$_3$ | 2.06 (s) | 20.1 | CH$_3$ |
| 4E-CO | | 170.2 | C |
| 5E | 4.11 dq (9.8, 6.0) | 65.7 | CH |
| 6E | 1.12 d (6.0) | 16.5 | CH$_3$ |

In the particular case of using vinyl decanoate as acylating agent the reaction time was of two days and a conversion of 90% was reached. A unique acylated derivative was identified by HPLC (FIG. 59) which was purified using a mixture of acetonitrile and 0.1% trifluoroacetic acid in water (70:30) as mobile phase at a flow of 20 ml/min. The new isolated compound was identified as 4'-decanoylchromomycin A$_3$ (formula XCV).

Structure elucidation of the new derivatives was carried out by NMR. Table 18 shows the data obtained for compound of formula (XCV).

TABLE 18

NMR de 4'-decanoyl-CRM (formula XCV)
$^1$H-NMR (acetone-$d_6$, 600 MHz). Data for compound XCV

| Position | $^1$H-NMR (δ in ppm, multiplicity, J in Hz) |
|---|---|
| 1 | |
| 2 | 4.82 d (11.6) |
| 3 | 2.85 (complex signal) |
| 4ax | 2.55 dd (15.4, 11.8) |
| 4eq | 3.07 brd (16.0) |
| 4a | |
| 5 | 6.85 (s) |
| 6 | |
| 7 | |
| 7-CH$_3$ | 2.17 (s) |
| 8 | |
| 8a | |
| 9 | |
| 9a | |
| 10 | 6.95 (s) |
| 10a | |
| 1' | 4.92 s (1.3) |
| 1'-OCH$_3$ | 3.54 (s) |
| 2' | |
| 3' | 4.45 brs |
| 4' | 5.30 dq (6.0, 2.7) |
| 5' | 1.34 d (6.0) |
| 6' | |
| 7' | 2.29 t (7.4) |
| 8' | 1.60 (overlapped) |
| 9' | 1.20 (overlapped) |
| 10' | 1.20 (overlapped) |
| 11' | 1.20 (overlapped) |
| 12' | 1.20 (overlapped) |
| 13' | 1.20 (overlapped) |
| 14' | 1.20 (overlapped) |
| 15' | 0.89 t (7.3) |
| 1A | 5.50 dd (9.6, 2.2) |
| 2A$_{ax}$ | 2.05 (overlapped) |
| 2A$_{eq}$ | 2.15 (solapado) |
| 3A | 4.15 ddd (12.2, 4.8, 3.3) |
| 4A | 5.22 d (2.8) |
| 4A-CH$_3$ | 2.15 (s) |
| 4A-CO | |
| 5A | 3.91 brq (6.6) |
| 6A | 1.20 d (6.6) |
| 1B | 5.06 d (3.2) |
| 2B$_{ax}$ | 1.60 (overlapped) |
| 2B$_{eq}$ | 1.90 (complex signal) |
| 3B | 3.98 ddd (11.9, 4.4, 2.9) |
| 4B | 3.22 brs |
| 4B-OCH$_3$ | 3.40 (s) |
| 5B | 4.05 brq(6.4) |
| 6B | 1.21 d (6.4) |
| 1C | 5.11 dd (9.7, 1.7) |
| 2C$_{ax}$ | 1.70 (complex signal) |
| 2C$_{eq}$ | 2.56 ddd (11.3, 5.2, 1.7) |
| 3C | 3.72 (overlapped) |
| 4C | 3.04 t (9.0) |
| 5C | 3.33 dq (9.0, 6.2) |
| 6C | 1.30 d (6.2) |
| 1D | 4.81 (overlapped) |
| 2D$_{ax}$ | 1.50 (overlapped) |
| 2D$_{eq}$ | 2.41 ddd (12.4, 5.0, 1.8) |
| 3D | 3.72 (overlapped) |
| 4D | 3.13 t (9.0) |
| 5D | 3.47 dq (9.0, 6.3) |
| 6D | 1.33 d (6.3) |
| 1E | 5.09 dd (4.0, 1.5) |
| 2E$_{ax}$ | 1.95 dd (12.0, 4.0) |
| 2E$_{eq}$ | 2.00 dd (12.0, 1.5) |
| 3E | |
| 3E-CH$_3$ | 1.43 (s) |
| 4E | 4.68 d (9.7) |
| 4E-CH$_3$ | 2.07 (s) |
| 4E-CO | |
| 5E | 4.11 dq (9.8, 6.4) |
| 6E | 1.12 d (6.4) |

In the particular case of using vinyl adipate as acylating agent the reaction time was of seven days and a conversion of 90% was reached. A unique acylated derivative was identified by HPLC (FIG. 60) which was purified using a mixture of acetonitrile and 0.1% trifluoroacetic acid in water (60:40) as mobile phase at a flow of 20 ml/min.

The new isolated compound was identified as 4'-(5-vinyloxycarbonyl)pentanoylchromomycin (formula XCVI).

Structure elucidation of the new derivatives was carried out by NMR. Table 19 shows the data obtained for compound of formula (XCVI).

TABLE 19

NMR of 4'-adipoyl-CRM (formula XCVI)
$^1$H-NMR (acetone-$d_6$, 600 MHz) and $^{13}$C-NMR (acetone-$d_6$, 150 MHz).
Data for compound XCVI

| Position | $^1$H-NMR ($\delta$ in ppm, multiplicity, J in Hz) | $\delta$ $^{13}$C (ppm) | multiplicity |
|---|---|---|---|
| 1 | | 200.5 | C |
| 2 | 4.80 (overlapped) | 76.4 | CH |
| 3 | 2.80 (overlapped) | 41.8 | CH |
| $4_{ax}$ | 3.00 (overlapped) | 26.9 | $CH_2$ |
| $4_{eq}$ | 2.50 (overlapped with $2C_{eq}$) | | |
| 4a | | 138.6 | C |
| 5 | 6.88 (s) | 101.6 | CH |
| 6 | | 159.5 | C |
| 7 | | 110.6 | C |
| 7-$CH_3$ | 2.17 (s) | 7.5 | $CH_3$ |
| 8 | | 155.0 | C |
| 8a | | 108.1 | C |
| 9 | | 165.0 | C |
| 9a | | 107.8 | C |
| 10 | 6.92 (s) | 117.0 | CH |
| 10a | | 141.2 | C |
| 1' | 4.90 (s) | 81.2 | CH |
| 1'-$OCH_3$ | 3.54 (s) | 61.0 | $CH_3$ |
| 2' | | 209.6 | C |
| 3' | 4.45 brs | 76.2 | CH |
| 4' | 5.35 m (signal not resolved) | 70.6 | CH |
| 5' | 1.30 (overlapped) | 15.3 | $CH_3$ |
| 6' | | 171.8 | C |
| 7' | 2.40 m (overlapped) | 33.4 | $CH_2$ |
| 8' | 1.50 (overlapped) | 24.1 | $CH_2$ |
| 9' | 1.50 (overlapped) | 24.0 | $CH_2$ |
| 10' | 2.40 m (overlapped) | 33.3 | $CH_2$ |
| 11' | | 179.8 | C |
| 12' | 7.25 dd (14.0, 6.3) | 141.3 | CH |
| 13' (Z) | 4.55 dd (6.3, 1.5) | 96.8 | $CH_2$ |
| 13' (E) | 4.85 dd (14.0, 1.5) | | |
| 1A | 5.50 d (8.9) | 97.1 | CH |
| $2A_{ax}$ | 2.05 (overlapped) | 32.9 | $CH_2$ |
| $2A_{eq}$ | 2.15 (overlapped) | | |
| 3A | 4.15 (overlapped)) | 69.8 | CH |
| 4A | 5.20 (s) | 67.6 | CH |
| 4A-$CH_3$ | 2.15 (s) | 19.9 | $CH_3$ |
| 4A-CO | | 170.0 | C |
| 5A | 4.05 q (6.3) | 69.4 | CH |
| 6A | 1.32 d (overlapped) | 16.1 | $CH_3$ |
| 1B | 5.05 m (signal not resolved) | 95.0 | CH |
| $2B_{ax}$ | 1.60 (overlapped) | 33.1 | $CH_2$ |
| $2B_{eq}$ | 1.80 m (signal not resolved) | | |
| 3B | 4.00 m (signal not resolved) | 66.1 | CH |
| 4B | 3.20 brs | 81.6 | CH |
| 4B-$OCH_3$ | 3.40 (s) | 58.1 | $CH_3$ |
| 5B | 4.00 m (overlapped) | 67.0 | CH |
| 6B | 1.20 d (overlapped) | 17.2 | $CH_3$ |
| 1C | 5.12 d (9.1) | 100.5 | CH |
| $2C_{ax}$ | 1.70 (overlapped) | 37.4 | $CH_2$ |
| $2C_{eq}$ | 2.50 (overlapped with $4_{eq}$) | | |
| 3C | 3.70 (overlapped with 3D) | 81.6 | CH |
| 4C | 3.00 (overlapped $4_{ax}$) | 75.3 | CH |
| 5C | 3.30 m (signal not resolved) | 72.1 | CH |
| 6C | 1.35 d (overlapped) | 17.4 | $CH_3$ |
| 1D | 4.80 (overlapped) | 99.4 | CH |
| $2D_{ax}$ | 1.50 (overlapped) | 36.5 | $CH_2$ |
| $2D_{eq}$ | 2.35 m (signal not resolved) | | |
| 3D | 3.70 (overlapped with 3C) | 76.2 | CH |
| 4D | 3.10 m (overlapped) | 74.9 | CH |
| 5D | 3.40 m (signal not resolved) | 72.4 | CH |
| 6D | 1.35 d (overlapped) | 17.6 | $CH_3$ |
| 1E | 5.10 (overlapped) | 94.5 | CH |
| $2E_{ax}$ | 1.95 (overlapped) | 43.9 | $CH_2$ |
| $2E_{eq}$ | 2.00 (overlapped) | | |
| 3E | | 69.5 | C |
| 3E-$CH_3$ | 1.44 (s) | 22.7 | $CH_3$ |
| 4E | 4.68 d (9.7) | 79.3 | CH |
| 4E-$CH_3$ | 2.10 (s) | 20.1 | $CH_3$ |
| 4E-CO | | 170.2 | C |
| 5E | 4.15 (overlapped) | 65.7 | CH |
| 6E | 1.12 d (6.0) | 16.5 | $CH_3$ |

Example 15

Antitumor Activity of Compounds of Formula (VII), (VIII), (IX), (XII), (XIII), (XIV), (XVI), (XVII), (XVIII), (XIX), (XX), (XXXI), (XXXVIII), (XLVI), (LI), (LII), (LIII), (LV), (LXI), (LXVIII), (LXIX)

Cell Culture

MTM and CRM derivatives were assayed against a collection of tumor cell lines. Tumor cell lines were obtained from The American Type and Culture Collection (ATCC), and the lines were the following; A549 (human lung carcinoma); H116 (colon adenocarcinoma); PSN1 (pancreatic adenocarcinoma) and T98G (human glyoblastoma). Cells were cultured in medium RPM1 containing 2 mM glutamine, 50 IU/ml penicillin and 50 µg/ml streptomycin. Culture medium for cell lines A549 and H116 was supplemeted with 5% FBS and culture medium for cell lines PSN1 and T98G was supplemented with 10% FBS.

Cell Proliferation Assay

The evaluation of compound cytotoxicity was carried out by determining cell viability using an assay based on metabolic reduction of 3-(4,5-dimethyl-2-thiazolyl)-2,5-diphenyltetrazolium bromide (MTT; Sigma Chemical Co. St. Louis, Mo.). This reduction reaction is carried out by mitochondrion succinate dehydrogenase of viable cells and produce formazan, a chromogenic compound that can be quantified by spectrophotometry.

The assay was carried out following the procedure described by Mosmann (*J. Immunol. Methods* 1983, 65, 55). Tumor cells were incubated in 96 well microtitre plates containing 200 µl of complete medium (with 4×10$^3$ cells/well for A549 and 6×10$^3$ cells/well for H116, PSN1 and T98G). Serial dilutions in DMSO of the test compounds (10 µg/ml, 5 µg/ml, 1 µg/ml, 0.5 µg/ml, 0.1 µg/ml, 0.05 µg/ml, 0.01 µg/ml, y 0.005 µg/ml) were added and after 2 days incubation (at 37° C., 5% CO$_2$ and high relative humidity), 50 µl of MTT (1 mg/ml in PBS) was added to each well. The plates were incubated at 37° C. for 2 hours and the reduction product (formazan) was resuspended in 100 µl of DMSO and and quantified at 490 nm with a spectrophotometer. All the studies were done in triplicate and the results are shown in Table 20.

TABLE 20

Antitumor activity of aureolic acid derivatives of formula (VII), (VIII), (IX), (XII), (XIII), (XIV), (XVI), (XVII), (XVIII), (XIX), (XX), (XXXI), (XXXVIII), (XLVI), (LI), (LII), (LIII), (LV), (LXI), (LXVIII), (LXIX) against several tumor cell lines. Data from MTM, MTM-SK, MTM-SDK, 3D-demycarosyl-MTM-SK and 3D-demycarosyl-3D-β-D-digitoxosyl-MTM has been included as a reference. Numeral data is referred as $IC_{50}$ (μM) or concentration required to achieve 50% growth inhibition compared to untreated cells.

| Compounds | A549 (lung) | H116 (colon) | PSN1 (prostate) | T98G (glyoblastoma) |
|---|---|---|---|---|
| MTM | 0.046 | 0.0092 | 0.0092 | 0.069 |
| MTM-SK | 0.0094 | 0.0094 | 0.0094 | 0.0473 |
| MTM-SDK | 0.0094 | 0.0094 | 0.0094 | 0.0474 |
| 3D-demycarosyl-MTM-SK | 1 | 0.5 | 1 | >1 |
| 3D-demycarosyl-3D-β-D-digitoxosyl-MTM | 0.0466 | 0.0466 | 0.0466 | 0.069 |
| (VII) | 0.05 | 0.01 | 0.1 | 0.3 |
| (VIII) | 0.05 | 0.05 | 0.1 | 0.3 |
| (IX) | 0.005 | 0.005 | 0.005 | 0.01 |
| (XII) | 0.05 | 0.01 | 0.05 | 0.3 |
| (XIII) | 0.01 | 0.003 | 0.01 | 0.05 |
| (XIV) | 0.05 | 0.01 | 0.05 | 0.75 |
| (XVI) | 0.0449 | 0.0089 | 0.0089 | 0.4716 |
| (XVII) | 0.0449 | 0.0449 | 0.0089 | 0.0674 |
| (XVIII) | 0.0449 | 0.0449 | 0.0089 | 0.0898 |
| (XIX) | 0.0432 | 0.0432 | 0.0086 | 0.2121 |
| (XX) | 0.0417 | 0.0083 | 0.0083 | 0.309 |
| (XXXI) | 0.043 | 0.043 | 0.043 | 0.043 |
| (XXXVIII) | 0.008 | 0.008 | 0.004 | 0.043 |
| (XLVI) | 0.433 | 0.043 | 0.043 | 0.043 |
| (LI) | 0.043 | 0.043 | 0.043 | 0.087 |
| (LII) | 0.42 | 0.42 | 0.42 | 0.844 |
| (LIII) | 4.21 | 0.844 | 0.633 | 0.844 |
| (LV) | 4.21 | 4.21 | 0.422 | 4.21 |
| (LXI) | 0.045 | 0.009 | 0.0065 | 0.045 |
| (LXVIII) | 0.0065 | 0.004 | 0.009 | 0.004 |
| (LXIX) | 0.009 | 0.009 | 0.045 | 0.004 |

Peak 2=4'-acetyl-MTM [formula (XXIII)]; Peak 3=3B-acetyl-MTM [formula (XXIV)].

Figure 1:
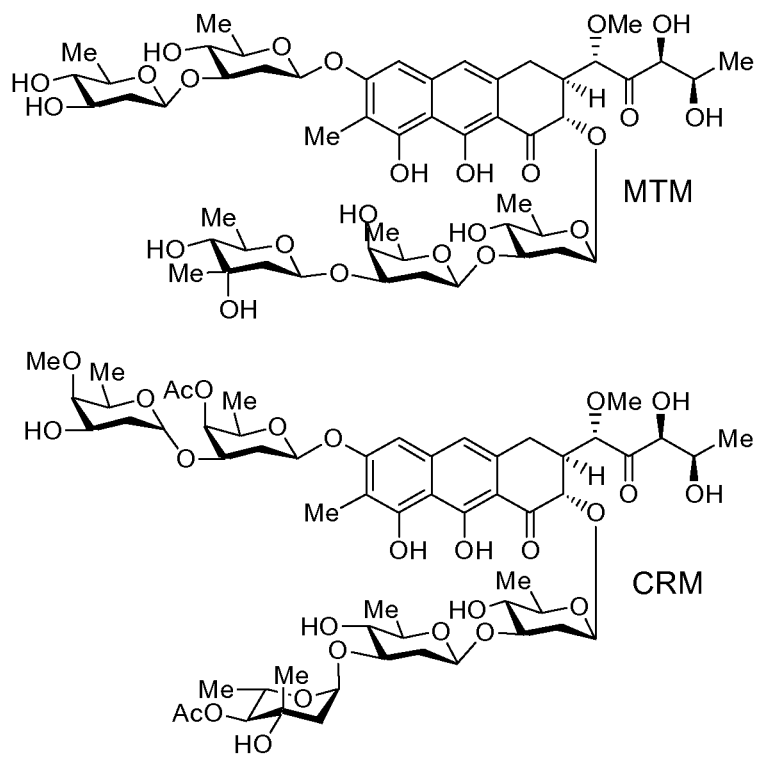
FIG. 1: Structures of mythramycin and chromomycin $A_3$.
Figure 2:
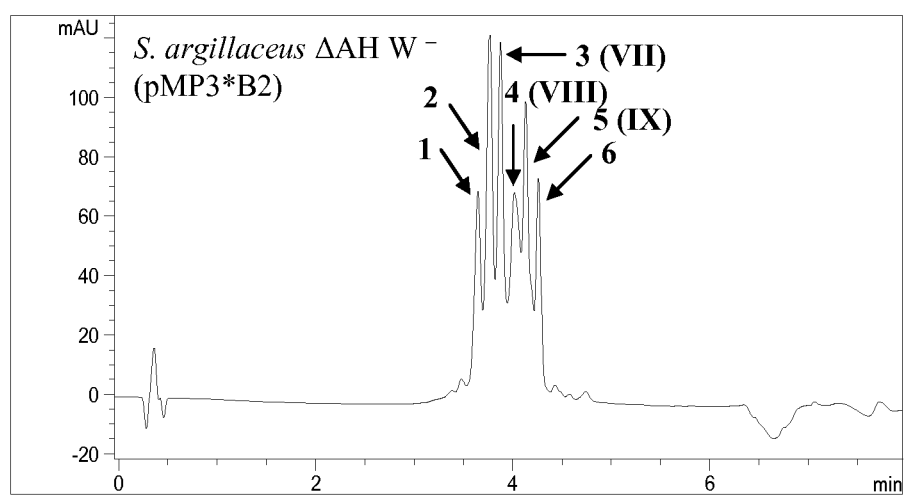
FIG. 2: HPLC analysis of an ethyl acetate extract of *S. argillaceus* ΔAH W⁻ (pMP3*BII). Peak 1=demycarosyl-3D-MTM-SK; Peak 2=3D-demycarosyl-3D-β-D-digitoxosyl-MTM-SK [formula (VII)]; Peak 3=MTM-SK; Peak 4=demycarosyl-3D-MTM-SDK [formula (VIII)]; Peak 5=3D-demycarosyl-3D-β-D-digitoxosyl-MTM-SDK [formula (IX)]; Peak 6=MTM-SDK.
Figure 3:
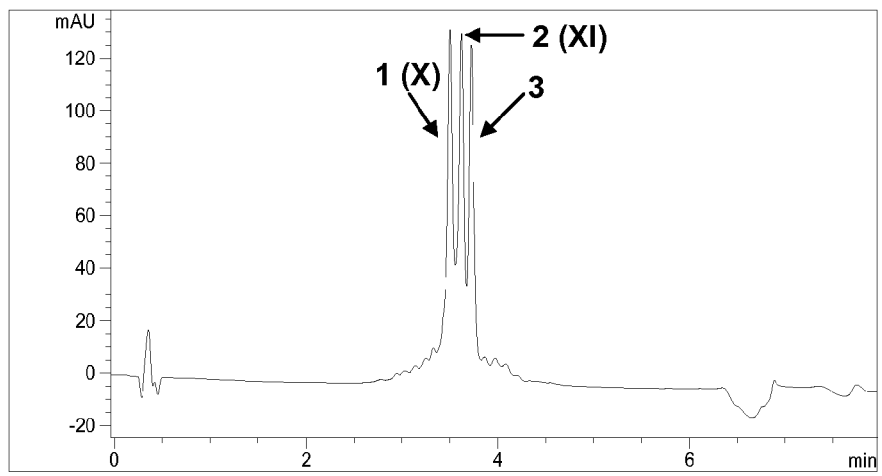
FIG. 3: HPLC analysis of a methanol extract of *S. argillaceus* ΔAH W⁻ (pMP3*BII). Peak 1=demycarosyl-3D-MTM-SA [formula (X)]; Peak 2=3D-demycarosyl-3D-β-D-digitoxosyl-MTM-SA [formula (XI)]; Peak 3=MTM-SA.
Figure 4:
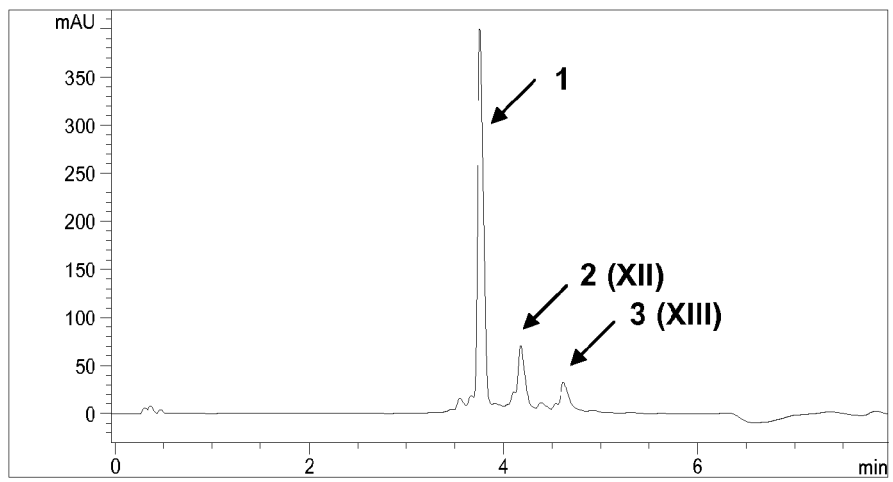
FIG. 4: HPLC analysis of the bioconversion reaction of MTM using *S. griseus* C10GIV. Peak 1=MTM; Peak 2=acetyl-MTM [formula (XII)]; Peak 3=diacetyl-MTM [formula (XIII)].
Figure 5:
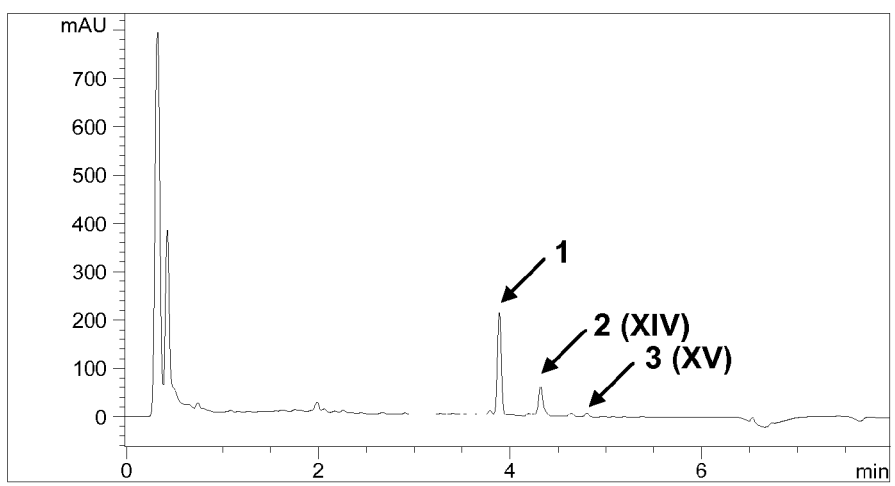
FIG. 5: HPLC analysis of the bioconversion reaction of MTM-SK using *S. griseus* C10GIV. Peak 1=MTM-SK; Peak 2=acetyl-MTM-SK [formula (XIV)]; Peak 3=diacetyl-MTM-SK [formula (XV)].
Figure 6:
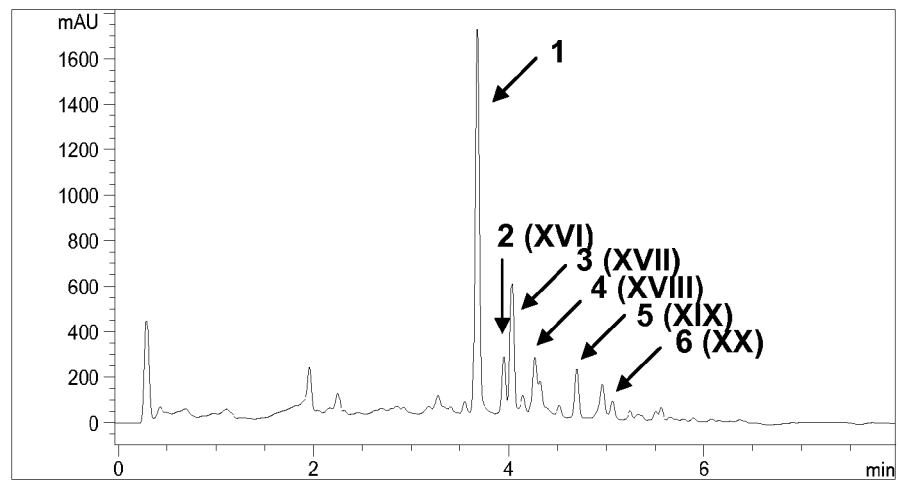
FIG. 6: HPLC analysis of the bioconversion reaction of 3D-demycarosyl-3D-β-D-digitoxosyl-MTM using *S. griseus* C10GIV. Peak 1=3D-demycarosyl-3D-β-D-digitoxosyl-MTM; Peak 2=acetyl-3D-demycarosyl-3D-β-D-digitoxosyl-MTM [formula (XVI)]; Peak 3=acetyl-3D-demycarosyl-3D-β-D-digitoxosyl-MTM [formula (XVII)]; Peak 4=acetyl-3D-demycarosyl-3D-β-D-digitoxosyl-MTM [formula (XVIII)]; Peak 5=diacetyl-3D-demycarosyl-3D-β-D-digitoxosyl-MTM [formula (XIX)]; Peak 6=triacetyl-3D-demycarosyl-3D-β-D-digitoxosyl-MTM [formula (XX)].
Figure 7:
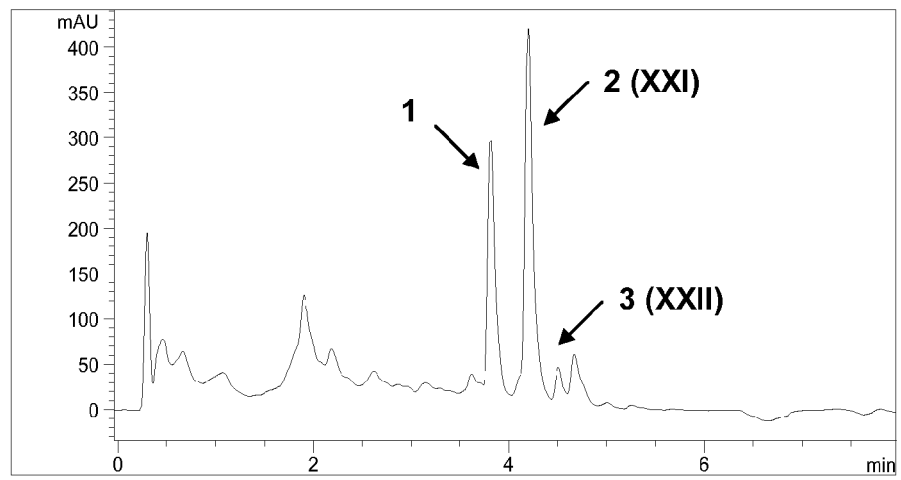
FIG. 7: HPLC analysis of the bioconversion reaction of 3D-demycarosyl-3D-β-D-digitoxosyl-MTM-SK using *S. griseus* C10GIV. Peak 1=3D-demycarosyl-3D-β-D-digitoxosyl-MTM-SK; Peak 2=acetyl-3D-demycarosyl-3D-β-D-digitoxosyl-MTM-SK [formula (XXI)]; Peak 3=diacetyl-3D-demycarosyl-3D-β-D-digitoxosyl-MTM-SK [formula (XXII)].
Figure 8:
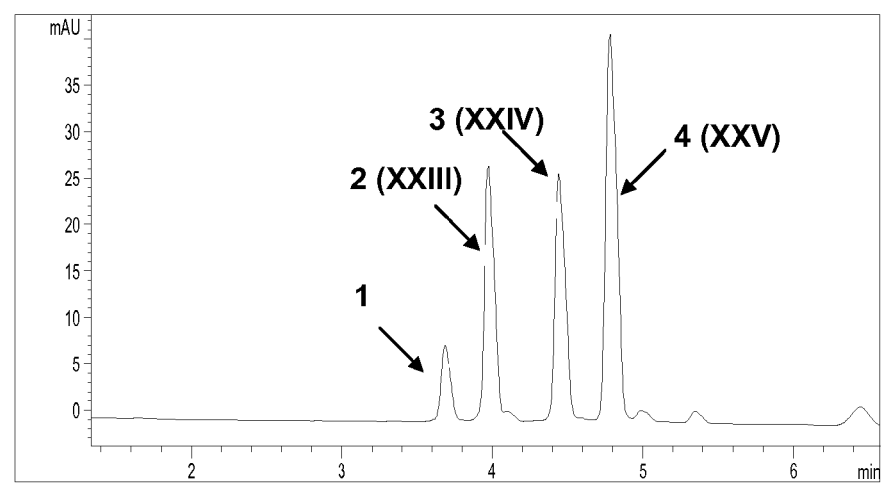
FIG. 8: HPLC analysis of the enzymatic acylation reaction of MTM using vinyl acetate and CAL-B. Peak 1=MTM; Peak 2=4'-acetyl-MTM [formula (XXIII)]; Peak 3=3B-acetyl-MTM [formula (XXIV)]; Peak 4=4',3B-diacetyl-MTM [formula (XXV)].
Figure 9:
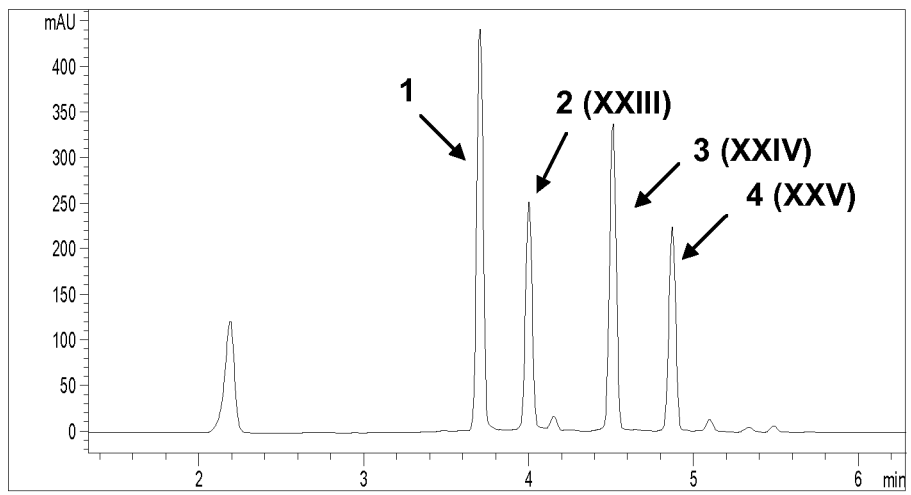
FIG. 9: HPLC analysis of the enzymatic acylation reaction of MTM using 2,2,2-trifluoroethyl acetate and CAL-B. Peak 1=MTM; Peak 2=4'-acetyl-MTM [formula (XXIII)]; Peak 3=3B-acetyl-MTM [formula (XXIV)]; Peak 4=4',3B-diacetyl-MTM [formula (XXV)].
Figure 10:
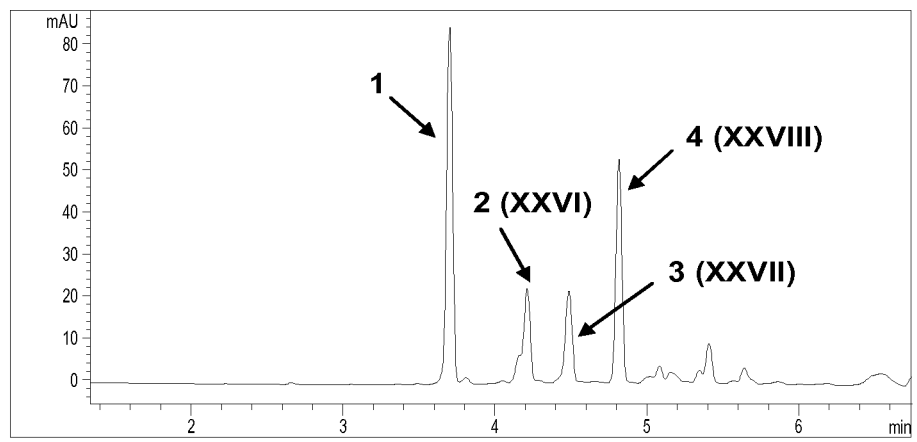
FIG. 10: HPLC analysis of the enzymatic acylation reaction of MTM using vinyl chloroacetate and CAL-B. Peak 1=MTM; Peak 2=compound of formula XXVI; Peak 3=compound of formula XXVII; Peak 4=compound of formula XVIII.
Figure 11:
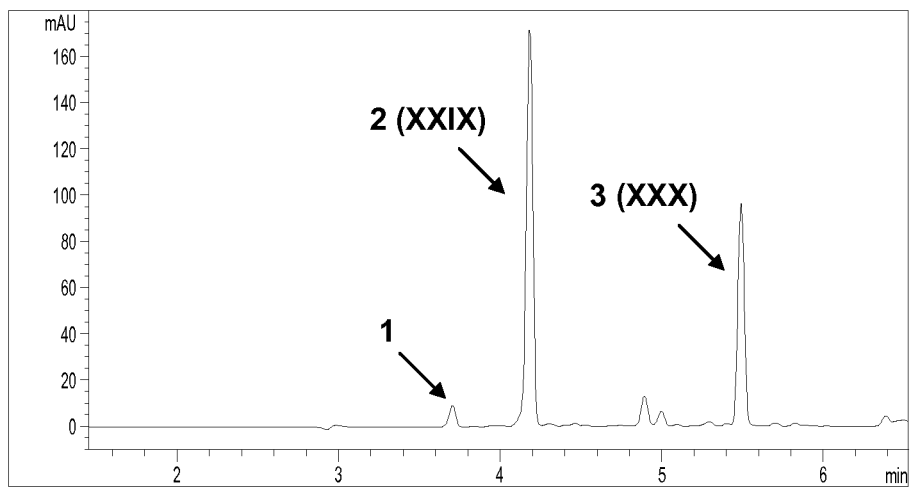
FIG. 11: HPLC analysis of the enzymatic acylation reaction of MTM using vinyl propanoate and CAL-B. Peak 1=MTM; Peak 2=4'-propanoyl-MTM [formula (XXIX)]; Peak 3=4',3B-dipropanoyl-MTM [formula (XXX)].
Figure 12:
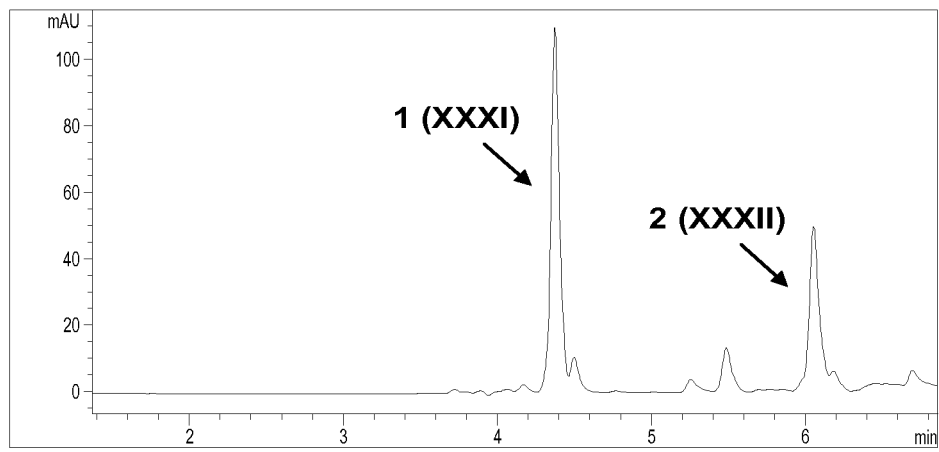
FIG. 12: HPLC analysis of the enzymatic acylation reaction of MTM using vinyl butanoate and CAL-B. Peak 1=4'-butanoyl-MTM [formula (XXXI)]; Peak 2=4',3B-dibutanoyl-MTM [formula (XXXII)].
Figure 13:
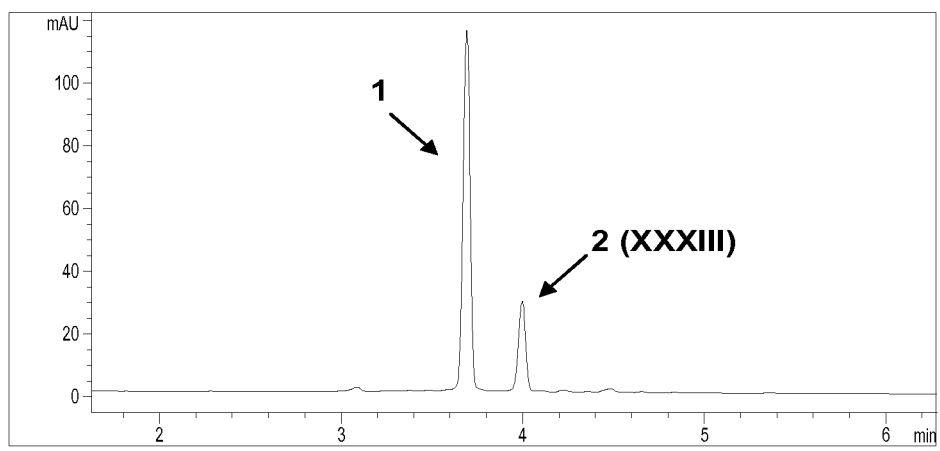
FIG. 13: HPLC analysis of the enzymatic acylation reaction of MTM using acetonoxime levulinate and CAL-B. Peak 1=MTM; Peak 2=compound of formula XXXIII.
Figure 14:
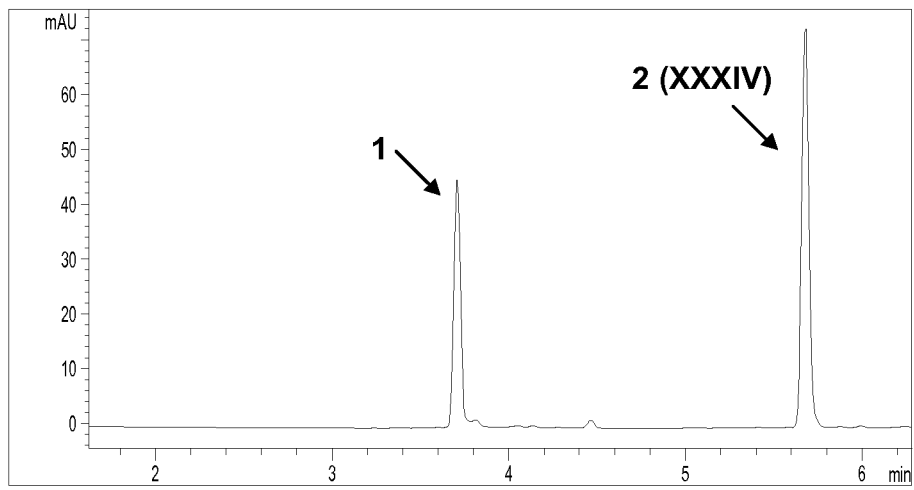
FIG. 14: HPLC analysis of the enzymatic acylation reaction of MTM using vinyl decanoate and CAL-B. Peak 1=MTM; Peak 2=4'-decanoyl-MTM [formula (XXXIV)].
Figure 15:
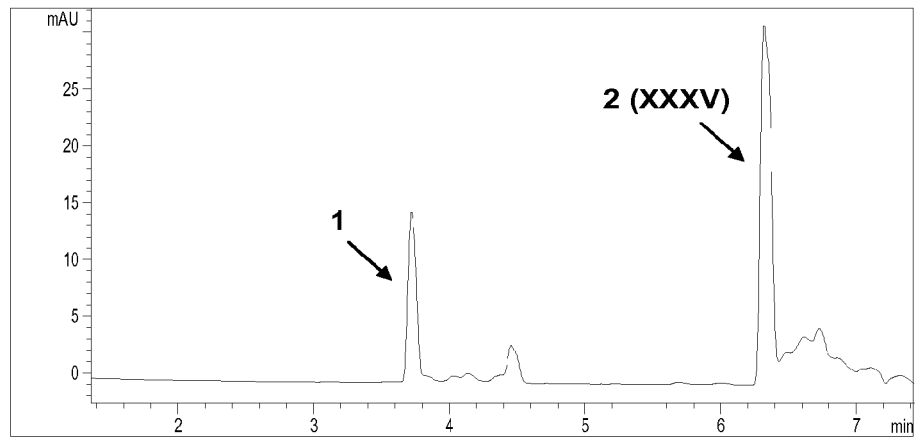
FIG. 15: HPLC analysis of the enzymatic acylation reaction of MTM using vinyl dodecanoate and CAL-B. Peak 1=MTM; Peak 2=compound of formula XXV.
Figure 16:
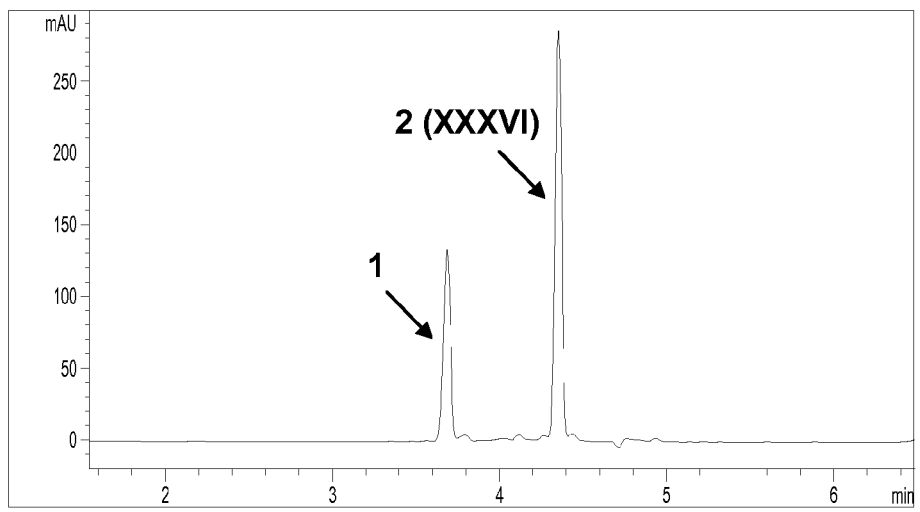
FIG. 16: HPLC analysis of the enzymatic acylation reaction of MTM using vinyl benzoate and CAL-B. Peak 1=MTM; Peak 2=4'-benzoyl-MTM [formula (XXXVI)].
Figure 17:
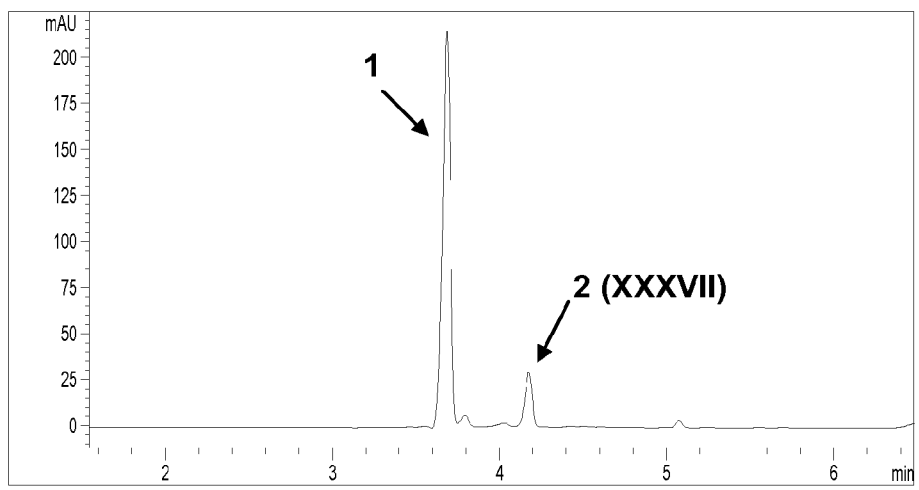
FIG. 17: HPLC analysis of the enzymatic acylation reaction of MTM using vinyl crotonate and CAL-B. Peak 1=MTM; Peak 2=compound of formula XXXVII.
Figure 18:
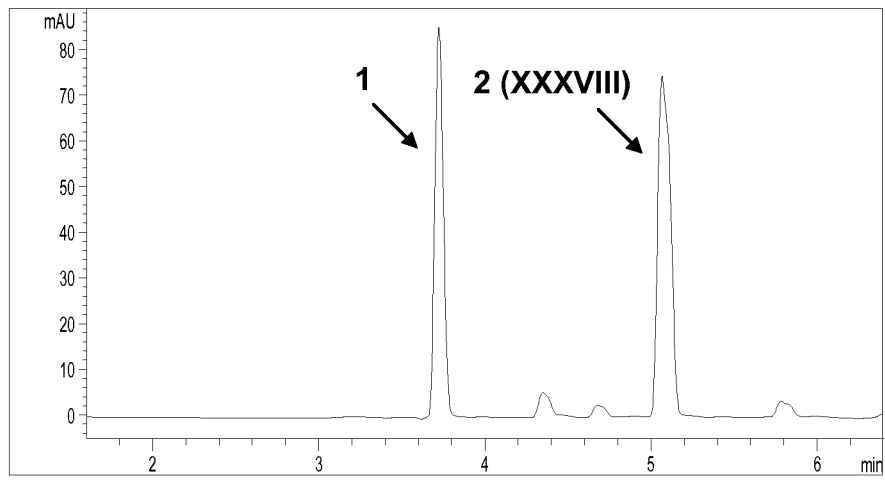
FIG. 18: HPLC analysis of the enzymatic acylation reaction of MTM using diallyl carbonate and CAL-B. Peak 1=MTM; Peak 2=3B-allyloxycarbonyl-MTM [formula (XXXVIII)].
Figure 19:
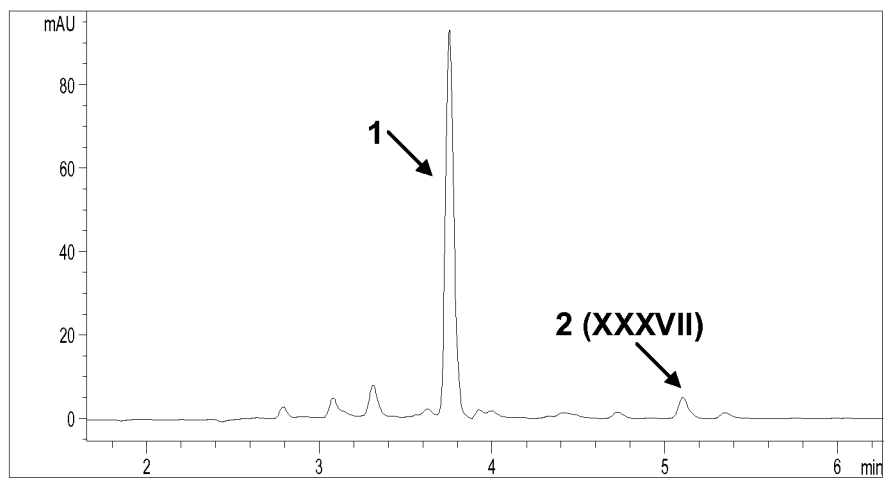
FIG. 19: HPLC analysis of the enzymatic acylation reaction of MTM using allyl oxime carbonate and CAL-B. Peak 1=MTM; Peak 2=3B-allyloxycarbonyl-MTM [formula (XXXVIII)].
Figure 20:
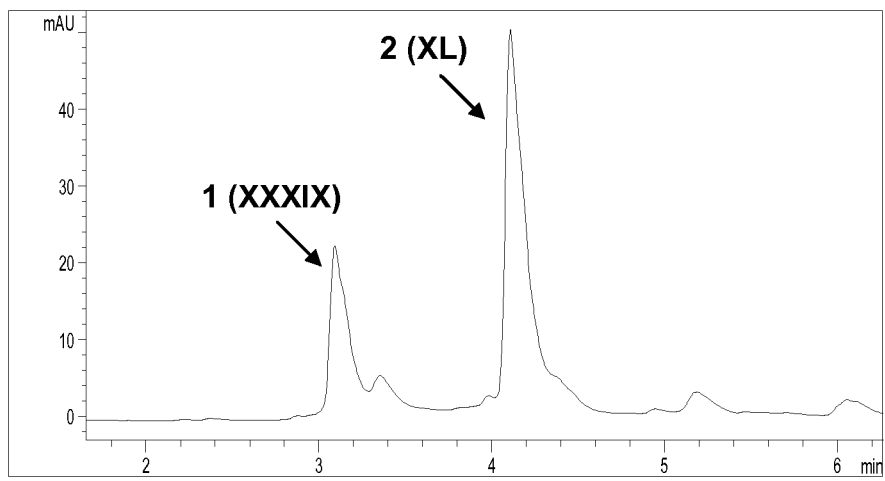
FIG. 20: HPLC analysis of the enzymatic acylation reaction of MTM using vinylene carbonate and CAL-B. Peak 1=compound of formula XXXIX; Peak 2=compound of formula XL.
Figure 21:
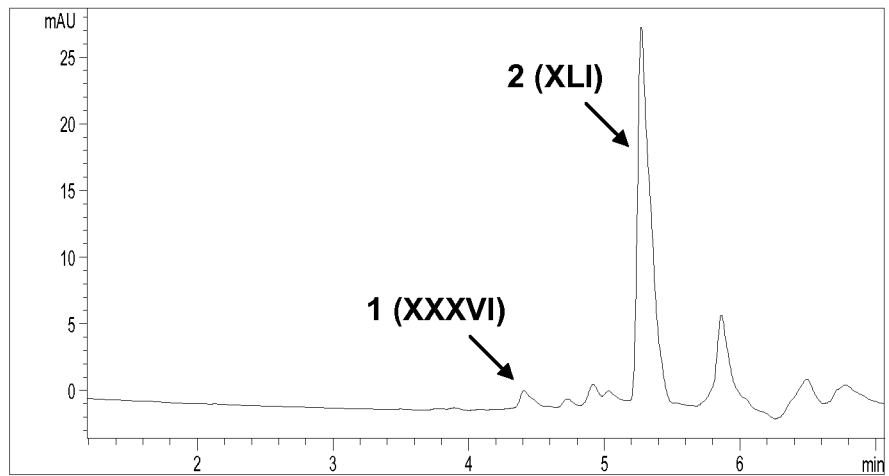
FIG. 21: HPLC analysis of the enzymatic acylation reaction of 4'-Bz-MTM using vinyl acetate and CAL-B. Peak 1=4'-Bz-MTM [formula (XXXVI)]; Peak 2=3B-acetyl-4'-benzoyl-MTM [formula (XLI)].
Figure 22:
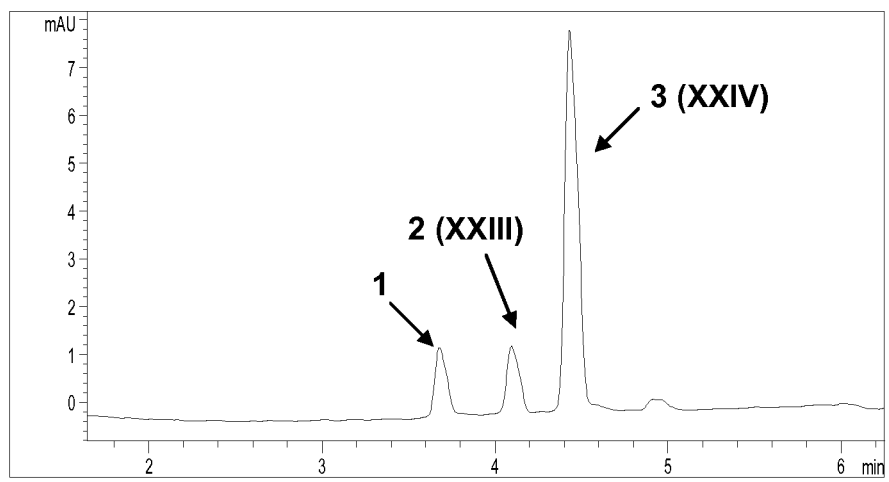
FIG. 22: HPLC analysis of the enzymatic acylation reaction of MTM using vinyl acetate and CAL-A. Peak 1=MTM.
Figure 23:
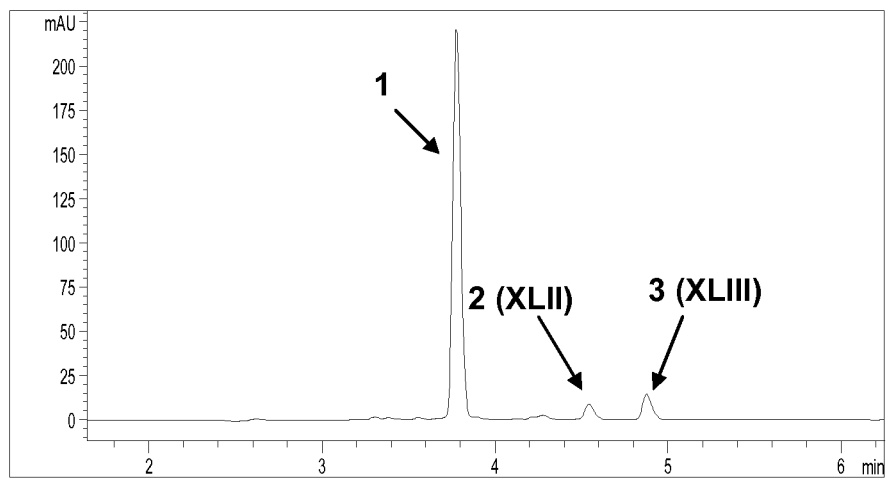

FIG. 23: HPLC analysis of the enzymatic acylation reaction of MTM using vinyl cloroacetate and CAL-A. Peak 1=MTM; Peak 2=compound of formula XLII; Peak 3=compound of formula XLIII.

Figure 24:
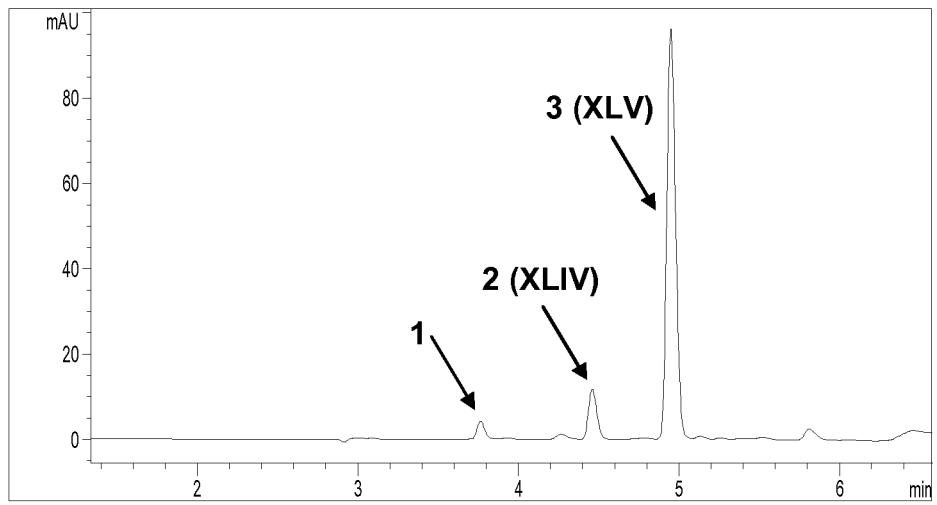

FIG. 24: HPLC analysis of the enzymatic acylation reaction of MTM using vinyl propanoate and CAL-A. Peak 1=MTM; Peak 2=3B-propanoyl-MTM [formula (XLIV)]; Peak 3=4B-propanoyl-MTM [formula (XLV)].

Figure 25:
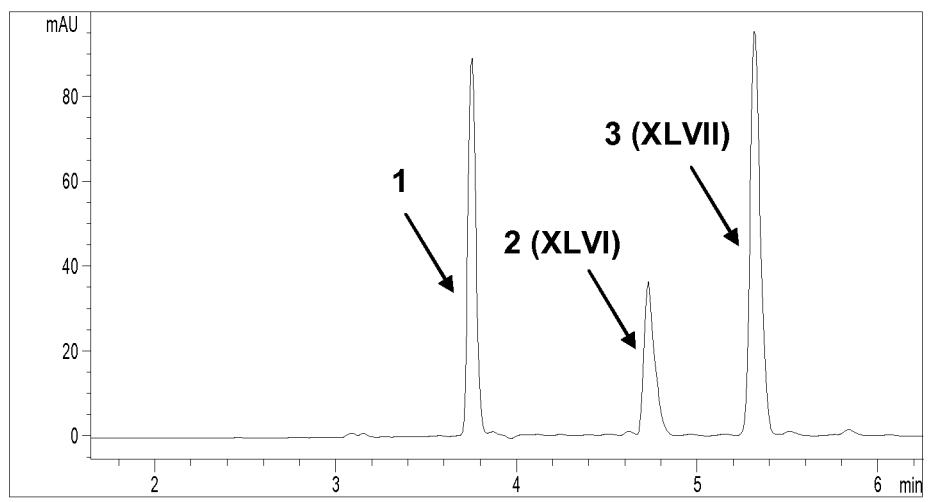

FIG. 25: HPLC analysis of the enzymatic acylation reaction of MTM using vinyl butanoate and CAL-A. Peak 1=MTM; Peak 2=3B-butanoyl-MTM [formula (XLVI)]; Peak 3=4B-butanoiy-MTM [formula (XLVII)].

Figure 26:
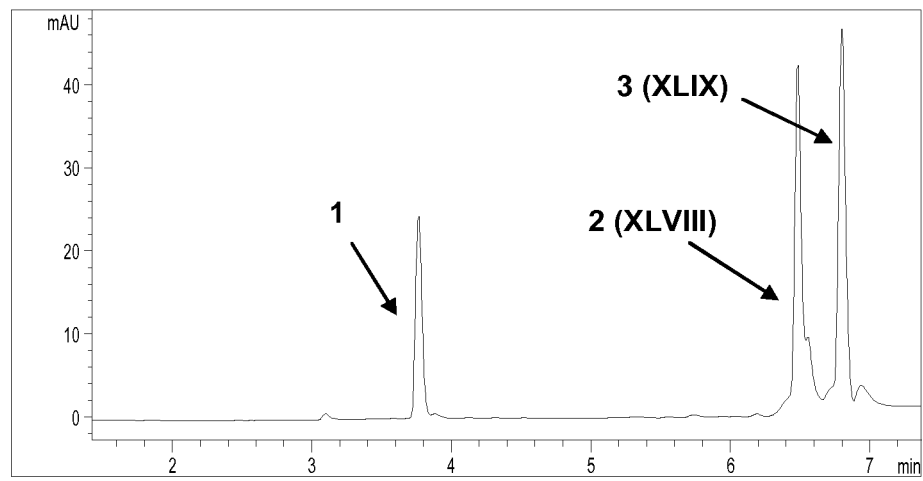

FIG. 26: HPLC analysis of the enzymatic acylation reaction of MTM using vinyl decanoate and CAL-A. Peak 1=MTM; Peak 2=3B-decanoyl-MTM [formula (XLVIII)]; 3=4B-decanoyl-MTM [formula (XLIX)].

Figure 27:
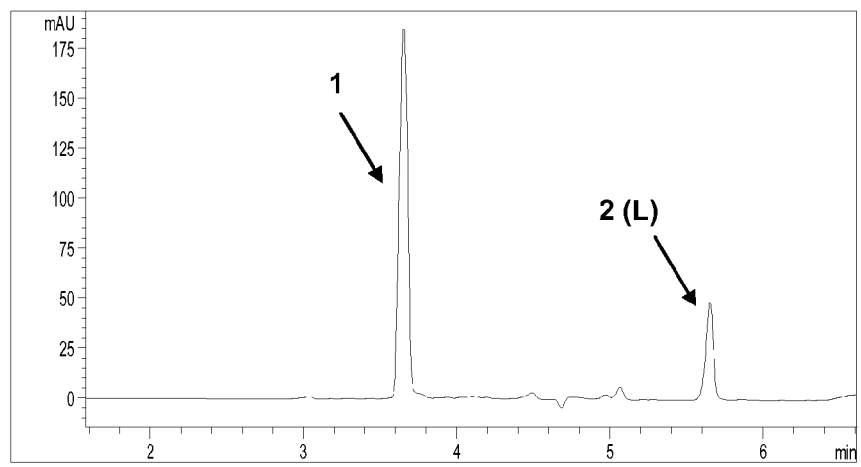

FIG. 27: HPLC analysis of the enzymatic acylation reaction of MTM using vinyl benzoate and CAL-A. Peak 1=MTM; Peak 2=compound of formula L.

Figure 28:
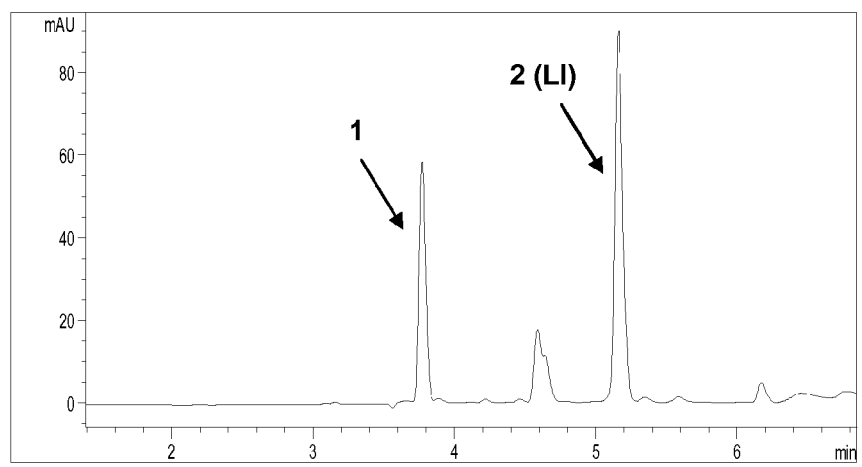

FIG. 28: HPLC analysis of the enzymatic acylation reaction of MTM using vinyl crotonate and CAL-A. Peak 1=MTM; Peak 2=3B-crotonoyl-MTM [formula (LI)].

Figure 29:
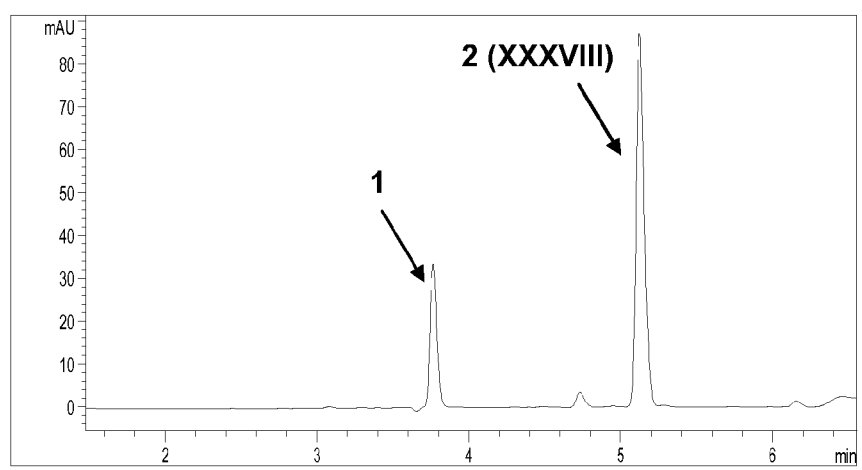

FIG. 29: HPLC analysis of the enzymatic acylation reaction of MTM using diallyl carbonate and CAL-A. Peak 1=MTM; Peak 2=3B-allyloxycarbonyl-MTM [formula (XXXVIII)].

Figure 30:
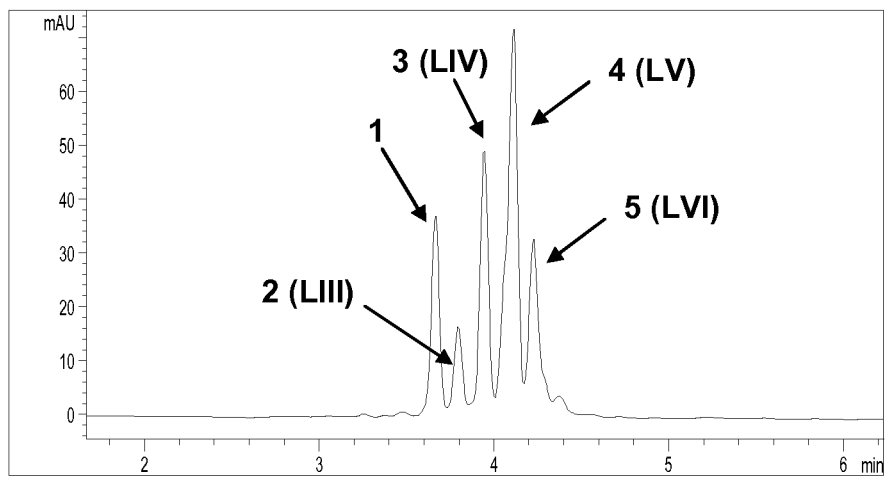

FIG. 30: HPLC analysis of the enzymatic acylation reaction of MTM using succinic anhydride and CAL-A. Peak 1=MTM; Peak 2=4'-(3-carboxypropanoyl)-MTM [formula (LII)], Peak 2=4B-(3-carboxypropanoyl)-MTM [formula (LIII)], Peak 3=4',4B-di-(3-carboxypropanoyl)-MTM [formula (LIV)], Peak 4=3B-(3-carboxypropanoyl)-MTM [formula (LV)], Peak 5=4',3B-di-(3-carboxypropanoyl)-MTM [formula (LVI)].

Figure 31:
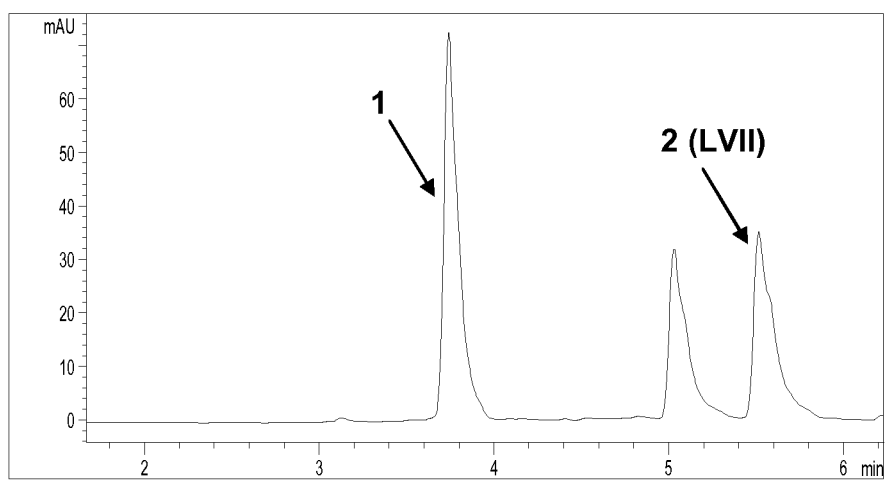

FIG. 31: HPLC analysis of the enzymatic acylation reaction of MTM using vinyl adipate and CAL-A. Peak 1=MTM; Peak 2=3B-adipoyl-MTM [formula (LVII)].

Figure 32:
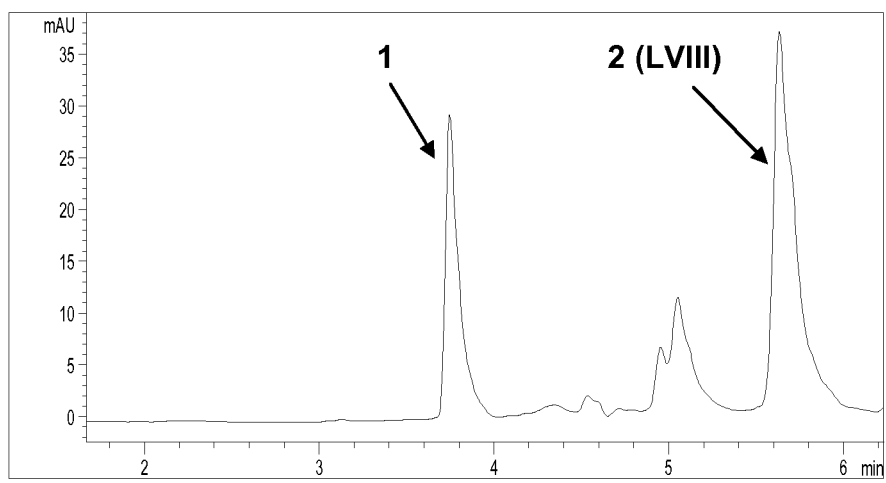

FIG. 32: HPLC analysis of the enzymatic acylation reaction of MTM using vinyl sorbate and CAL-A. Peak 1=MTM; Peak 2=3B-(2,4-hexadienoyl)-MTM [formula (LVIII)].

Figure 33:
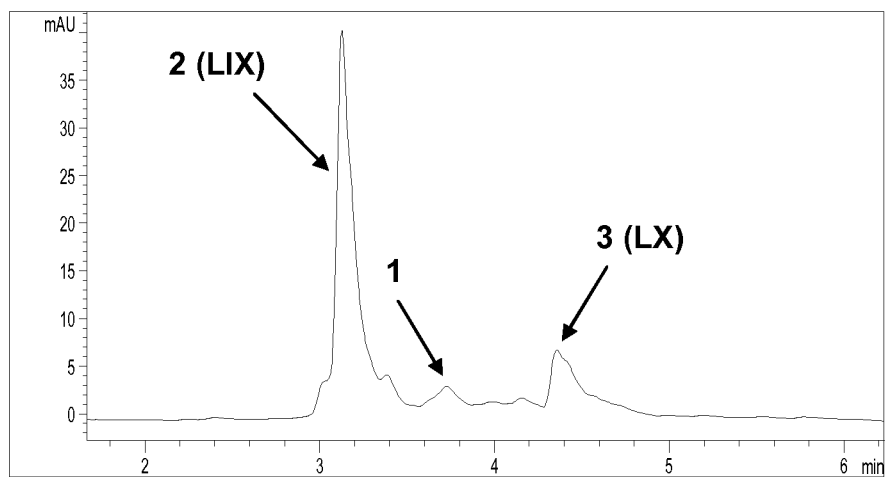

FIG. 33: HPLC analysis of the enzymatic acylation reaction of MTM using vinylene carbonate and CAL-A. Peak 1=MTM; Peak 2=compound of formula LIX; Peak 3=compound of formula LX.

Figure 34:
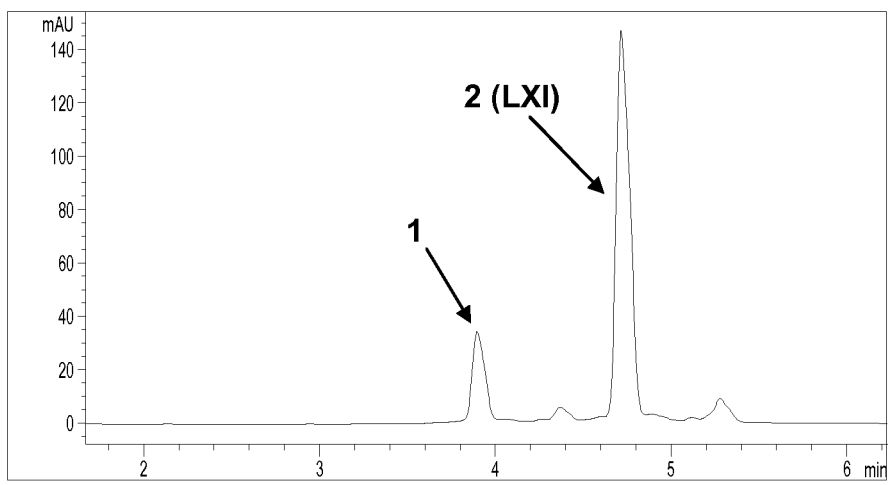

FIG. 34: HPLC analysis of the enzymatic acylation reaction of MTM-SK using vinyl acetate and CAL-B. Peak 1=MTM-SK; Peak 2=3B-acetyl-MTM-SK [formula (LXI)].

Figure 35:
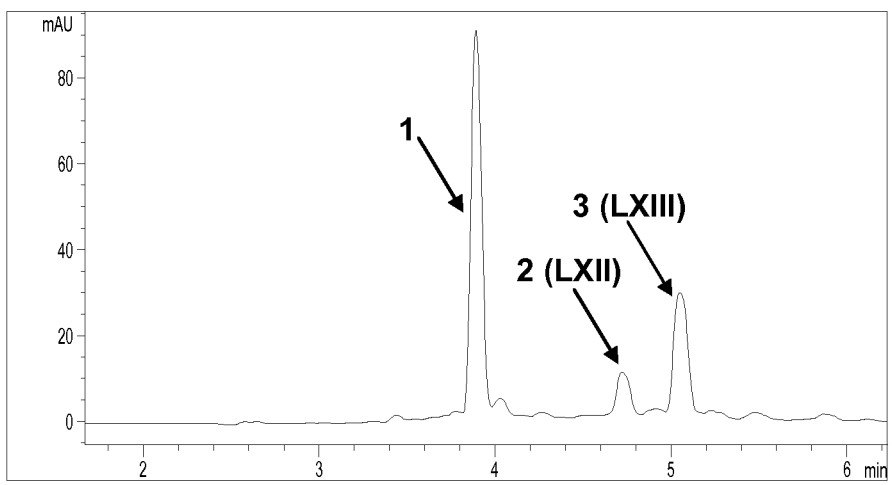

FIG. 35: HPLC analysis of the enzymatic acylation reaction of MTM-SK using vinyl cloroacetate and CAL-B. Peak 1=MTM-SK; Peak 2=compound of formula LXII; Peak 3=compound of formula LXIII.

Figure 36:
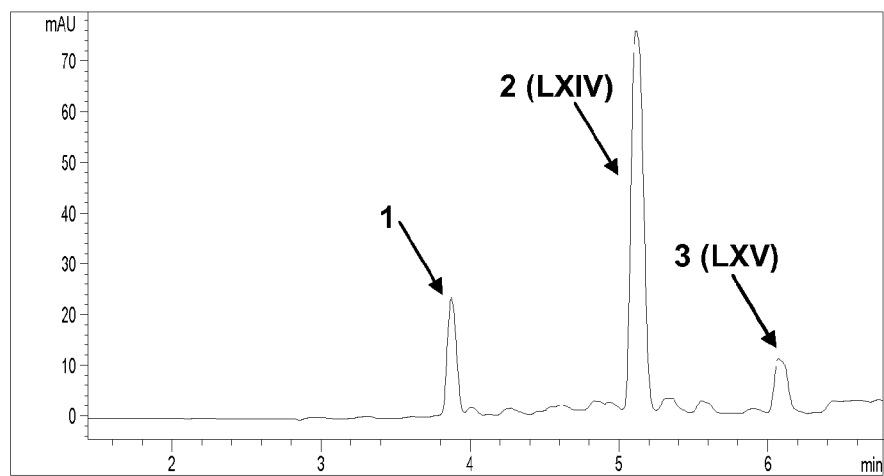

FIG. 36: HPLC analysis of the enzymatic acylation reaction of MTM-SK using vinyl propanoate and CAL-B. Peak 1=MTM-SK; Peak 2=compound of formula LXIV; Peak 3=compound of formula LXV.

Figure 37:
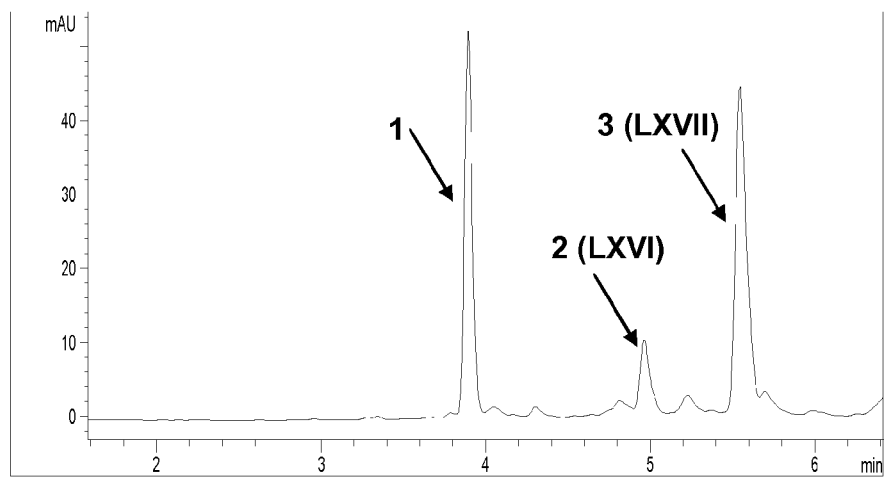

FIG. 37: HPLC analysis of the enzymatic acylation reaction of MTM-SK using vinyl butanoate and CAL-B. Peak 1=MTM-SK; Peak 2=compound of formula LXVI; Peak 3=compound of formula LXVII.

Figure 38:
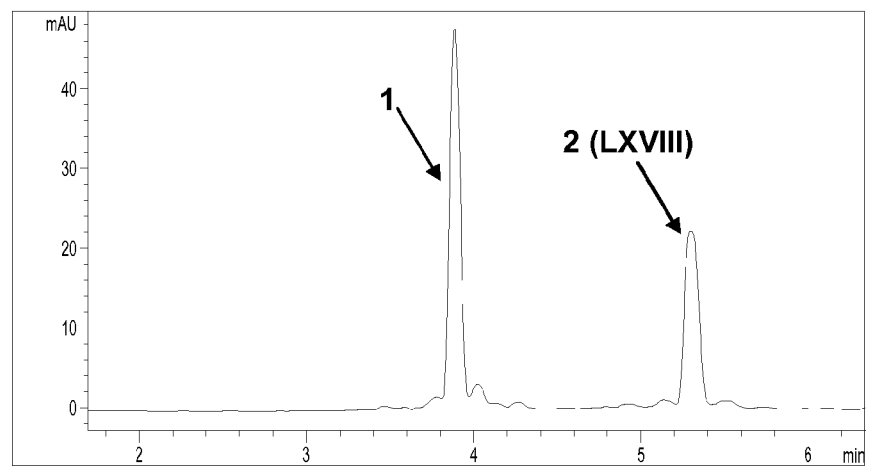

FIG. 38: HPLC analysis of the enzymatic acylation reaction of MTM-SK using diallyl carbonate and CAL-B. Peak 1=MTM-SK; Peak 2=compound of formula LXVIII.

Figure 39:
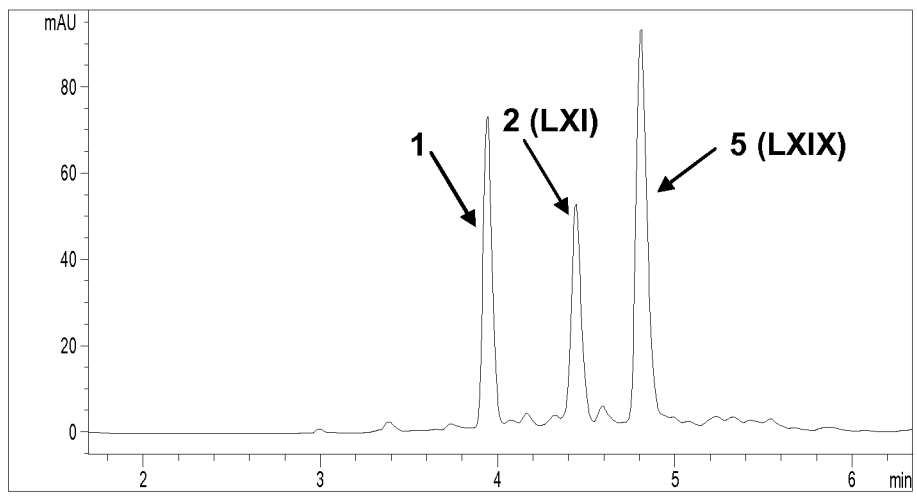

FIG. 39: HPLC analysis of the enzymatic acylation reaction of MTM-SK using vinyl acetate and CAL-A. Peak 1=MTM-SK; Peak 2=3B-acetyl-MTM-SK [formula (LXI)]; Peak 3=4B-acetyl-MTM-SK [formula (LXIX)].

Figure 40:
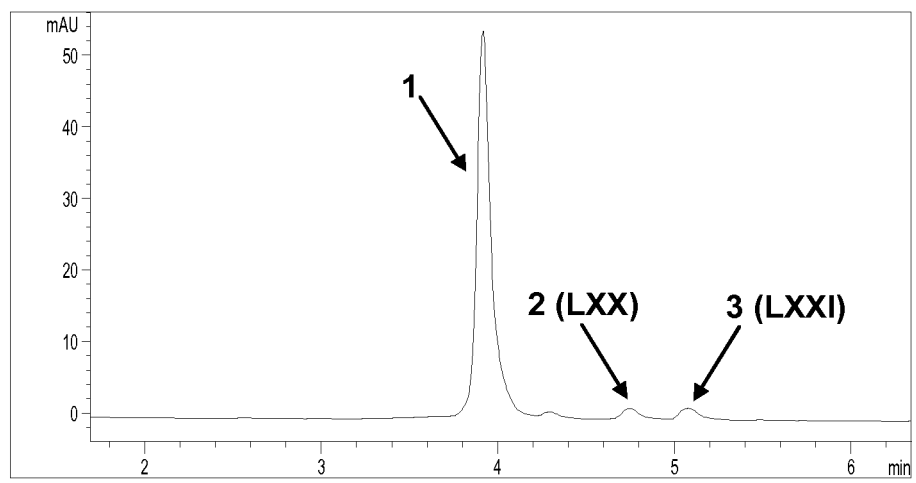

FIG. 40: HPLC analysis of the enzymatic acylation reaction of MTM-SK using vinyl cloroacetate and CAL-A. Peak 1=MTM-SK; Peak 2=compound of formula LXX; Peak 3=compound of formula LXXI.

Figure 41:
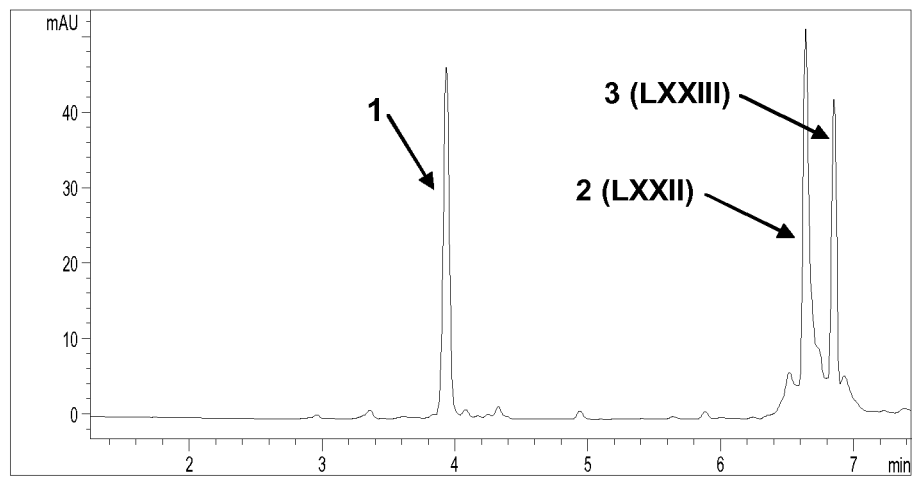
Figure 42:
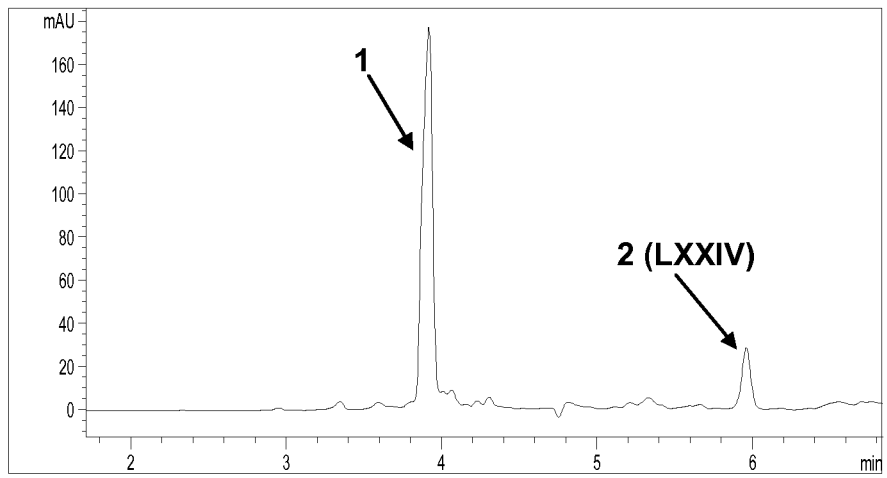

FIG. 41: HPLC analysis of the enzymatic acylation reaction of MTM-SK using vinyl decanoate and CAL-A. Peak 1=MTM-SK; Peak 2=compound of formula LXXII; Peak 3=compound of formula DOOM FIG. 42: HPLC analysis of the enzymatic acylation reaction of MTM-SK using vinyl benzoate and CAL-A. Peak 1=MTM-SK; Peak 2=compound of formula LXXIV.

Figure 43:
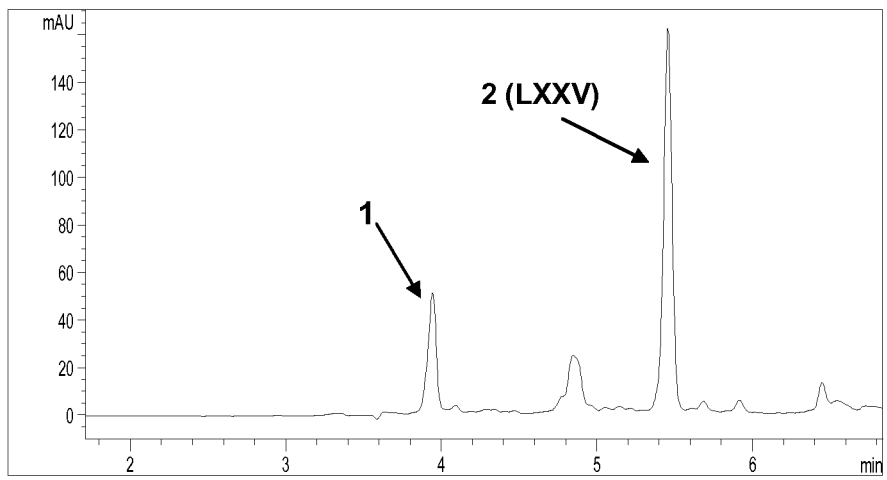

FIG. 43: HPLC analysis of the enzymatic acylation reaction of MTM-SK using vinyl crotonate and CAL-A. Peak 1=MTM-SK; Peak 2=compound of formula LXXV.

Figure 44:
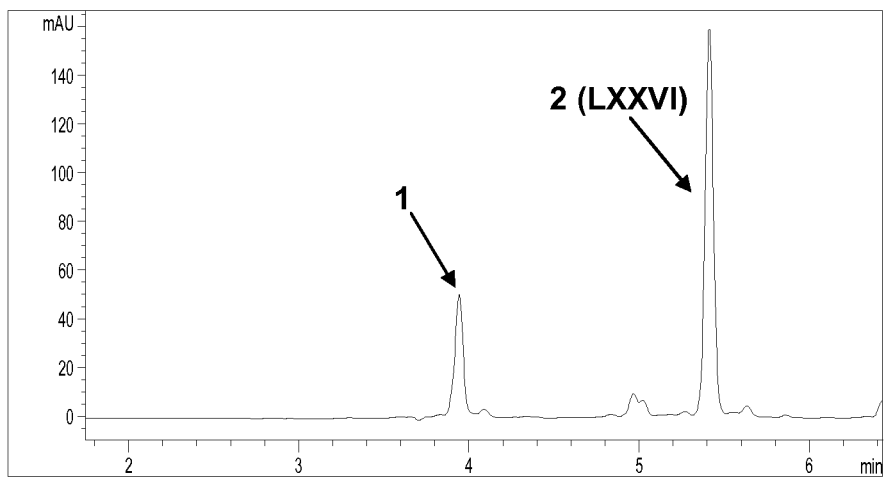

FIG. 44: HPLC analysis of the enzymatic acylation reaction of MTM-SK using diallyl carbonate and CAL-A. Peak 1=MTM-SK; Peak 2=compound of formula LXXVI.

Figure 45:
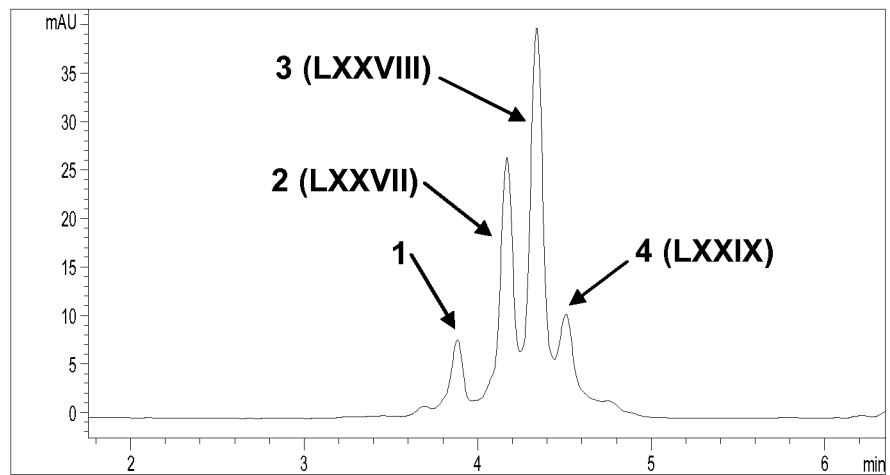

FIG. 45: HPLC analysis of the enzymatic acylation reaction of MTM-SK using succinic anhydride and CAL-A. Peak 1=MTM-SK; Peak 2=compound of formula LXXVII; Peak 3=compound of formula LXXVIII; Peak 4=compound of formula LXXIX.

Figure 46:
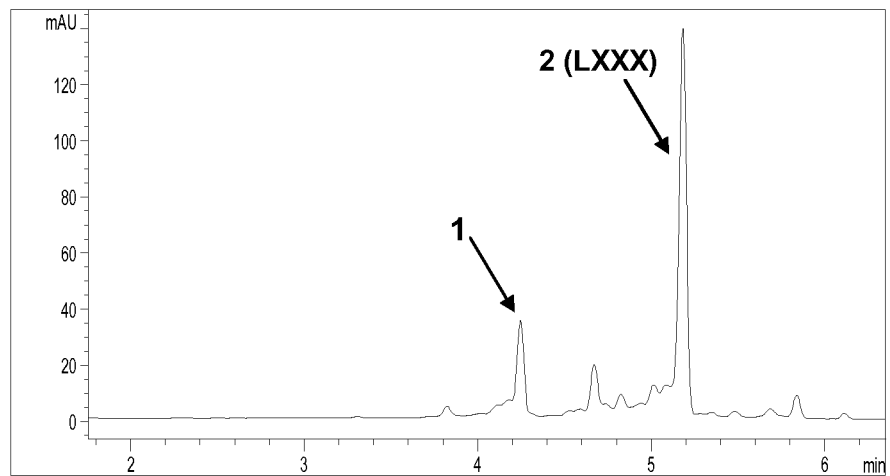

FIG. 46: HPLC analysis of the enzymatic acylation reaction of MTM-SK using vinyl acetate and CAL-B. Peak 1=MTM-SDK; Peak 2=3B-acetyl-MTM-SDK [formula (LXXX)].

Figure 47:
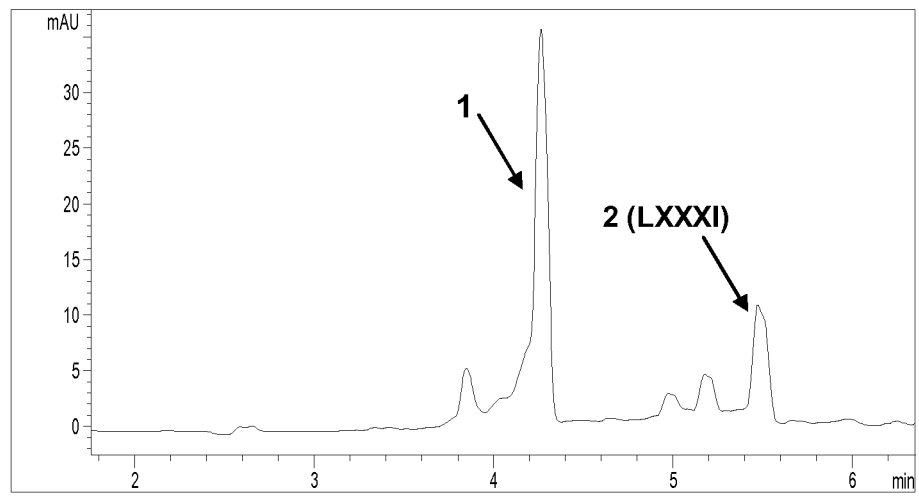

FIG. 47: HPLC analysis of the enzymatic acylation reaction of MTM-SK using vinyl cloroacetate and CAL-B. Peak 1=MTM-SDK; Peak 2=compound of formula LXXXI.

Figure 48:
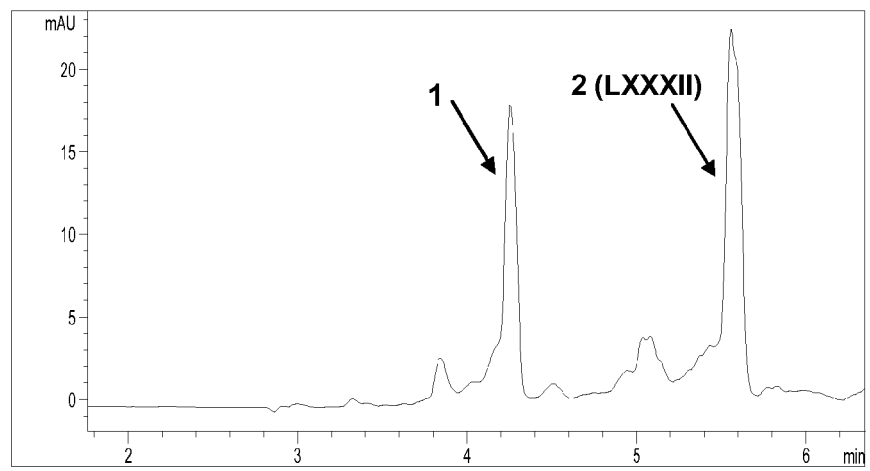

FIG. 48: HPLC analysis of the enzymatic acylation reaction of MTM-SK using vinyl propanoate and CAL-B. Peak 1=MTM-SDK; Peak 2=compound of formula LXXXII.

Figure 49:
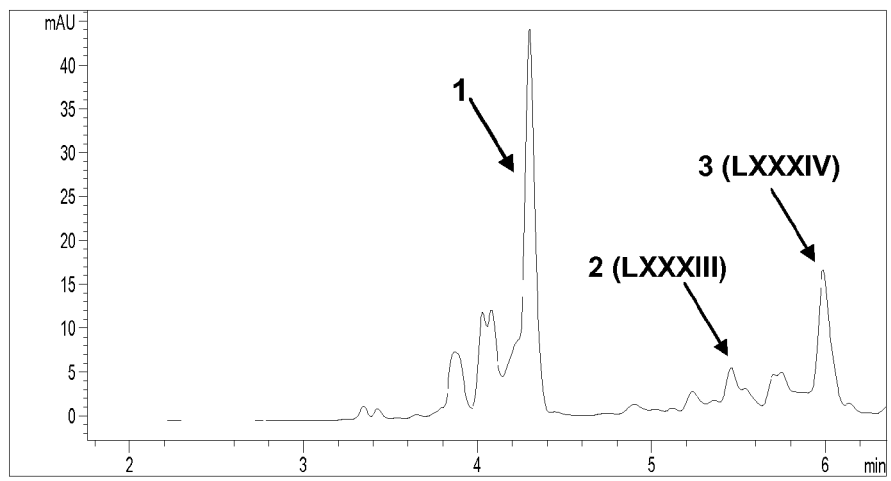

FIG. 49: HPLC analysis of the enzymatic acylation reaction of MTM-SK using vinyl butanoate and CAL-B. Peak 1=MTM-SDK; Peak 2=compound of formula LXXXIII; Peak 3=compound of formula LXXXIV.

Figure 50:
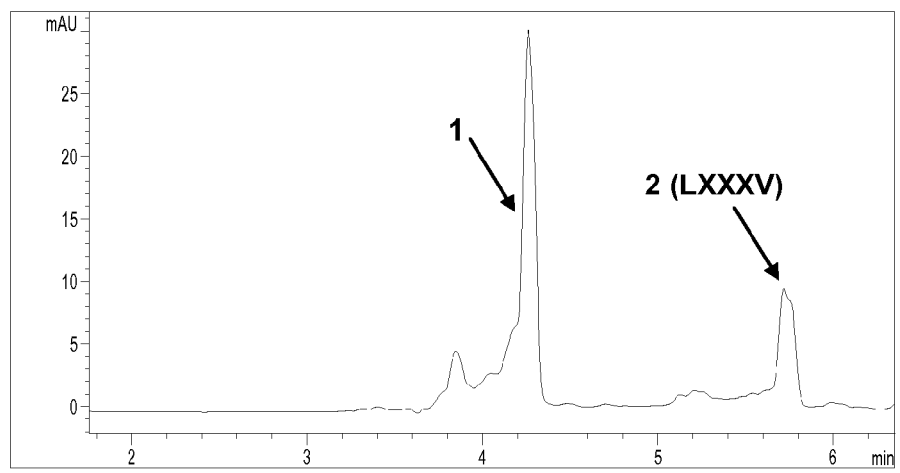
Figure 51:
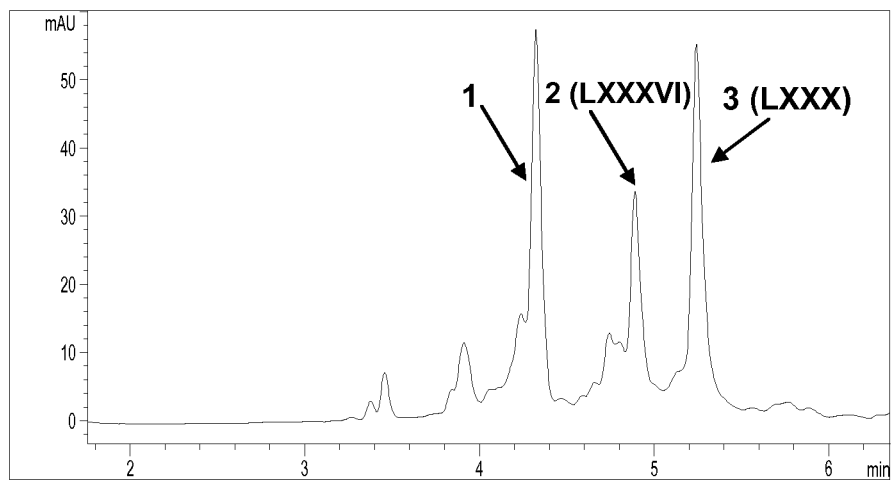

FIG. 50: HPLC analysis of the enzymatic acylation reaction of MTM-SK using diallyl carbonate and CAL-B. Peak: 1=MTM-SDK; Peak 2=compound of formula LXXXV FIG. 51: HPLC analysis of the enzymatic acylation reaction of MTM-SK using vinyl acetate and CAL-A. Peak 1=MTM-SDK; Peak 2=compound of formula LXXXVI; Peak 3=compound of formula LXXX.

Figure 52:
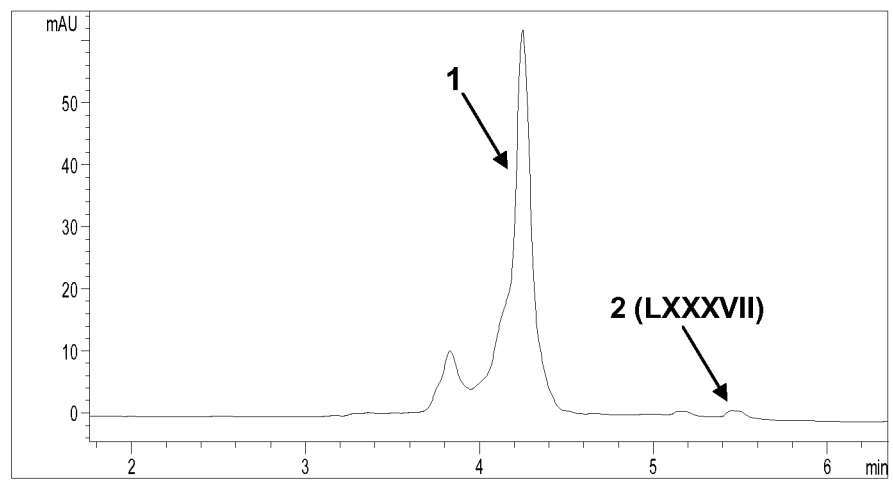

FIG. 52: HPLC analysis of the enzymatic acylation reaction of MTM-SK using vinyl cloroacetate and CAL-A. Peak 1=MTM-SDK; Peak 2=compound of formula LXXXV.

Figure 53:
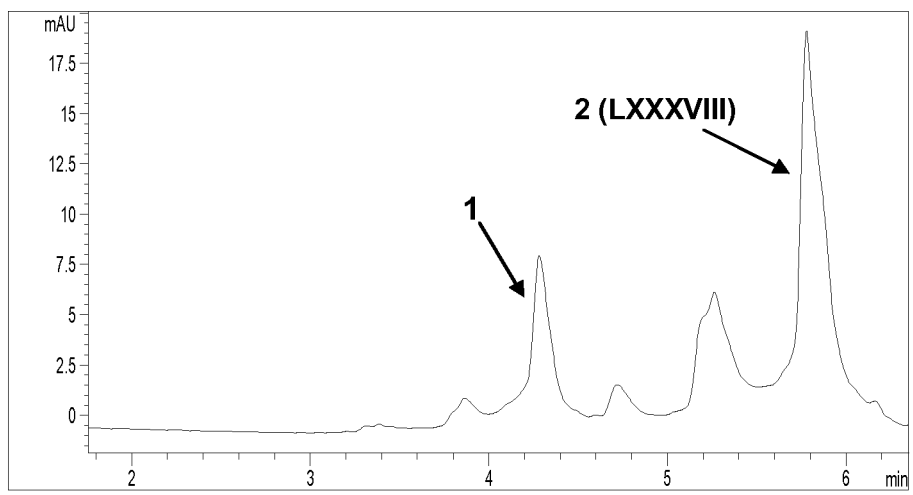

FIG. 53: HPLC analysis of the enzymatic acylation reaction of MTM-SK using vinyl crotonate and CAL-A. Peak 1=MTM-SDK; Peak 2=compound of formula LXXXVIII.

Figure 54:
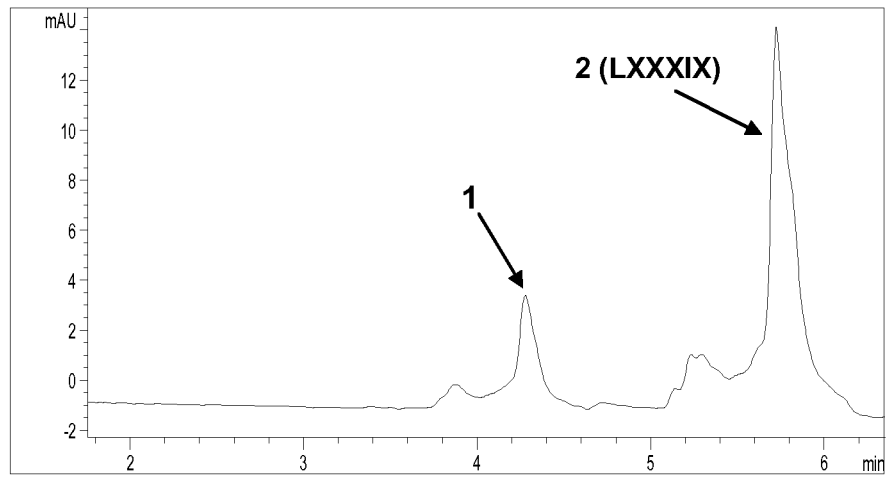

FIG. 54: HPLC analysis of the enzymatic acylation reaction of MTM-SK using diallyl carbonate and CAL-A. Peak 1=MTM-SDK; Peak 2=compound of formula LXXXIX.

Figure 55:
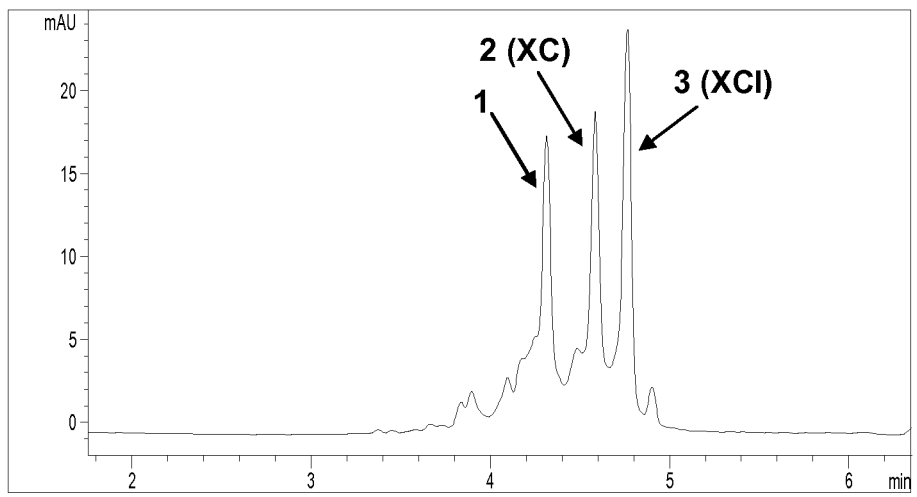

FIG. 55: HPLC analysis of the enzymatic acylation reaction of MTM-SK using succinic anhydride and CAL-A. Peak 1=MTM-SDK; Peak 2=compound of formula XC; Peak 3=compound of formula XCI.

Figure 56:
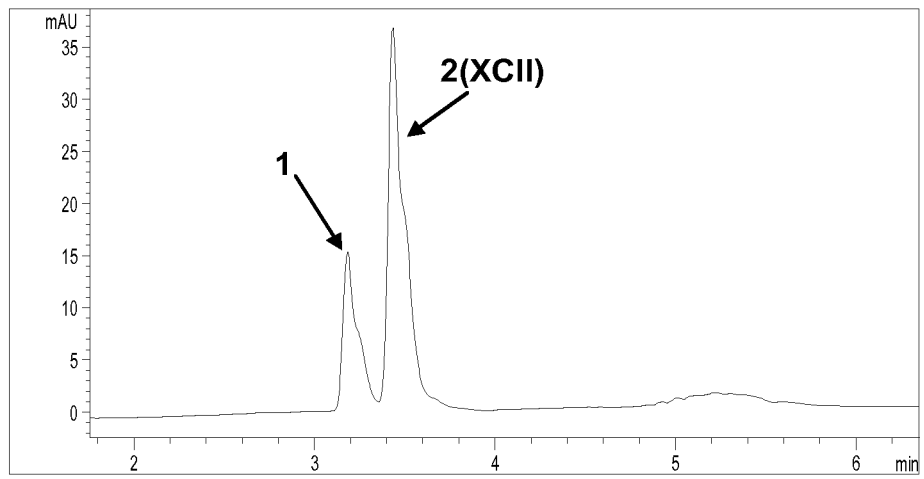

FIG. 56: HPLC analysis of the enzymatic acylation reaction of CRM using vinyl acetate and CAL-A. Peak 1=CRM; Peak 2=4'-acetyl-CRM [formula (XCII)].

Figure 57:
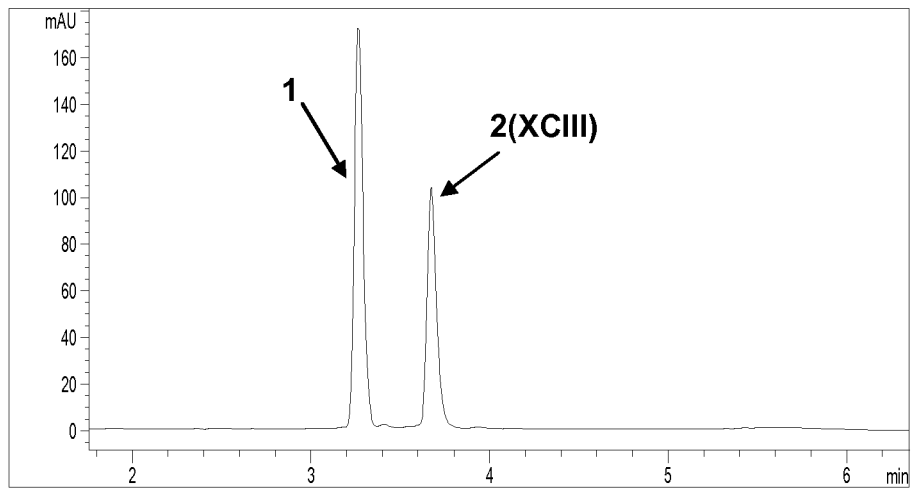

FIG. 57: HPLC analysis of the enzymatic acylation reaction of CRM using vinyl propanoate and CAL-A. Peak 1=CRM; Peak 2=4'-propanoyl-CRM [formula (XCIII)].

Figure 58:
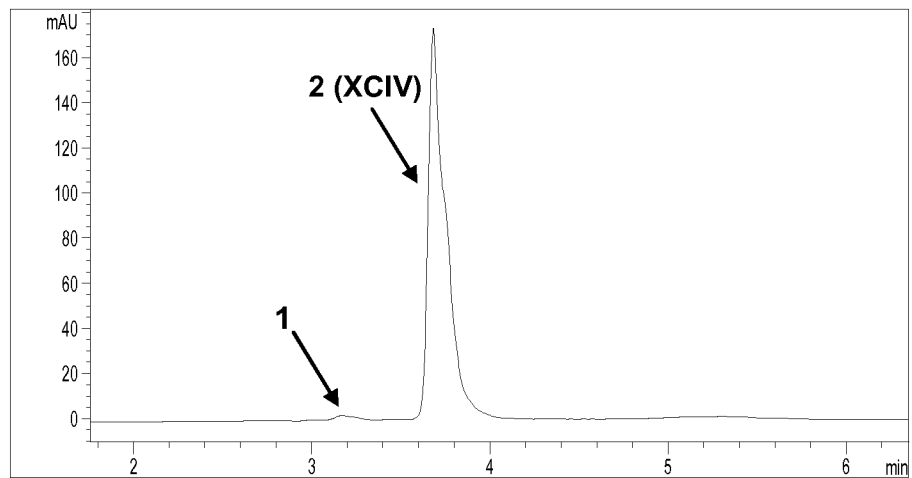

FIG. 58: HPLC analysis of the enzymatic acylation reaction of CRM using vinyl butanoate and CAL-A. Peak 1=CRM; Peak 2=4'-butanoyl-CRM [formula (XCIV)].

Figure 59:
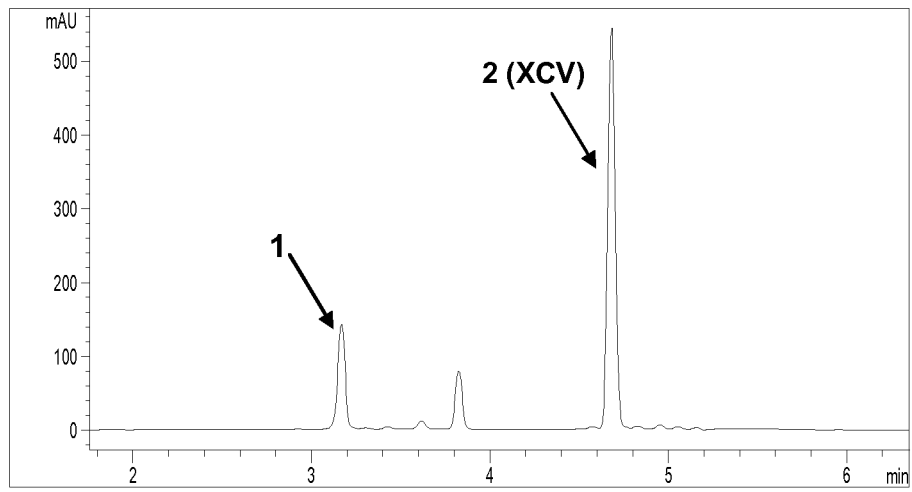

FIG. 59: HPLC analysis of the enzymatic acylation reaction of CRM using vinyl decanoate and CAL-A. Peak 1=CRM; Peak 2=4'-decanoyl-CRM [formula (XCV)].

Figure 60:
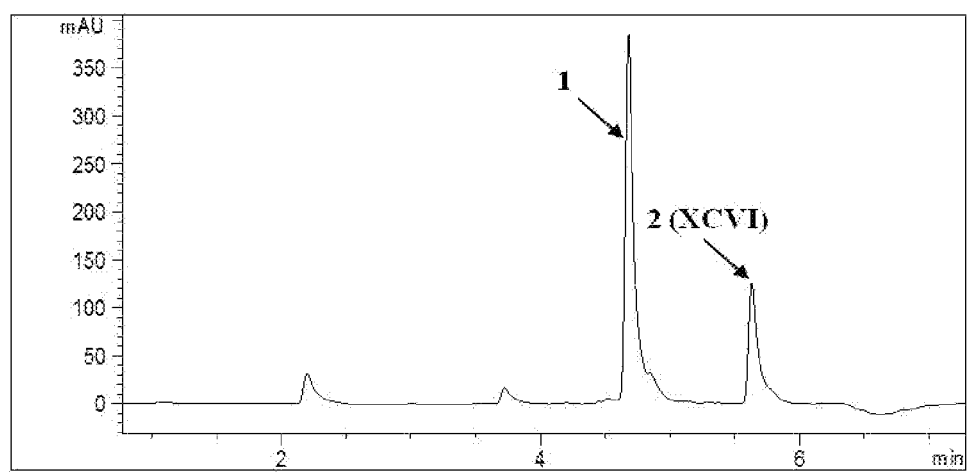

FIG. 60: HPLC analysis of the enzymatic acylation reaction of CRM using vinyl adipate and CAL-B. Peak 1=CRM; Peak 2=4'-adipoyl-CRM [formula (XCVI)].

The invention claimed is:

1. Compound characterized by the formula VII:

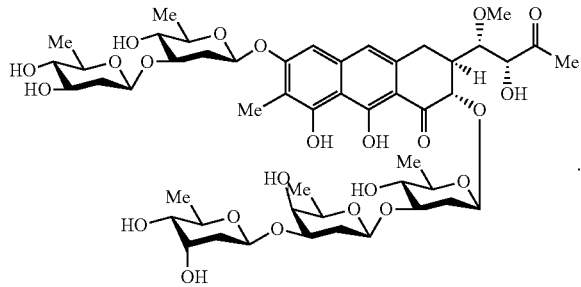

2. A method for treating a subject diagnosed with cancer, Paget's disease, neurological disorders, hypercalcemia or hypercalciuria, said method comprising administering to such subject a therapeutically effective amount of the compound of claim 1 or a salt or a pharmaceutically acceptable formulation thereof.

3. A pharmaceutical composition comprising a compound according to the claim 1 or pharmaceutically acceptable salts thereof.

4. The bacterial strain *Streptomyces argillaceus* ΔAH-W⁻ (pMP3*BII), characterized by having the genes mtmA, mtmH y mtmW inactivated, and also by having an additional nucleic acid comprised in plasmid pMP3*BII, which encodes for enzymes involved in the biosynthesis of the sugar D-digitoxose.

5. A process for obtaining the bacterial strain of claim 4, comprising the introduction of plasmid pMP3*BII in *Streptomyces argillaceus* ΔAH-W⁻.

6. A process for obtaining an aureolic acid derivative characterized by the formula VII, said method comprising:

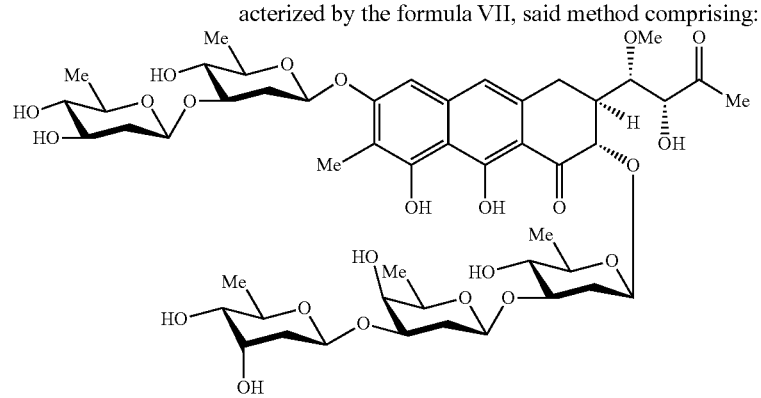

a. Incubating a bacterial strain of claim 4 in a suitable culture medium and
b. Isolating formula VII from the culture medium.

7. A process for obtaining acylated derivatives of aureolic acid comprising a reaction of an aureolic acid according to claim 1 with an acylating agent in the presence of an enzyme.

8. The process of claim 7, wherein the enzyme is a lipase.

9. The process of claim 8, wherein the enzyme is the fraction A or B of the *Candida antarctica* lipase.

10. The process of claim 7, wherein the enzyme is immobilized to a support.

11. The process of claim 10, wherein the immobilizing support of lipase is an epoxyacrylic resin activated with decaoctyl groups.

12. The process of claim 7, wherein the acylating agent is an ester, an anhydride or a carbonate.

13. The process of claim 12, wherein the acylating agent is selected from a group consisting of vinyl acetate, trifluormethyl acetate, vinyl chloroacetate, vinyl propanoate, vinyl butanoate, acetonoxime levulinate, vinyl decanoate, vinyl dodecanoate, vinyl benzoate, vinyl crotonate, diallyl carbonate, allyl oxime carbonate, vinylene carbonate, succinic anhydride, vinyl adipate, and vinyl sorbate.

14. The process of claim 7, wherein the reaction is carried out using the acylating agent itself as solvent.

15. The process of claim 7, wherein the reaction is carried out using tetrahydrofuran as solvent if the acylating agent is a solid or the solubility of the aureolic acid in the acylating agent is low.

* * * * *

UNITED STATES PATENT AND TRADEMARK OFFICE
CERTIFICATE OF CORRECTION

PATENT NO.        : 8,772,253 B2
APPLICATION NO.   : 13/384816
DATED             : July 8, 2014
INVENTOR(S)       : Núñez González et al.

It is certified that error appears in the above-identified patent and that said Letters Patent is hereby corrected as shown below:

Title Page, Item (54) and in the Specification, Column 1, lines 1-3, change Title "AUREOLIC ACID DERIVATIVES, THE METHOD FOR PREPARATION THEREOF AND THE USES" to
-- AUREOLIC ACID DERIVATIVES, THE METHOD FOR PREPARATION THEREOF AND THE USES THEREOF --

Title Page, Item (75), Inventor 6: change "Maria Pérez Solares" to -- María Pérez Solares --

Title Page, Item (75), Inventor 8: change "Maria del Carmen Méndez Fernández" to -- María del Carmen Méndez Fernández --

In the Claims

Column 68, Line 55: change "selected from a group consisting of cinyl acetate, trifluorm-" to
-- selected from a group consisting of cinyl acetate, trifluoro- --

Signed and Sealed this
Fourteenth Day of October, 2014

Michelle K. Lee
*Deputy Director of the United States Patent and Trademark Office*